US007435539B2

(12) United States Patent
Oberste et al.

(10) Patent No.: US 7,435,539 B2
(45) Date of Patent: Oct. 14, 2008

(54) TYPING OF HUMAN ENTEROVIRUSES

(75) Inventors: Steven Oberste, Lilburn, GA (US); Kaija Maher, Atlanta, GA (US); David R. Kilpatrick, Norcross, GA (US); Mark A. Pallansch, Lilburn, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 451 days.

(21) Appl. No.: 11/042,898

(22) Filed: Jan. 25, 2005

(65) Prior Publication Data

US 2005/0123908 A1 Jun. 9, 2005

Related U.S. Application Data

(62) Division of application No. 09/937,862, filed as application No. PCT/US00/07828 on Mar. 24, 2000, now Pat. No. 6,846,621.

(60) Provisional application No. 60/127,464, filed on Mar. 31, 1999.

(51) Int. Cl.
*C12Q 1/70* (2006.01)
*C12Q 1/68* (2006.01)
*C12P 19/34* (2006.01)
*C07H 21/04* (2006.01)

(52) U.S. Cl. ................ 435/5; 435/6; 435/34; 435/91.2; 435/91.3; 435/91.32; 435/91.33; 536/24.33

(58) Field of Classification Search ....................... None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,717,653 A | 1/1988 | Webster et al. |
| 4,965,188 A | 10/1990 | Mullis et al. |
| 5,075,212 A | 12/1991 | Rotbart |
| 5,185,243 A | 2/1993 | Ullman et al. |
| 5,268,465 A | 12/1993 | Bredt et al. |
| 5,516,641 A | 5/1996 | Ullman et al. |
| 5,545,522 A | 8/1996 | Van Gelder et al. |
| 5,578,467 A | 11/1996 | Schuster et al. |
| 5,585,477 A | 12/1996 | Kilpatrick |
| 5,624,833 A | 4/1997 | Gelfand et al. |
| 5,691,134 A | 11/1997 | Kilpatrick |
| 5,723,031 A | 3/1998 | Durr et al. |
| 5,726,012 A | 3/1998 | Bacheler et al. |
| 5,789,208 A | 8/1998 | Sharon |
| 6,846,621 B1 | 1/2005 | Oberste et al. |

FOREIGN PATENT DOCUMENTS

| WO | WO 98/14611 | | 4/1998 |
|---|---|---|---|
| WO | WO9814611 | * | 4/1998 |
| WO | WO 99/53097 | | 10/1999 |

OTHER PUBLICATIONS

Kilpatrick et al. Journal of Clinical Microbiology; Feb. 1998; 36 (2): 352-357, cited in IDS.*
Alksnis et al. Use of synthetic oligodeoxyribonucleotides for type-specific identification of coxsackie B viruses. *Mol. Cell. Probes* 3:103-108 (1989).
Arola et al. Identification of Enteroviruses in Clinical Specimens by Competitive PCR Followed by Genetic Typing Using Sequence Analysis. *J. Clin. Microbiol.* 34(2):313-318 (Feb. 1996).
Bailly et al. Natural Isolates of ECHO Virus Type 25 with Extensive Variations in IRES Sequences and Different Translational Efficiencies. *Virology* 215:83-96 (1996).
Caro et al. Molecular strategy for 'serotyping' of human enteroviruses. *J. Gen. Virol.* 82:79-91 (2001).
Casas et al. Molecular Characterization of Human Enteroviruses in Clinical Samples: Comparison Between VP2, VP1, and RNA Polymerase Regions Using RT Nested PCR Assays and Direct Sequencing of Products. *J. Med. Virol.* 65:138-148 (2001).
CDC. Nonpolio Enterovirus Surveillance—U.S., 1993-1996, MMWR 46(32):748-750 (Aug. 15, 1997).
Chapman et al. Molecular detection and identification of enteroviruses using enzymatic amplification and nucleic acid hybridization. *J. Clin. Microbiol.* 28(5):843-850 (May 1990).
Clements et al. Detection of Enterovirus-Specific RNA in Serum: The Relationship to Chronic Fatigue. *J. Med. Virol.* 45:156-161 (1995).
Cova et al. Use of cRNA probes for the detection of enteroviruses by molecular hybridization. *J. Med. Virol.* 24:11-18 (Jan. 1988).
Diedrich et al. Sequence Comparison of Echovirus Type 30 Isolates to Other Enteroviruses in the 5'Noncoding Region. *J. Med. Virol.* 46:148-152 (1995).
Drebot et al. Molecular Epidemiology of Enterovirus Outbreaks in Canada During 1991-1992: Identification of Echovirus 30 and Coxsackievirus B1 Strains by Amplicon Sequencing. *J. Med. Virol.* 44:340-347 (1994).

(Continued)

*Primary Examiner*—Zachariah Lucas
*Assistant Examiner*—Bo Peng
(74) *Attorney, Agent, or Firm*—Klarquist Sparkman, LLP

(57) ABSTRACT

The present invention discloses a method for detecting the presence of an enterovirus in a clinical sample. The invention additionally discloses a method for typing an enterovirus in a clinical sample. Both methods employ a set of primer oligonucleotides for reverse transcription and amplification that hybridize to conserved regions of the enterovirus genome, and that provide amplicons that include significant portions of the VP1 region that are characteristic of the various serotypes. In the typing method, the invention further provides a database consisting of nucleotide sequences from prototypical enteroviral serotypes, which is used to type the clinical sample by comparing the sequence of its amplicon with each prototypical sequence in the database. The invention additionally provides mixtures of primer oligonucleotides, and a kit for use in conducting the typing method that includes a mixture of the primer oligonucleotides.

13 Claims, 2 Drawing Sheets

OTHER PUBLICATIONS

Figure 1:
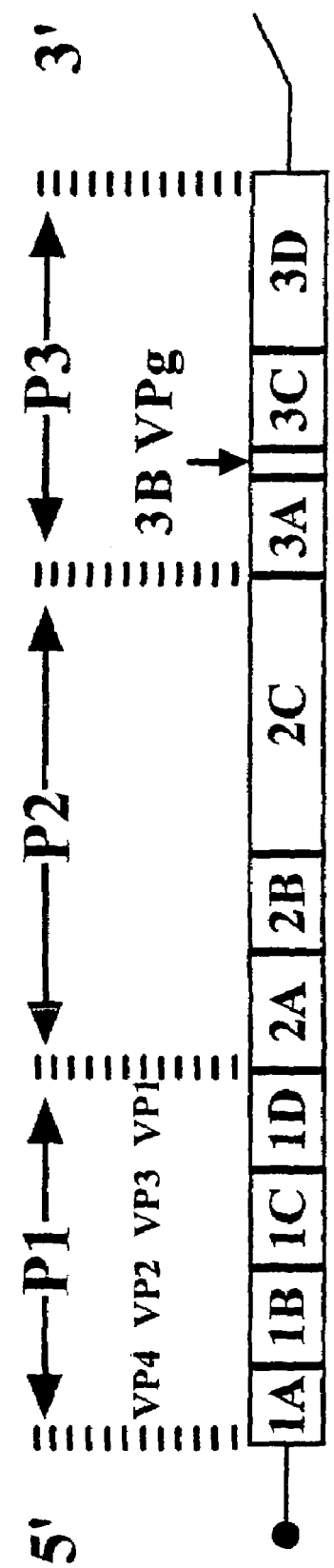

Geneseq databased sequence alignment of instant SEQ ID No. 22 with accession No. AAC34811; entry date : Sep. 24, 1998; primer 43A from WO 98/14611 of Kilpatrick.

Gilmaker et al. Detection of enteroviral RNA by polymerase chain reaction in faecal samples from patients with aseptic meningitis. *J. Med. Virol*. 38:54-61 (1992).

Holland et al. Differentiation and Characterization of Enteroviruses by Computer-Assisted Viral Protein Fingerprinting. *J. Clin. Microbiol*. 36(6):1588-1594 (Jun. 1998).

Hyypia et al. Polymerase chain reaction for human picornaviruses. *J. Gen. Virol*. 70:3261-3268 (1989).

Kilpatrick et al., *J. Clinical Micro*. Feb. 1998; 36(2):352-357.

Kilpatrick et al., *J. Clinical. Micro*. 1996; 34(12):2990-2996.

Kim et al. Nucleotide sequencing of a part of the 5'-noncoding region of echovirus type 9 and rapid virus detection during the acute phase of aseptic meningitis. *Arch. Virol*. 142:853-860 (1997).

Kopecka et al. Genotypic variation in Coxsackievirus B5 isolates from three different outbreaks in the United States. *Virus Res*. 38:125-136 (1995).

Mateu. Antibody recognition of picornaviruses and escape from neutralization: a structural view. *Virus Res*. 38:1-24 (1995).

Melnick et al. Lyophilized combination pools of enterovirus equine antisera: preparation and test procedures for the identification of field strains of 42 enteroviruses. *Bull. W.H.O*. 48:263-268 (1973).

Melnick. The discovery of the enteroviruses and the classification of poliovirus among them. *Biologicals* 21:305-309 (1993).

Muir et al. Rapid diagnosis of enterovirus infection by magnetic bead extraction and polymerase chain reaction detection of enterovirus RNA in clinical specimens. *J. Clin. Microbiol*. 31(1):31-38 (Jan. 1993).

Needleman et al. A General Method Applicable to the Search for Similarities in the Amino Acid Sequences of Two Proteins. *J. Mol. Biol*. 48:443-453 (1970).

Norder et al. Homotype Echoviruses Share Aminoterminal VP1 Sequence Homology Applicable for Typing. *J. Med. Virol*. 63:35-44 (2001).

Oberste et al. Comparison of Classic and Molecular Approaches for the Identification of Untypeable Enteroviruses. *J. Clin. Microbiol*. 38(3):1170-1174 (Mar. 2000).

Oberste et al. Identification and genetic analysis of Panama-genotype Venezuelan equine encephalitis virus subtype ID in Peru. *Am. J. Trop. Med. Hyg*. 58(1):41-46 (1998).

Oberste et al. Molecular Evolution of the Human Enteroviruses: Correlation of Serotype with VP1 Sequence and Application to Picornavirus Classification. *J. Virol*. 73(3):1941-1948 (Mar. 1999).

Oberste et al. Molecular phylogeny of all human enterovirus serotypes based on comparison of sequences at the 5' end of the region encoding VP2. *Virus Res*. 58:35-43 (1998).

Oberste et al. Typing of Human Enteroviruses by Partial Sequencing of VP1. *J. Clin. Microbiol*. 37(5):1288-1293 (May 1999).

Olive et al. Detection and differentiation of picornaviruses in clinical samples following genomic amplification. *J. Gen. Virol*. 71:2141-2147 (1990).

Petitjean et al. Specific detection of enteroviruses in clinical samples by molecular hybridization using poliovirus subgenomic riboprobes. *J. Clin. Microbiol*. 28(2):307-311 (1990).

Rotbart et al. Development and application of RNA probes for the study of picornaviruses. *Mol. Cell. Probes* 2:65-73 (1988).

Rotbart et al. Diagnosis of enteroviral meningitis by using PCR with a colorimetric microwell detection assay. *J. Clin. Microbiol*. 32(10):2590-2592 (Oct. 1994).

Rotbart et al. Diagnosis of Enterovirus Infection by Polymerase Chain Reaction of Multiple Specimen Types. *Ped. Infect. Dis*. 16(4):409-411 (Apr. 1997).

Rotbart et al. Laboratory Diagnosis of Enteroviral Infections. In *Human Enterovirus Infections* (Rotbart, Eds) ASM Press, Washington, D.C. pp. 401-418 (1995).

Rotbart. Enzymatic RNA amplication of the enteroviruses. *J. Clin. Microbiol*. 28(3):438-442 (Mar. 1990).

Santti et al. Molecular detection and typing of human picornaviruses. *Virus Res*. 62:177-183 (1999).

Sequence alignment of instant SEQ ID No. 85 with SEQ ID No. 19947 of US Patent 6,551,795 in the issued patents AA database with an earliest prior filing date of Feb. 18, 1998.

Sequence alignment of instant SEQ ID No. 85 with SwissProt databased accession No: PI=12915 submitted Oct. 1, 1998.

Yang et al. Genotype-specific in vitro amplification of sequences of the wild type 3 polioviruses from Mexico and Guatemala. *Virus Res*. 24:277-296 (Aug. 1992).

Zoll et al. General primer-mediated polymerase chain reaction for detection of enteroviruses: application for diagnostic routine and persistent infections. *J. Clin. Microbiol*. 30(1):160-165 (Jan. 1992).

* cited by examiner

Figure 2

SEQUENCE LISTING

```
<160> NUMBER OF SEQ ID NOS: 89

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 1
gcrtgcaatg ayttctcwgt                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(18)
<223> OTHER INFORMATION: n = a, t, c or g

<400> SEQUENCE: 2
ngcnccdgat tgntgscc                                                18

<210> SEQ ID NO 3
<211> LENGTH: 20
<212> TYPE: DNA
<213> ORGANISM: Artificial Sequence
```

```
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 3
gcnccngayt gntgnccraa                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 4
atgtaygtnc cnccnggngg                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 5
ggngcrttnc cytcngtcca                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 6
acrtgncnng tytgcatngt                                              20

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(18)
<223> OTHER INFORMATION: n = a, t, c or g

<400> SEQUENCE: 7
awnttytayg ayggntgg                                                18
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 8
tananngtnc ccatrttrtt                                           20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 9
atgtayrtnc cnmcnggngc                                           20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 10
ggnggnggrt cngtnakytt                                           20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(20)
<223> OTHER INFORMATION: n = a, t, c or g

<400> SEQUENCE: 11
gangaraayc tnatngarac                                           20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature

```
<222> LOCATION: (1)...(19)
<223> OTHER INFORMATION: n = a, t, c or g

<400> SEQUENCE: 12
cccatnakrt cnatrtccc                                                19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 13
gtrctyacna nnagrtcyct                                               20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(19)
<223> OTHER INFORMATION: n = a, t, c or g

<400> SEQUENCE: 14
tsaarytgtg caargacac                                                19

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(18)
<223> OTHER INFORMATION: n = a, t, c or g

<400> SEQUENCE: 15
stgyccagat ttcagtgt                                                 18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 16
ggnacncayr tnathtggga                                               20

<210> SEQ ID NO 17
<211> LENGTH: 20
<212> TYPE: DNA
```

```
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 17
gccntrttnt grtgnccraa                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 18
ggnacncayr tnrtntggga                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 19
acngcngyng aracnggnca                                                 20

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(19)
<223> OTHER INFORMATION: n = a, t, c or g

<400> SEQUENCE: 20
acngcngtng aracnggng                                                  19

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct
<220> FEATURE:
<221> NAME/KEY: misc_feature
<222> LOCATION: (1)...(20)
<223> OTHER INFORMATION: n = a, t, c or g

<400> SEQUENCE: 21
```

-continued

| cargcngcng aracnggngc | 20 |

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence; Note = synthetic construct
<220> FEATURE:
<221> NAME/KEY: misc_feature
<222> LOCATION: (1)...(19)
<223> OTHER INFORMATION: n = a, t, c or g

<400> SEQUENCE: 22

| cnccnggngg nayrwacat | 19 |

<210> SEQ ID NO 23
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 23

| ggattgggcg attctattga ggctgccatt gacagcatca cacaaaatgc actaaccact | 60 |
| gtacaaaata caacacaatc aggacctact cattcaaaag aagttccagc attaacagca | 120 |
| gtggaaacag gtgctactag tcaagtagaa ccaggtgact tgattgaaac cagacatgtt | 180 |
| ataaacatga gacaaagatc tgaagcatct atcgaatctt tctttggccg atccgcatgt | 240 |
| gttgcgatac ttggtttgtc aaacgccaaa ccaactgaca caaacaccaa acaattgttc | 300 |
| aaaacatgga gaatatcata tttagaaact caccaactca gaagaaaact tgagttcttt | 360 |
| acgtactcaa ggtttgattt ggaaatgacc atagtaatta cagagagggt tttcaatgca | 420 |
| gtcaatgtcc cattgcgcaa ttatgtgtac caaataatgt acgttccccc aggtgctcca | 480 |
| gaaccacaat catgggatga ttacacgtgg caatcttcta ccaacccatc aatattctac | 540 |
| accactggaa atgctcctcc cagagtgtca attccatttg ttggaatagg gtctgcatat | 600 |
| tcacactttt atgatggttt ctcacagatt cctcttgact caatcagtgc tggagcaagt | 660 |
| aataagtatg gttacacttc aatcaatgac tttggtaccc tggcaattag aatagtaaat | 720 |
| gaatatgacc cagtgcaagt ggatgcaaag gcccgagtgt atattaaacc caaacatgtt | 780 |
| cgcatgtggt gccccagacc accacgggcc atgccttaca gaatagcac agtggatttc | 840 |
| gacccatcag caactgtaat gacccaagtc gcagacatca ggacgtat | 888 |

<210> SEQ ID NO 24
<211> LENGTH: 882
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 24

| ggagatccag tggaagactt aatcgccaat acagttgcta ggactctaga gagaataacc | 60 |
| tctccaactc ataatacaac ggcaggcaac accaccgtta gcgagcacag catcggtacc | 120 |
| ggttcagtgc ctgcgttgca agctgctgag actggggctt cgtctaacac cacagatgag | 180 |
| agtatgatag aaacacggtg tgttgtcaat aggaatggag tgattgagac tagcatcaac | 240 |

-continued

```
catttcttct cccgagcggg gcttgtggga gtgctgaaca tacttgatgg aggcacctca      300
aaaggctttg aagtttggga tatagacatc atgggctttg ttcagcttcg cagaaagcta      360
gagatgttca cctacatgcg gttcaacgct gaattcacct tgtcgcgac tttgagtgac       420 ggaacaactc cccatataat gttgcaatac atgtatgtgc ccctggagc tcccaaacct      480 caggaaagag attcattcca atggcagact gcaaccaacc catccgtgtt tgcgaaaatg      540
agtgaccctc ctccgcaagt ttcagtacct ttcatgtctc ctgctagcgc ctaccagtgg      600
ttttatgatg ggtacccaac atttgatgat agaccacaga cctctaatcg tccctacgga      660
caatgcccca ataacatgtt gggcacattc gcggtgcgca ttgttagcaa gacgcctgcg      720
gagagagact tgcgcgtccg tgtttacatg aaactgaagc atgtgcgagc atgggtaccg      780
cgacccataa ggtcacagcc ttacgtcttg aagaactacc ccaactatga tggaacccaa      840
atcgtgccca gtgccaaaga tcgagaagac ataaagaaca ca                        882
```

`<210>` SEQ ID NO 25
`<211>` LENGTH: 915
`<212>` TYPE: DNA
`<213>` ORGANISM: Artificial Sequence
`<220>` FEATURE:
`<223>` OTHER INFORMATION: Description of Artificial Sequence; Note = synthetic construct

`<400>` SEQUENCE: 25

```
ggtgatgcaa tcgctgatgc tatacaaaac acagttacat ctactataca gagagtcaca      60
accaacactg ttgggcaaga tgcaacagct gctaacacag cacccagctc tcatagtttg     120
aacactggcc tagtccccgc gcttcaagct gctgagacag gagcttcatc cacagccacg     180
gatgggaatt tgattgagac tagatgtgtt gtaaactcca atggtacacg tgaaacccac     240
attgagcatt tcttctctag gtcagggctg gtgggagtta tggaggtaga tgatacgggt     300
actagtggca agggattctc aaactgggac attgacatca tggcgtttgt gcaactgcgc      360
cgtaaactcg aggcatttac atatatgcgg ttcgacgcag agtttacctt tgtcaccaat      420
ttggagaacg ggctcacgaa taatagtgtg atacagtaca tgtatgtacc acctggagcg      480
cctaaacccg atgcccggga atcattccag tggcaaactg caaccaatcc gtcagtcttt      540
caaaaaatgg acagtccgcc acctcaagtt tcagtaccct tcatgtcacc agccagtgcc      600
tatcaatggt tctatgacgg ttaccccacc tttgggcccc actcggagac atctaatcta      660
tcttacgggc aatgtcccaa taatatgctg ggaacattct cggccaggg tgttagcaag       720 caaatcacca atcagaaatt ccagatccgt atttatctac ggctgaagag ggtgagggcg      780
tggatcccca gacctttgag atcgcagccg tacatttaca gaaactaccc cacctatggt      840
actaccatcc aatacctggc caaagatagg cgcaagatca ctgaaactga ttataatgct      900
gaacagcgca cgcat                                                      915
```

`<210>` SEQ ID NO 26
`<211>` LENGTH: 885
`<212>` TYPE: DNA
`<213>` ORGANISM: Artificial Sequence
`<220>` FEATURE:
`<223>` OTHER INFORMATION: Description of Artificial Sequence; Note = synthetic construct

`<400>` SEQUENCE: 26

```
ggcagaccaa ttgcagatat aatagaagga gcagtagctc aaactaccac cagagcacta      60
agtggaccaa ttcagccagt gacagcggcc aacacctctc ccagttcaca tcggcttggt     120
```

```
acggggcaag tgccagcttt gcaagcagca gaaacgggag ccacctcgaa tgcgaccgac      180
gagagtttga ttgaaaccag gtgtgtggtc aacagacatg gagtcatgga aactagcatt      240
gaacacttct tttcacgctc aggcttggca ggaattttga taattgagga ctccggtact      300
tccacgaaag gctacgccac ttgggaaatc gatgttatgg gatttgtcca gctgaggcgt      360
aaactagaga tgttcacata catgcgattt gatgcagagt tcacctttat cacagcagaa      420
aggaatggca acaccagccc aatacccatc cagtacatgt atgtcccacc cggagcccca      480
gtccctactg gtagggagac attccaatgg caaacagcga ccaatccatc cgtgatctca      540
aagatgactg atccaccagc ccaggtgtct gtaccattta tgagcccagc cagtacttat      600
caatggttct acgatggcta ccccacgttc ggagaagttc cagtgactac gaacttgaac      660
tatggacagt gcccaaacaa caaaatgggc actttctgca tccgcatggt ctcaggtgta      720
tctacaggca aggacgtcac tgtgcgcatt ttcatgaagt tgaagcatgt gcgcgcctgg      780
gtgccaaggc ccatcaggag ccagccttac ttgttaaaga attatcccaa ctttgacaag      840
tcaaatattg tagacgcatc atcgaacagg acatatacca ccact                      885

<210> SEQ ID NO 27
<211> LENGTH: 915
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 27
aatgacccca tttcaaatgc aatagaaaat gctgtgagca cactcgctga caccacgata       60
tcacgtgtta cagcggccaa cactgctgct agctcccatt cccttggtac tggacgcgtg      120
ccggcgttgc aggctgcgga gacaggggca agttccaacg ctagcgatga aacctgatt      180 gaaactcgtt gtgtgatgaa tagaaatgga gttaacgaag caagtgtaga acacttctac      240
tcccgtgcag ggctagtagg agttgtggag gtgaaagact caggcactag tcaggacggg      300
tacacggtgt ggcccataga tgtgatgggc tttgtgcaac agcggcgcaa gttagagcta      360
tctacttaca tgcgctttga cgctgaattt acctttgtgt ccaatctcaa tgacagcaca      420
acacccggca tgctattgca gtacatgtac gtgccgccgg gtgcgcccaa accagacggt      480
aggaagtcat atcaatggca aacagccacc aaccccttcaa tattcgcaaa gttgagtgac      540
ccaccgcccc aagtgtctgt cccattcatg tcaccggcgt cagcctacca gtggttctac      600
gatggttacc ccacgtttgg cgaacacaag caagctacta atttacaata cggtcagtgc      660
cctaacaaca tgatggggca ttttgctatt cggacagtta gtgaatccac caccgggaaa      720
aatgtccatg tccgggtgta catgagaatt aagcacgtaa gagcatgggt gcccagacct      780
ttcagatccc aagcttacat ggtcaaaaac tacccgacat acagccaaac aatatccaat      840
actgcagccg atcgtgcgag cataaccact acggactatg agggtggcgt accagcaaac      900
ccgcagagaa ctttt                                                        915

<210> SEQ ID NO 28
<211> LENGTH: 888
<212> TYPE: DNA
<213> ORGANISM: Artificial Sequence
<220> FEATURE:
<223> OTHER INFORMATION: Description of Artificial Sequence; Note =
      synthetic construct
```

```
<400> SEQUENCE: 28
ggagacgaaa tactcgacct aatcgagagt gctgtacaga ataccactaa agccattacc    60
agctcaatcg acaccaaaac tggtgctaac actcaagcta gccaacatcg tataggcttg   120
ggggaggttc ccgctcttca agctgctgag acaggatcgt cttcgctcgt ttcggacaag   180
aacatgatag aaacaaggtg tgtcgtaaac aaacacagca cagaggaaac cagcattaca   240
aacttctact ccagggcggg cctagtgggg gttgtgaaca tgccagtaca aggaaccagc   300
aacacaaagg gtttcgcaaa gtggggata gatataatgg gctttgtgca gatgaggcgc    360
aaacttgagc tcatgacata catgagattc tccgccgagt ttacgttcgt acccagcact   420
cctgggggag agactactaa ccttatactg caatacatgt atgcacctcc cggagctccg   480
ctgccaacca ggcgggattc atacgaatgg caaacatcca ctaaccctc tattatcagc    540 aagatggcgg acccacccgc tcaggtatcg gttccattcc tttctcctgc atcagcatat   600
cagtggttct atgatggcta ccccacattt gggaaacacc aatagatca ggacttccaa    660 tatggcatgt gcccaaacaa catgatgggc acattctgtg tgcgcatgat cggtgggggc   720
aaaccgaccc aatcagttac catacgtata tacatgagat taaagcatat ccgtgcatgg   780
gtgccccggc cactgaggag tcagaattac actatgagga attacccgaa ctacaacggg   840
ggcgcaataa aatgtacatc aaaaagcaga gctaccataa caacctta              888

<210> SEQ ID NO 29
<211> LENGTH: 882
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 29
ggagattcca ttgaagacat aataagcaac actgtcaccc gtacactgca acaaatcagt    60
gccccatcac acgacactac agcagccaac acctcagtga gtaatcataa aattggtacg   120
ggggatgtcc cagctctcca agctgcagag actggcgcta cttccaatgc ctcagacgag   180
aacatgattg agacacgatg tgtgttaaat cgcaatgggg ttgtggaaac tagtttggac   240
catttctttt caagagcagg ccttgtggga gtgatcaatg tgcaagatgg cggcactcag   300
aagggttttg aagtgtggga catagatgtc atggggtttg ttcaactcag gaggaagttg   360
gagatgttca cgtacatgag gttcaacgcc gagttcacat tcgtatccac actcgcggat   420
ggcacaactc ccagagtgat gttgcagtac atgtacgttc cacctggtgc ccccaaacct   480
caggagagag attcgtttca gtggcaaact gcaaccaacc catcagtatt ttgcaaaatg   540
agtgaccctc ctccacaggt ttccgttcct ttcatgtcac cagctagtgc ctaccaatgg   600
ttctacgatg gtacccaac attcgatgat cgaccggcca cctcaaacca cccgtacgt    660 cagtgcccca ataacatgat gggcacattc gcagtgcggt ttgtcagcaa gacccagcc    720 acacgggatc tgcgtgtcag agtgtacatg cgcctgaaac acgtgcgcgc atgggtaccg   780
agacctatcc gatctcaacc ctatattttg aaaaactacc caaattatga tggcacaaag   840
ataacgtcga catctaagga taggcaaagc atcaaaacaa ca                     882

<210> SEQ ID NO 30
<211> LENGTH: 894
<212> TYPE: DNA
<213> ORGANISM: Artificial Sequence
<220> FEATURE:
```

<223> OTHER INFORMATION: Description of Artificial Sequence; Note = synthetic construct

<400> SEQUENCE: 30

```
ggcgaccccg tggaggacat catccacgac gctttgagca gcactgtgcg gcgggccata      60
actagtggtc aagatgtcaa cacagcggcc ggtaccgctc ctagctctca caggttggag     120
actggtcgtg ttcccgccct acaagcagca gaaactggag ccacttctaa cgctacagat     180
gagaacatga tagaaacgcg gtgtgtcatg aacagaaatg gagtgttgga ggcgactata     240
agtcatttct tctcacgctc aggtttggtg gtgttgtca atctaactga cggaggcacc      300
gatacaacgg gatatgcagt gtgggacatt gacatcatgg gttttgtgca actgcggcgg     360
aaatgtgaga tgttcacata catgagattc aacgctgagt tcacattcgt cactacaaca     420
gaaaatggcg aggcaaggcc atttatgtta cagtatatgt atgtacctcc aggtgcccct     480
aagccaacgg gtagagatgc ttttcagtgg caaacagcga caaatccatc cgttttcgtt     540
aagctcacag atccacctgc tcaggtatca gtccccttca tgtcacctgc tagtgcctac     600
caatggttct atgacgggta tccaacattt ggacaacacc cggaaacatc taatacaaca     660
tatggacagt gccctaacaa catgatgggg acctttgctg tgagagtagt gagtagagtg     720
gctagccagc tcaaactaca gacacgagtg tatatgaagc ttaagcatgt gagagcatgg     780
atccctaggc caataagatc ccagccttac ctcctaaaga attttccaaa ttatgatagt     840
agtaagatca catacagcgc aagagatcgt gccagcataa acaagctaa tatg            894
```

<210> SEQ ID NO 31
<211> LENGTH: 912
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 31

```
gggccaatag aagaaatcat ctcaactgtt gccagtaacg cgttggcgct cagtcaaccc      60
aagccagtgg acaactctgt acaaaacacc caacaaagtg ctccagtgca tagccaggag     120
gtgccagcat tgaccgcagt ggagacaggg gcgacaagtg atgtggttcc atctgaccta     180
attcagacta gacacgtatt gaatgttaaa tccaggtctg aatccaccat cgagtcattt     240
tttgcaagag ctgcatgtgt aaccattatg caggtggaca atttcaacgc aacctctgtg     300
gaagacaaaa gaaagttgtt tgctaaatgg gcaatcacct acactgatac cgtccagctg     360
agacggaaat tagagttttt cacttattct agatttgact tagagatgac ttttgtgcta     420
actgagagat actactccca aagctcaggg catgctagat ctcaggtgta ccaaattatg     480
tatgttccac caggggcacc cacgcctagt gcatgggacg actacacatg gcaaacatcc     540
tccaacccat ccatttttctt taccaccggc aatgcaccac cgcgcatttc aattccattt     600
gttggaatcg ccaatgcata ctcacacttt tatgatggct ttagtagagt acctttggag     660
ggagaaacaa cagacacagg agacgcttac tacgggctca cttcaataaa cgattttggt     720
acacttgcag tcagggtagt taatgactac aacccagcca gggtggagac aaggattaga     780
gtatacatga agcccaaaca tgtgagagtc tggtgcccgc gacctccaag agcggtaagc     840
tacagaggac ctggagtcga cctcctatca acatcagtaa cacctttatc caaacatgac     900
ctagcgacat ac                                                         912
```

<210> SEQ ID NO 32
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 32

| | | | | | |
|---|---|---|---|---|---|
| ggagatacag | tgagtgatat | gatcgaaaat | tccatcaacc | gaattaccag | tgcaatttcc | 60 |
| actacccaga | cacaccagac | agcagctgac | actagagtta | gtacacacag | gttaggcacg | 120 |
| ggggaggtgc | cacctttaca | agcagcagag | acaggtgcca | cctccaacgc | aaccgacgag | 180 |
| aacatgattg | aaacacgctg | tgtcgtcaac | aggcacgggg | tgagcgagac | cagcgtggaa | 240 |
| tacttcttct | ctcgctctgg | tttggcagga | atagtcatcg | tggaggatgc | aactgccact | 300 |
| aataagggtt | atgccacatg | ggagattgat | gtcatggggt | tcgcgcaact | gcgtcgcaag | 360 |
| ctggagatct | tcacatacat | gcgcttcgat | gcagagttca | cttttgtggc | aacagaacgc | 420 |
| aatgggagca | ccagcccggt | catgatgcag | tacatgttcg | tgcccctgg | cgcccctgtt | 480 |
| ccaacaggga | gagatacctt | ccaatggcaa | tctgctacta | acccttcagt | gctagtaaaa | 540 |
| atgacggatc | caccggccca | agttgccatc | ccctttatgt | ctccagctag | tgcataccaa | 600 |
| tggttctatg | atggatatcc | tacctttgga | gaaagaccag | ttacaaccaa | catgaattat | 660 |
| ggacagtgtc | ccaacaacaa | aatgggaact | ttttgtatac | gcactgtctc | cggtgaagcg | 720 |
| tcagggaaaa | acatcactat | acgtattttt | atgaggttga | agcatgtaag | agcgtgggtg | 780 |
| cctcgcccaa | ttagaagcca | gctatatctg | cttaaaaatt | accccaactt | tgataacact | 840 |
| aagatcctca | acgcctccca | caacagagct | tctatcacat | caaacaca | | 888 |

<210> SEQ ID NO 33
<211> LENGTH: 927
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 33

| | | | | | |
|---|---|---|---|---|---|
| gggttggaag | atctaataca | acaagttgcg | tctaacgcat | tacaattgtc | ccagccaaca | 60 |
| agaccggcac | tcccaccagc | cgagcagagt | gtccccaaca | ctaaccaaac | aactccagaa | 120 |
| cactccaagg | aagtcccagc | gttaacggca | gttgaaactg | cgccacgaa | tcctctagag | 180 |
| cctggcgaca | cagttcagac | tagacatgtg | atacaaacta | gaagtagaag | tgaaagtaca | 240 |
| gtggagtctt | tctttgcgcg | aggtgcatgt | gtaaccatta | tgggagtgga | caactataat | 300 |
| gagacattga | aaggagacca | gaagtctact | ctatttacaa | cctggaacat | cacctacact | 360 |
| gacacagtcc | agctacggag | aaaactggaa | atgttcactt | actccaggtt | tgacatcgag | 420 |
| tttactttg | tggtgactga | acgctactac | tcatcaaaca | gtgggcatgc | tctgaaccaa | 480 |
| gtgtaccaaa | ttatgtatgt | accacctgga | gcaccagtgc | caaagaaatg | ggatgattac | 540 |
| acctggcaaa | cctcttcaaa | cccgtccata | ttctacactt | atgggtcagc | accacccagg | 600 |
| atatccatac | cctttgtggg | tatagcaaac | gcttactccc | acttctatga | tgggtatgcg | 660 |
| acagtgccct | tgaaaactga | caccacagac | tcaggagcag | cctactatgg | agcagtatcc | 720 |
| ataaacgact | tcggactgct | tgcagttcgc | gtcgtcaatg | aacataatcc | agtcagagta | 780 |
| tcatccaaaa | ttagagtgta | tatgaaacca | aaacatgtca | gggtatggtg | tcccagacct | 840 |

-continued

| | |
|---|---|
| ccaagggctg tagagtatta tggaccagga gtggactaca aggcaaacac tttaacaccg | 900 |
| ttgccaataa agaatttgac tacttat | 927 |

<210> SEQ ID NO 34
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 34

| | |
|---|---|
| ggtgacaaag tggcagacat gattgagacc gcagtggaga agaccgtgtc ctcactaact | 60 |
| tccctattc aaaccccac agccgccaac acaaacgtga gtaatcatcg aattgagctg | 120 |
| ggggaagtcc cggctttgca agctgctgaa accggcgcga cgtctcttgt gtctgatgaa | 180 |
| tacttgatag agactcgttg tgtagtgaat agccatagta cagaggaaac tacagtgggg | 240 |
| cacttctttt caagagcggg gttggtggga gtgattgacc tcccattaca gggaacagtc | 300 |
| aacacaggag gattcgcctc gtgggatatt gatgtaatgg gatatgttca gatgagaagg | 360 |
| aaacttgagc tgttcacata tgcccgcttc gatgcggagt ttaccttcat agcttccacc | 420 |
| ccagatggcg aggtgaagcc agtgttctta cagtacatgt tcgtccccc tggtgcacca | 480 |
| aaaccaacag ggcgcaacac ctacgaatgg caaactgcaa caaacccttc tgtgttggtc | 540 |
| aagagcacag atcctccagc acaagtctct gtaccgttca tgtcaccagc cagcgcatat | 600 |
| cagtggttct atgacgggta cccaaccttt ggaaagcacc tgcctgctga tgactttcag | 660 |
| tacggtatga ccccaaataa catgatggga tcgttctgtg ccaggatagt ggggaagga | 720 |
| gcgcctagtg tacacttggt tatccgtatc tacatgcgca tgaaacacgt gcgggtgtgg | 780 |
| attccacgac ctatgcgcag ccagccatac gttgcgaaga attaccctaa ctacaagggt | 840 |
| tctgagatca agtgcgcatc atctagtcgt aagtcaatca ccacatta | 888 |

<210> SEQ ID NO 35
<211> LENGTH: 912
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 35

| | |
|---|---|
| gggccaatag aggagatcat ctcgaccgtc gccagcaatg cacttgccct cagtcagcct | 60 |
| aaaccggtgg ataattctgt acaaaacacc caacagagcg cgcccgtgca cagccaagag | 120 |
| gttccagcat taacagcagt agagactgga gcaacaagtg atgtggtgcc agctgatcta | 180 |
| gtgcaaacca ggcatgtagt gaatgtcaag tccagatctg agtccactat cgagtcgttc | 240 |
| tttgcaagag ctgcctgcgt gactatatg caggttgata actttaatgc caccaccacg | 300 |
| gaggacaaga ggaagttatt tgccaaatgg gccatcacat acacagacac agtacaattg | 360 |
| aggaggaaat tggaattttt cacgtactcc aggttcgatc ttgagatgac tttcgtgcta | 420 |
| actgaaagat actattctca gagctcggga cacgctagat cgcaggtgta tcaaatcatg | 480 |
| tacgtccctc caggagcacc aacaccaaat gcatgggatg attacacgtg gcagacgtct | 540 |
| tctaacccat caattttctt caccactggt aacgcacccc cacgggtttc aatcccattt | 600 |
| gtgggcattg caaatgctta ctcacacttt tatgatggct tcagcagggt acctttggaa | 660 |
| ggagagacca ctgactcagg tgacgcttat tatggcctca cttctatcaa tgactttgga | 720 |

```
acacttgcag taagagtggt caatgactac aacccagcga gagtggagac aaggatcaga      780
gtctacatga aacctaagca tgtgagagtg tggtgtccac gacccctag ggctgtgagc       840 tacagaggac ccggtgtgga cctactgtcc acctcagtga cgcccctatc taagcatgaa      900
ttgacaacgt ac                                                         912

<210> SEQ ID NO 36
<211> LENGTH: 918
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 36
ggcattgaag acttgatcca acaggttgca tcgaatgcgc tgcaaatctc acagccgacg       60
cgtccggcac tgccctctac agaaagtctt cccaacacac aacaatcggc accttcgcat      120
tctcaagagg tcccggcgct gacagcagtt gagacaggcg cgacaaatcc attggagccg      180
tctgacacgt tacaaacaag gcatgttatc cagactagat ccaggtcaga gtccacaata      240
gagtccttct tcgcgcgtgg tgcatgtgtg acaatcatga cagtggaaaa ttttaacgcg      300
actgaggcgg cagacaagaa aaagttgttc gccacttgga atattacata cagacaca       360 gtgcagctca aaggaagtt ggagatgttc acttactctc gatttgacat tgaatttacc      420
tttgtcacca cagaaaggta ctacgccagt aactcaggcc atgcgcgtaa tcaggtttac      480
caactcatgt atgtaccccc aggagccct gtgccacaac aatgggatga ttacacgtgg      540
caaacttcct ccaacccatc ggtgttttac acatacggtg acgctccagc gcgcatttcc      600
ataccatttg tagggatagc taatgcctat tcccactttt atgacggcta tgcagtggtg      660
ccattgaaag attccaccca ggatgctggt gctgcctatt atggtgcaac ctcaattaat      720
gattttggaa tgttggcggt gagagtagtc aacgaattca cccagccag atcacatct       780 aaattgagag tgtacatgaa accaaagcat gttagggtgt ggtgtcctag accaccaagg      840
gtggtgccgt acttcggacc cggtgttgat tataaggata gtttgacacc gctttctaca      900
aaagcactca acacttat                                                   918

<210> SEQ ID NO 37
<211> LENGTH: 927
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 37
ggcttggaag acctcatcca acaagtggcc acgaatgcat tgagtctgtc gcagcccaca       60
agacccgcac ttccaccagc agaacaaagt gtgccaaaca ccagtcagac caccccagaa      120
cattcaaagg aagtacccgc actcactgca gtggagaccg tgcaaccaa cccattggaa       180 ccaggtgaca cagtgcaaac tagacatgtt gttcaaacaa gatcaaggag cgaaagtacg      240
gtggaatctt tctttgcaag aggggcgtgt gtcacgatta tggagttga caattacaat      300 gaaagcttga ccagtagtca aaaatccacc ctattcgcca cttggaatat tacatacact      360
gatacagtac agttgaggag aaaattggaa atgttcacct actccagatt tgacattgaa      420
tttaccttcg tagtaactga acgttactac tcgtcaaaca gtggccatgc cttgaatcag      480
```

-continued

```
gtgtatcaaa tcatgtatgt gccaccaggc gctccaattc ctaagaagtg ggatgattat    540
acctggcaaa catcatcaaa cccctcaata ttctacacct atggaacagc accacccaga    600
atttcgatcc cttttgtggg cattacaaac gcgtactcac attttatga cggatatgcg     660 actgtaccac tcaagacaga cactacggat ccggggggcgg ccttctatgg agcagtttcc   720
atcaatgact ttggtttgtt ggcggtgcga gttgtcaacg agcacaaccc ggtaagagtg    780
tcttcaaaga taagagtgta catgaagcct aaacatgtca gagtgtggtg cccacgacca    840
ccacgtgccg tggagtacta cggaccaggg gtagattaca aggcaaacac attgacacct   900
ctccctacca agaacttaac tacttat                                       927
```

<210> SEQ ID NO 38
<211> LENGTH: 888
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 38

```
ggtattgatg atatcataga taatgttgta accaatgctt tgaaggtgtc catgccacaa     60
gttcaagata cgcaatctag tggaccagtt aactcaaaag aagtacctgc attaacagct    120
gttgaaacag gggctactag tcaagttgac ccatcagacc taatagaaac tagacatgtt    180
attaataacc gcctcagatc tgagtgcaca atagaatcat tctttgggag gtcagcatgt    240
gtggccataa ttgggttatc taaccaaaaa ccccaccagtg acaatgcagc caagctcttt   300
gctacatgga agattagtta tcttgatatg tatcaattga aagaaaatt ggaattcttc     360 acatactcca gatttgatct tgagttaacc tttgtaattt cagaaagatt cttcacctca    420
acttcagctg ctgcaagaga ttatgtatac cagatcatgt acattccccc aggagcccct    480
atccctcagg tatgggatga ttacacatgg caatcatcca caaacccctc aatattctac   540
accacaggaa atgcatgccc tagagtgtcc atcccttttg ttgggatcgg tgcagcatac    600
tctcacttct atgatggatt ctctttagta ccttttcaata ccatcgatgc tggtgcttca   660
aacaggtacg ggtacaccac cataaatgat tttgggacta tggcaatcag gatagttaat    720
gaatacgacc cagtcacaat tgatgcaaaa gtcagggttt acatgaaacc aaagcatatt    780
aaggtgtggt gccccagacc tccacgggca gtagcataca atgggccaac agtgaatttt   840
aatgaaaacc cccatgtaat gacagcagtt gctgatatta gaacttat                888
```

<210> SEQ ID NO 39
<211> LENGTH: 909
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 39

```
ggtatcgaag atcttatcac cgaagttgca agcaacgctc tgaagttgtc acaaccaaaa     60
cccagcacac aacagagttt accaaacact agtagctcag aaccaactca ctctcaggaa    120
gcgccggcat tgaccgcagt agaaacagga gcaactagta gcgtagtacc agctgatctg    180
gtccagacgc ggcatgtgat acaaacacgt agccgaagtg agtctacagt tgagtcattc    240
tttgctcggg gggcgtgtgt aacaatcatg tcagtggaaa attacaatga aaccgctatc    300
gcagagtcca aattatttac caagtggaac attacctaca cagacacagt ccagttgaga    360
```

```
agaaaactag agatgttcac atactccaga tttgatattg agttcacatt tgtggtgact      420
gagcgttacc actccgcaaa ctcaggtcat gcactaaatc aagtttacca gatcatgtat      480
gttcctccag gtgcaccagt gccacaaaga tgggacgact acacatggca aacgtcatcc      540
aacccctcag tcttttatac ctatggtaca gcaccagcca gaatatcgat tccatatgta      600
ggcatagcca atgcctactc gcatttttat gatggcttcg ccaaagtgcc cattgaaggc      660
gagacgtcag atccaggtga tgcatactat ggtgcaacgt ccatcaatga tttcggcatc      720
ttagccatac gtgtggtcaa cgaacacaat ccagtgcaag tttcttccaa gattagagtg      780
tacatgaaac ctaaacatgt gcgcgtttgg tgtcccagac cacctagagc tgttccatac      840
tttggccccg gggttgatta taaggtgac gccctcacac cactatcacg caaggattta       900
accacctat                                                              909
```

`<210>` SEQ ID NO 40
`<211>` LENGTH: 888
`<212>` TYPE: DNA
`<213>` ORGANISM: Artificial Sequence
`<220>` FEATURE:
`<223>` OTHER INFORMATION: Description of Artificial Sequence; Note = synthetic construct

`<400>` SEQUENCE: 40

```
gggattgagg atacaatcga aaaagtggtt ggtgatgctc taagggtctc aatgccacaa       60
gttgccaaca cccagccatc aggacccgta aattctaagg aagttccagc actgacagca      120
gtggaaacag gtgcaaccag tcaagtcacc cctgaagatt tgatcgaaac caggcatgtt      180
attaacaata gactaagatc tgagtgcact gtggaggcct tctttggaag gtctgcatgt      240
gttgccatcc ttggtgtggt aaacaaaaag ccagacacca caaatgccaa agacctcttt      300
acaacatgga ggatcactta cctgcaaaac tatcaactga ggaggaaact cgaactcttc      360
acgtattcta gatttgattt ggaattaacg tttgtcatta cagaaagata cttttcaggg      420
acagcagcca caaccagaga ttatgtttac caaataatgt atgtaccacc aggagccccc      480
ataccaaata cctgggacga ctacacctgg cagtcatcta ccaacccctc tgtcttctac      540
accacaggca atgccagccc acgcatgtct atacccttg ttggtattgg tgccgcctat       600
gctcactttt atgacgggtt cagtgtggta ccattcaatc aaatagatgc aggagcatcc      660
aacaaatatg gctactcatc aatcaaagac tttggtacat tggcagttag aattgttaat      720
gagtttgatc cagtgacaat agaggctaaa gtcagagtg acatgaaacc caaacatgtc       780
agggtgtggt gtccaagacc acctcgtgca gtaccatatc aaaactcatc agttgatttc      840
gcccaaaacg cagtagcaat gaaccaagta gccacaatta ggacgtat                   888
```

`<210>` SEQ ID NO 41
`<211>` LENGTH: 915
`<212>` TYPE: DNA
`<213>` ORGANISM: Artificial Sequence
`<220>` FEATURE:
`<223>` OTHER INFORMATION: Description of Artificial Sequence; Note = synthetic construct

`<400>` SEQUENCE: 41

```
ggtatcgaag ataccattga cactgtcatt aacaatgccc tacaactatc tcaaccacag       60
ccaaataagc agttgacagc tcagtctacc cctccacaa gtggagtaaa ctcccaggag       120
gttccagctc tgaccgctgt ggaaaccggt gcctcggac aagcagtgcc cagtgatgtg       180
```

-continued

```
attgagacca gacacgtggt taattataag acccgatctg aatctactct tgagtctttc      240
tttggaaggt cagcttgtgt caccataatt gaggtcgaga acttcaatgc cactagtgaa      300
gcagacaaga ggaaacagtt caccacttgg ccaatcacat acaccaatac cgtgcaattg      360
cgcaggaaac tagaattctt cacttactcc aggtttgacc tagagatgac ctttgtagtg      420
acagaaagat attatgccag caacacaggt cacgccagaa accaagtgta tcaaataatg      480
tacattcctc ctggtgcacc acaacccaca gcatgggatg attacacgtg gcaaagctct      540
tcgaatccgt cagtctttta cacttatggg agtgctccac ccaggatgtc tataccgtat      600
gtcggtatcg caaatgcata ctctcttttt tatgatgggt tgcacgagt accactgaag       660 gacgaaacag cggactcagg tgatactttt tacgggctag tcaccatcaa tgattttgga      720 acccttagcaa taagagtagt gaatgaattt aacccagcta ggattacatc aaaaattaga    780
gtgtatatga aaccaaagca tgtaagatgc tggtgcccta gaccaccacg tgcagtgcca     840
taccgtggtg aaggagtaga ttttaattca agttcaatca caccactaac agcagtcgca    900
aacatcaaca cattc                                                      915
```

<210> SEQ ID NO 42
<211> LENGTH: 852
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 42

```
agcccagtgg aggaatccat tgagagaagc attggcagag ttgctgacac cattggtagt       60
ggaccatcca attcggaggc aataccggca ctcacagcag tagaaacagg acacacatca      120
caggttacac ctagtgacac gatgcaaaca agacatgtgc acaactacca ttcaaggtcc      180
gaatccagcg tagagaactt cctggcacgc tcggcttgtg tgttttatac aacatacacc      240
aacggtaaaa aaaaaaatgc cgccaaagag aagaagtttg caacgtggaa agtgagtgtt      300
agacaagccg cccaactaag aagaaagcta gagttattca catacttacg ctgtgacatc      360
gaattaacat tcgtcatcac cagtgcacaa gatccatcga ccgctaccaa cttggatgtg      420
ccagtgttga cccatcaaat aatgtacgtc ccacctggtg gtccagtccc tgaaaccgtg      480
gacgattaca actggcaaac atctacaaat cccagccttt tttggactga agggaatgca      540
cctccacgca tgtcaattcc attcatgagc ataggcaatg cctatagtat gttctatgat      600
ggttggtccg agtttaggca tgacggtgtg tacggcctga ataccttaa caatatgggc       660 acaatatatg ctaggcacgt caacgctgac aacccaggta gcatcaccag cacagtgaga     720
atatacttca aacccaaaca tgtcaaggca tggattcctc gcccgcctcg tttggcacag    780
tatcttaaag ccaataatgt gaattttgag atcaccgatg tgacagaaaa gagagatagt    840
ctcacgacca cg                                                         852
```

<210> SEQ ID NO 43
<211> LENGTH: 846
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 43

```
agcccagtgg agggcgccat agagagagcc attgcacggg tcgctgacac tatgccaagt       60
```

```
ggcccaacca attcagaagc agtgcctgcc ctgacagcag tggaaacggg ccacacctcc    120
caagtcgtcc ccagtgataa catgcaaacc aggcacgtga agaagtacca ttcacgctcc    180
gaaaccagcg tcgagaactt tctgtgtagg tctgcatgtg tatattttac cacatataag    240
aaccagacag gggcgaaaaa tagatttgct tcttgggtaa tcaccacaag acaagtggcc    300
cagctcagga gaaaactaga aatgtttacg tacttgcgtt tcgacattga actcacccttt   360 gtcattacaa gtgcgcaaga ccaatccact atttcccaag acgcccctgt gcagacacat    420
cagataatgt acgtgccacc gggaggccca gtgccaacca agttgacga gtatgtgtgg     480 caaacatcca ccaaccccag cgtcttttgg accgaggggta acgctccacc acgtatgtca   540 gttccctta tgagtatcgg taatgcttat agcacatttt atgacgggtg gtctgatttt     600
tcaaacaaag gaatatatgg gttgaacacc ttgaacaaca tgggaacatt gtacatccgc    660
cacgttaacg ggcccaaccc agtaccaatt accagcacag tgaggatata ctttaagccc    720
aagcatgtta aggcctgggt gcctaggcct ccaaggctt gccagtacaa aacgtttagg     780
caagtcaact ttacagtgac tggagtgacc gagagtaggg caaatataac caccatgaat    840
actaca                                                               846

<210> SEQ ID NO 44
<211> LENGTH: 852
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 44
ggtgatgtgc agaatgctgt cgaaggggct atggtcaggg tggcagatac agtgcaaact    60
tcagccacaa actcagagag ggtgcctaac ttgacagcag tagaaactgg tcacacttcg    120
caggtagtac ctggtgatac catgcagact agacatgtga tcaacaatca cgtgaggtca    180
gaatctacaa ttgagaactt ccttgccaga tcagcgtgtg ttttcttcct agagtacaag    240
acagggacca aagaggattc caatagcttc aacaattggg tgattacaac caggcgagtg    300
gctcaactac gtagaaaact ggaaatgttt acttacctac ggtttgacat ggaaatcacc    360
gtggtcatta caagctcgca agatcagtct acatcacaaa accagaatgc accagtgcta    420
acacaccaga taatgtatgt accaccaggg ggacccatac ccataagcgt ggatgattac    480
agctggcaaa catccaccaa ccccagtatc ttttggaccg aagggaacgc tccggcacgc    540
atgtcaattc catttattag cataggcaat gcgtatagta atttctacga tgggtggtct    600
cacttctccc agactggcgt gtatggcttc actactctga caacatggg tcaattgttc    660 ttccggcacg taaacaagcc caacccagcc gctattacaa gtgtggcgcg catttacttc    720
aaaccgaaac atgtacgcgc ttgggtgcct agaccaccgc gcttgtgtcc atacatcaat    780
agcacgaatg tcaactttga acccaagcca gtgactgaag tacgtaccaa cataataaca    840
acgggtgcct tc                                                        852

<210> SEQ ID NO 45
<211> LENGTH: 882
<212> TYPE: DNA
<213> ORGANISM: Artificial Sequence
<220> FEATURE:
<223> OTHER INFORMATION: Description of Artificial Sequence; Note =
      synthetic construct
```

<400> SEQUENCE: 45

```
ggagatgagg tgaagcatga acccacagtg gccaacacaa cagcaagtgg accatcaaat    60
tcacaacaag taccggcact cacagcagtg gagactgggc acacctcaca ggtggttcca   120
agcgatacca tacaaaccag acatgttcac aattaccata gtagaactga atccaccctg   180
gagaacttcc tcggaagatc agcatgcgtg cacattgact cgtataagac caagggagtg   240
accggcgaga gcacccggta cgcatcatgg gagatcacca ctcgcgagat ggtgcagctg   300
cggaggaagt gtgaactctt cacctacatg cgatatgatc tagaaatcac gtttgtgatt   360
acaagtcgcc aggagcaagg ggccaaactg tcgcagaaca tgccagtatt aacacatcag   420
atcatgtatg tcccaccggg cgggcctata ccaaccagca cgagagtta cgcttggcaa   480
acgtcaacga acccaagcgt gttttggaca gaaggaagct cgccaccacg aatgtcaata   540
ccgtttgtta gcataggaaa cgcatacagc aatttctatg atgggtggtc gcacttctca   600
caaaacggtg cgtatggtta cacggcacta acaagatgg gtaggatatt cgtgcgccat   660
gtaaacaaag agacaccact gcaagtcata agcacaatac ggatgtatat gaagcccaaa   720
cacgtgcggg cttgggtgcc aagaccacca cgcctgtgtc catacctgcg ggcgggtgat   780
ataaactttg aagtgactga tgttacagaa aaacgaaata acatcaatta tgtcccaacc   840
ccatcccaca gcagcagtgt gcacatgcgc ttgaacaacc at                       882
```

<210> SEQ ID NO 46
<211> LENGTH: 879
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 46

```
ggggacgtcg aagaggcaat tgatagggca gttgcgaggg tggctgacac aatgccaacc    60
ggtccacgaa acactgagag cgtgcctgcc ctgacagcag tagagacagg ccacacctca   120
caggtcgttc ctggtgacac aatgcagacg aggcatgtta agaactatca ctccaggaca   180
gagtcatcaa ttgaaaactt cctgtgcagg gctgcgtgcg tgtatataac aacatacaaa   240
tcagctggtg gaacacccac agagcgatat gcaagttgga ggataaacac caggcaaatg   300
gtgcagctca ggaggaaatt tgagctcttc acatacttgc gctttgacat ggaaatcaca   360
tttgtgatca caagcacaca agatcctggg acacaattgg cacaagatat gcctgtacta   420
actcatcagc tcatgtatat cccacctggg ggccctgttc ctaacagtgc cacagatttt   480
gcatggcaat catcaactaa tccaagtata ttttggacgg aaggctgtgc tccagcacga   540
atgtcggtgc cgttcatcag cattggcaat gcctacacca ttttttacga tgggtggtcg   600
catttcaccc aagaagggt tatgggtttt aactcactga caacatggg ccacatatat   660
gtgaggcacg tcaatgagca aagcctgggt gtctcgacca gcaccgttcg cgtgtatttt   720
aaacccaaac atgtgcgtgc ttgggtacca agaccaccca gactgtgccc atacactaag   780
agttcaaatg tgaatttcaa accgaccgct gtcactgatg agcgaaagga tatcaacgat   840
gtaggcaccc ttcgaccaac agtgtacact aaccttgtg                          879
```

<210> SEQ ID NO 47
<211> LENGTH: 843
<212> TYPE: DNA
<213> ORGANISM: Artificial Sequence
<220> FEATURE:

<223> OTHER INFORMATION: Description of Artificial Sequence; Note = synthetic construct

<400> SEQUENCE: 47

```
ggagacgtgc aagatgcagt gacaggtgct atagtacgtg tcgctgacac tctcccaaca      60
ggtccctcaa ataatgaagc tatacccaat ttaacagcag tggagactgg ccatacctcg     120
caagtgacac caggcgacac aatgcaaaca cgccatgtgg tgaacatgca cacccgctct     180
gagtcgtcca tcgagaattt cctggcacgt tcagcatgcg tgtactacct tgattaccaa     240
acgggagaag ggcccggcga tcagtatttt ggccagtgga ccattaccac gaggagggtt     300
gcgcaattgc gtcgaaagct ggagatgttc acttatctaa gatttgacat ggaaatcaca     360
atcgtgatta ctagttcaca ggatcaatct accatctcga acccagatac accagttttg     420
acgcaccaaa ttatgtatgt accaccagga ggaccaatcc cagcaaaagt cgatgattac     480
agttggcaaa catccacgaa tcccagcgta ttctggactg aagggaatgc gcctgcccgr     540
atatccatcc cattcattag cgttggaaat gcatacagta gcttttatga cgggtggtcg     600
aacttctcac aaaacgggcg gtatggctac aataccctca caacatggg acaattgttc     660
tttaggcacg ttaacaaacc cagccctaat actgtcacaa gcgtcgcccg catatacttc     720
aagcctaagc acgtgagagc ttggatcccg cgaccaccgc ggttgtgtcc atacataaat     780
gcgggagacg tgaacttcac tccgacacca gtgactgaaa agcgaaagga cctaataacc     840
acg                                                                   843
```

<210> SEQ ID NO 48
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 48

```
ggagatgtgc aggacgcagt ggctggggcc atagtgcgtg tggctaatac tctcccatca      60
ggcccctcaa acaatgaggc tatacccaac ttaacagccg tagaaactgg acacacctcg     120
caggtgacac cgggtgatac aatgcagacg cgccacgtag tgaacatgca cactcgttct     180
gagtcgtcaa tcgagaactt cctggcgcgg tcagcatgtg tatactacct cgattaccga     240
acaggaacgg ggcctggcaa tcaatacttt agccagtgga ctattaccac aagacgagtt     300
gcgcagctgc gtcgaaaatt ggagatgttc acctatctaa ggttcgacat ggagatcacg     360
attgtaataa cgagttcaca agatcagcct accgtccgaa acccagacac accggtcttg     420
acacaccaaa tcatgtatgt gccaccagga gggccaatcc cagcaaaggt cgacgattac     480
tgttggcaaa catccacaaa ccccagtgtc ttctggactg aagggaacgc accagcccgg     540
atatccatcc cgttcatcag tgtcgggaat gcatatagta gtttctacga tggatggtca     600
aatttctcgc aaaatgggcg gtatggctac aacaccctga caacatggg gcaattgttt     660
ttcaggcatg tcaataaacc cagtcccaac actgtcacaa gtgttgcccg catatacttc     720
aagcccaaac acgtgaaggc atgggtcccg cgaccaccgc gattgtgccc ttacattaat     780
gctggagatg taaatttcac ccccacatcg gtcactgaga agcgagcgag cctgataacc     840
aca                                                                   843
```

<210> SEQ ID NO 49
<211> LENGTH: 843

```
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 49
ggggacgtgc aagatgccgt gactggagcc atagtgcgtg tcgccgacac actgcacacg      60
ggaccctcga caacgaagc aatacccaat ttgacggccg tggaaacagg gcatacatcg     120
caagtgacac caggcgatac aatgcagacg cgtcacgtgg tcaacatgca cacccgttca    180
gagtcatcaa ttgagaactt cctagctcga tctgcgtgtg tgtattacct cgactatcaa    240
acagggtcag gacctggcac ccaatacttc ggccagtgga ccatctccac aaggagagtt    300
gcgcaactgc gccggaagtt ggaaatgttc acctacctaa gatttgacat ggaaataaca    360
atcgtgatca ccagttcgca agatcactcc accatctcaa atccagatac accaatcatg    420
acgcaccaaa ttatgtacgt accaccaggg ggtccaatcc cggcgaaggt cgacgactat    480
agctggcaaa catctacaaa ccctagtgta ttttggacag aagggaacgc acccgcccgc    540
atatccattc cattcattag tgtcggaaat gcctatagca gcttctacga cgggtggtca    600
aatttctcgc aaaacggccg atatggatac aacactttga caacatggg acaactattc     660
ttcagacacg tgaataagcc cagccccaac accttcacaa gtgttgcccg tgtatacttc    720
aagccaaaac acgtgaaggc gtggattcca cgaccaccgc gattatgtcc atacataaat    780
gcgggagacg tgaatttcaa accaacaccc gtgaccgaaa agagggcgag cttaatcacc    840
aca                                                                   843

<210> SEQ ID NO 50
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 50
ggagactcag agcacgcagt ggaaagcgcc gtatctaggg tggcagatac aattatgagt      60
ggcccgtcaa actcccaaca ggtccccgct cttactgcag ttgaaactgg acacacatcg    120
caagttgttc caagtgatac catccaaacc agacatgtgc agaatttcca ctctaggtcc    180
gagtcgacca ttgaaaattt cctgagtagg tcagcatgtg tgcatatcgc caattacaac    240
gcgaagggcg ataagacgga tgtggacagg tttgacaggt gggagatcaa cattcgtgaa    300
atggtgcaac tacgtaaaaa gtgtgagatg ttcacatatc tacgctatga tattgaagtt    360
acatttgtta taaccagcaa acaggatcag ggccccaaac taaaccagga tatgcctgtt    420
cttacccacc aaattatgta cgtaccccca ggaggttcag tacctagcac cgttgagagc    480
tatgcgtggc aaacatcaac aaaccctagc gtgttttgga ccgaggggaa cgctccagct    540
agaatgtcca tacccttttat cagcataggg aacgcttata gtagcttcta tgatggatgg    600
tcacactttta ctcaaaaagg ggtctacgga tacaacacat taaacaagat ggggcagcta    660
tttgtcagac atgtgaacaa acagaccccc acgccagtta ctagtaccat aagggtttac    720
ttcaaaccaa agcacattag agcttgggtc cctaggcccc cgcggttatg cccctatgtg    780
aacaagacaa atgtaaactt catcaccaca caggtaacag aacctacaaa tgacctcaat    840
gacgtgccca agtctgagca taacatgcac acatat                              876
```

<210> SEQ ID NO 51
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 51

```
aacgacgttc agaacgcggt ggaacggtca attgttcgtg tagcggacac attacccagt      60
gggccaagca actcagaaag cataccagca ctcacagcag ccgagactgg acatacctcg     120
caggtcgtcc ccagcgacac catccagacg cgacatgtga ggaattttca cgttcggtct     180
gagtcatcgg tagagaattt tcttagcagg tcagcttgcg tgtacatcgt ggagtacaaa     240
acccgggaca cgactcccga caagatgtat gatagctgga ttatcaatac caaacaagtg     300
gcgcagttga gaaggaagct ggagttcttt acctatgtca gattcgacgt ggaagttacc     360
tttgtcataa ccagcgtgca agatgactcc acaaaacgga acaccgacac cccagtgcta     420
actcatcaaa ttatgtatgt gccgccagga gggcccatac cacaagcggt ggacgattat     480
aactggcaaa cttccaccaa ccccagcgta ttttggactg aggggaacgc gccaccaagg     540
atgtctattc cgttcatgag tgttggcaat gcatacagta acttctacga cgggtggtcc     600
cacttttctc aaactggggt ttacgggttt aacacccctaa acaacatggg taagttatat     660
ttcaggcatg taaacgacag gactattagc ccaatcaaaa gtaaggtcag aatatatttc     720
aaacccaaac acgtgaaggc atgggtaccc agaccgccga gattgtgtga atacacccac     780
aaggataacg tggactatga accaaagggg gtcacaacat cacgcacttc aatcaccatc     840
accaactcca cacacatgga gacgcac                                          867
```

<210> SEQ ID NO 52
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 52

```
aatgacgttc aaaatgcagt cgagcaatca attgttcgtg tggctgacac gttacccagt      60
ggacccagta attcagagag cataccggca ctgacggccg ccgagactgg ccatacttct     120
caagttgtgc ccagtgatac tatacagaca cgccacgtaa aaaactttca tgtgaggtcg     180
gagtcgtcag tagagaactt tctcagtagg tccgcttgcg tgtatatagt gggatacaag     240
accacagatg cgacccctga caaaatgtat gacagctggg ttatcaacac aaggcaggtg     300
gcgcagctaa ggagaaaatt agagttcttc acctatgtta ggtttgatgt tgaggtcacc     360
tttgtgataa caagcgtgca agacgattca actgacgga acacagacac ccccgttcta     420
acccaccaaa tcatgtacgt accccaggt gggcccatcc cgcaggcagt ggacgactac     480
aattggcaaa cttccacaaa tcccagtgta ttttggacag aagggaatgc cccaccaaga     540
atgtccatac cattcatgag cgtaggtaac gcatacagca atttctatga tgggtggtct     600
cacttctctc aaactggggt gtacggtttc aacacccctga acaacatggg caagctatac     660
ttcaggcatg tgaacggcaa gacaataagc cctatcgcaa gcaaggttag gatttacttc     720
aaaccaaagc atgtgaaggc atgggtgccc agaccaccgc gattgtgtga atacacccac     780
aaggacaatg tggattacga accaagggga gtcacaacat cccgtacatc tatcacaatt     840
```
agcaattcca ctcatatgga aacatat 867

<210> SEQ ID NO 53
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 53
aacgacgttc agaacgcggt ggaacggtca attgttcgtg tagcggacac attacccagt 60
gggccaagca actcagaaag cataccagca ctcacagcag ctgagactgg acatacctcg 120
caggtcgtcc ccagcgacac catccagacg cgacatgtga agaattttca cgttcggtct 180
gagtcatcgg tagagaattt tcttagcagg tcagcttgcg tgtacatcgt ggagtacaaa 240
acccatgaca cgactcccga cgagatgtat gatagctgga ttatcaatac agacaagtg 300
gcgcagttga aaggaagct ggagttcttt acctatgtca gattcgacgt ggaagttacc 360
tttgtcataa ccagcgtgca agatgactcc acaagacaga acaccgacac cccagtgcta 420
actcatcaaa ttatgtatgt gccgccagga gggcccatac cacaagcggt ggacgattat 480
aactggcaaa cttccaccaa ccccagcgta ttttggactg aggggaacgc gccaccaagg 540
atgtctattc cgttcctgag tgttggcaat gcatacagca acttctacga cgggtggtcc 600
cacttttctc aaactggggt ttacgggttt aacacccctaa acaacatggg taagttatat 660
ttcaggcatg taaacgacag gactattagc ccaatcacaa gcaaggtcag aatatatttc 720
aaacccaaac acgtgaaggc atgggtaccc agaccgccga gattgtgtga gtacacccac 780
aaggataacg tggactatga accaaagggg gtcacaacat cacgcacttc aatcaccatc 840
accaactcca cacacatgga gacgcac 867

<210> SEQ ID NO 54
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 54
ggcgacaccg aaacggctat tgacaatgca atcgccaggg tagcagatac ggtggcgagc 60
ggtcctagta attcgaccag tatcccagca ctcacagcag ttgagacagg tcacacgtca 120
caagtcgagc ccagcgatac agtgcaaact agacatgtca aaaactacca ctcgcgttct 180
gagtcaaccg tggaaaactt tctaagtcgc tccgcttgtg tgtacatcga agagtactac 240
accaaggacc aagacaatgt taataggtac atgtcgtgga caataaatgc agaagaatg 300
gtgcaattga ggagaaagtt tgagctgttt acatacatga gatttgatat ggaaatcacg 360
tttgtaatca caagtagaca actacctggg actagcatag acaagatat gccgccactc 420
acccaccaga tcatgtacat accaccaggt ggcccggtac caaacagcgt aacagatttt 480
gcgtggcaga catcaacaaa ccccagtatt ttctggacag aaggaaacgc gccacctcgc 540
atgtctattc cattcatcag tattggcaat gcatatagca acttctatga cgggtggtca 600
cactttttccc aaaacggtgt gtacggatac aacgccctga caacatggg caagctgtac 660
gcacgtcatg ttaacaagga cacaccatac cagatgtcaa gcacaatccg agtgtatttc 720

```
aaacccaagc acatccgagt atgggtccca cggccgcctc gactgagccc gtacatcaaa    780
tcaagtaatg taaattttaa ccccacgaac ctgacggacg agcggtcatc catcacatat    840
gtgcccgaca ctatacgtcc agatgtgcgc accaac                              876
```

<210> SEQ ID NO 55
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 55

```
ggtgatgtcc agaatgcagt tgaggggggca atggttagag ttgcagatac cgtgagcact     60
agcgccacca actccgaaca agtgccgaac ctgaccgcgg tggagaccgg tcacacatcg    120
caggtagtgc ccggcgacac tatgcagacc aggcacgtag tgaacaagca tgtgcgatct    180
gaatctacaa ttgaaaattt cctcgcacgt tcagcctgtg tgtactttct tgagtacaag    240
actggtacca agactgactc caacgccttc agcaattggg tcatcacaac gcgcaaggtt    300
gcgcagctga ggcgcaagtt ggagatgttt acatacttaa ggtttgatat ggagattact    360
gtggtcatta ctagctccca agaccagtcc acatcacaaa atcaaaatgc gcccgtcctg    420
actcaccaga ttatgtatgt accacctggt ggcccagtgc ccactagcgt tgatgattat    480
tgctggcaaa catccacaaa cccaagcata ttttggacgg aaggaaacgc acctgccaga    540
atgtccatcc cctttatcag cattggaaat gcttatagca acttttatga tgggtggtca    600
catttctcac agaacggagt ctatggtttt accaccttaa acaacatggg ccagctgttt    660
tttaggcatg ttaacaagcc taacccggcg acaataacca gtgtggcccg catttacttc    720
aagccaaaac atgtgagggc ctgggtgcct agaccgccac ggttgtgccc ttacatcaac    780
agtagcaacg tgaacttcga cccaaaaacct gtggcagagg tcaggtctag catcatcacc    840
acc                                                                 843
```

<210> SEQ ID NO 56
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 56

```
ggtgatgtgg ttgaagccat tgagggcgca gttgctagag tagcagacac tatcagcagc     60
ggcccaacaa attctcaagc agtcccagca ctcacagcgg tggagactgg acacacctcg    120
caagttgtac caggtgatac catgcagacc agacacgtaa agaattacca ctcacgatca    180
gaatcgacca ttgaaaattt tctgagtagg gcggcttgtg tctacatggg tgagtattac    240 actacaaaata cagatgagac caagagattt gctaattgga caatcagcgc aaggcgcatg    300
gtacaaatga ggaggaagct tgaaatgttc acgtacgtcc gtttcgacgt ggaggtgaca    360
ttcgtaatta ccagcaaaca ggaccaaggg aatcggttgg acaagatat gccccgctc    420 acacaccaga taatgtacat cccgccaggt ggtcgtatac ccaaatccac cacagattac    480
gcatggcaaa cgtcgacaaa ccccagcatc ttttggacgg agggtaacgc gcccccagg    540 atgtccattc ctttcatgag cattggaaac gcatatagca atttttatga cggttggtct    600
cacttctctc aaaatggcgt gtacggatat aacacactaa accacatggg tcaattatac    660
```

| | |
|---|---|
| atgcgccatg taaatggacg atcacctctt ccaatgacca gcacggtgag ggtgtacttc | 720 |
| aaacccaaac atgtgaaaac atgggtgcca cgaccccccaa gattgtgcca atacaaaaac | 780 |
| gcctcgacag taaacttttc acccacaaac atcacagaca agagggatag catcacttac | 840 |
| attccagaca ccgtgaaacc cgacatgaca acatat | 876 |

<210> SEQ ID NO 57
<211> LENGTH: 861
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 57

| | |
|---|---|
| ggggatgaga gtgcaaaggc tacagtttcc aacacacagc ctagcggtcc aagtaattct | 60 |
| gtcagcgtgc caatgcttac tgctgctgag accgggcaca catctcaagc agtacccagt | 120 |
| gacactatac agaccaggtg cgtagtgaac caacacaagc ggtcggaatc atccgtggaa | 180 |
| aatttcctgt gtcgctccgc ttgcgtatac tacacaacct atgacactca cggggatgca | 240 |
| gccgacgcaa agtacgccag ttggacgata accacccgaa aagctgcaca gctgcggaga | 300 |
| aaactagaga tgttcacata cttgaggttt gatttagaag tgacattcgt tataacaagt | 360 |
| gcacaagtaa catctaccaa taaacgtcag gacacgcctg ttctcacgca tcaagtcatg | 420 |
| tacgtgccac caggtggtgc agtacccgct agtgtggacg attatgcgtg gcagacgtcc | 480 |
| acaaacccaa gtatcttctg gacggaaggg aatgcaccag cacgcatgtc tataccctttt | 540 |
| atcagcgtgg gcaacgcata cagtagcttc tatgatgggt ggtccaactt tacacagaat | 600 |
| ggagtttacg ggttcaacac gctaaacaac atgggaaagc tatacgtacg acacgtcaat | 660 |
| ggagctagcc ccggccctgt gaagagtacc atacggtttt acatgaagcc caaacacgtg | 720 |
| aaggcttgga tacccagacc tcctcgcctc tgcgagtacg aaaaatcagg caatgtaaac | 780 |
| ttcaaaccca agggcgtgac agagagccgg acgtctatca aattagaaaa accaaaccct | 840 |
| gcgtccaaat taatgaacca c | 861 |

<210> SEQ ID NO 58
<211> LENGTH: 894
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 58

| | |
|---|---|
| aatgatccag agcaagctat aaatcgggcg ctagcgaggg tggcagacac agttcgtagt | 60 |
| gggccgtcta actctgaaca aattcccgca ctgacagccg tggagacagg catacatca | 120 |
| caagtcgtcc ccagtgacac aatgcaaacc cggcatgtga agaattacca ctccaggtca | 180 |
| gagtcaacaa tagagaactt tttgtgtaga tcggcttgcg tgcacatcgc aacatacaag | 240 |
| gctaaaggcg gagctggaga cgtcgaccgg tacgacagct gggacataaa cataaaagag | 300 |
| ctggtacagt tgcgacgcaa gtgcgagatg tttacgtacc taaggtttga tatggaggtc | 360 |
| acctttgtga ttaccagcat acaggagcag ggcaaagcac tgacccagga catgccggtg | 420 |
| ctaacgcacc aaataatgta cgttccaccg ggcggtgccg tgcctagtgg tgcagaaagc | 480 |
| tttgcgtggc agtcatcaac gaatcccagt gtgttctgga cagaaggcaa tgcaccagca | 540 |

```
cgtatgtcta tacccttat aagtattggg aacgcttaca gtaatttcta tgatgggtgg    600
tcccacttta cccagaacgg tggttacggg tacaacacac taaacaaact gggtaagatc    660
tacgtcaggc atgtgaacaa acaaaccccc acggatgtca ccagcaccgt gcgaatttac    720
ttcaagccca aacacgtgcg agcttgggtg cctcgcccgc ctagactatg tccttataag    780
aacaaggcaa atgtaaactt tgaagttact agtgtaacca ctgccagaac gagtcttaat    840
gatgtcccca ctcccaacca cagtagtagc gtgcacctgc gcatgcacac gcac          894
```

<210> SEQ ID NO 59
<211> LENGTH: 882
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 59

```
ggtgatgacc aacacaagac caatacagtg acagacacag agcagagtgg cccgtcaaat     60
tccgaacgcg tcccagccct cacagcagtg gagactggcc acacttcgca ggtcgtaccc    120
agcgacacag tgcaaactcg ccacgtacgc aattaccact caaggacaga gtctaccta    180 gagaattttc ttggtaggtc agcatgtgtg cacatcgaca catacaaggc taagggtgaa    240
aaaggatctt ctgagaggta cgcgtcatgg gagataacta acagggagat ggtgcaattg    300
cgccgaaaat gtgagatgtt cacatatatg aggtatgacg tggaaataac atttgtgata    360
accagctacc aggagcaggg cacacgattg gcccaggaca tgcctgtact aacacaccaa    420
atcatgtacg tgcccccggg tgggcctgtg ccaacaagca cggagagcta tgcatggcag    480
acctcaacga accctagcgt cttttggact gagggcaacg caccaccgcg tatttccata    540
cccttcatca gcataggaaa tgcgtactgc aacttttatg atgggtggtc acatttctca    600
caagatgggt cctatggcta cacagcgctc aatagaatgg ggaaaatata tattagacat    660
gtaaataagg agaccccac acaggtcatt agtaccgtga ggatgtacat gaaaccaaaa    720
cacattcgcg catgggtgcc cagacccccc cggctgtgca aatacctaca ctcaggcaac    780
atgaacttca acgtggagga cattacagag gagcggaacg atataaacca tgtacccacc    840
cccagccaca gcagtagtgt gcgtgtgcgt cttggcacca ca                        882
```

<210> SEQ ID NO 60
<211> LENGTH: 867
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 60

```
ggtgatgttg aggactcagt aaacagagca gtggttaggg tagcagacac catgccaagt     60
ggaccatcca attcgcaggc agtacctgcc ttgacagccg ctgagacagg tcacacgtct    120
caagtggtgc ctggtgataa catccaaaca cgtcatgtgc acaactacca ctccagaact    180
gaatccagta tcgaaaattt cttcgggcgt ccgcatgtg tagtggtcaa acatataaa    240 atgggtcaaa aagttgtagc tacagacaga tatgatagtt ggatgatttc cattagggac    300
atggtacaac taagacggaa gtgtgaaatg ttcacgtaca tgagatttga tttagagatc    360
accttcgtgg tcacgagtta ccaacaatat agtacatcct tgacacagga catgccagtg    420
atcacgcatc agttcatgta tgtgccgcct ggggtccgg ttcctgagag tgtaaatagc    480
```

```
tacgcttggc aaacgtcaac caatcccagt atattctgga ctgagggtaa tgccccagca    540
aggatgtcca ttcccttcat cagtgttggg aacgcatata gctgcttcta cgatggctgg    600
tcacacttca cacagaaggg ggtttatggt tataacactc tcaacaacat gggcaaattg    660
tacatgcgac acgtgaacaa aaatagcccc acagagatca taagcactct tcgtgtgtat    720
ttcaagccaa agcacgtgaa agcgtgggta cccagaccac ccaggctatg tccatacaaa    780
tataaggcaa atgttgactt tgaagtgact ccaatcacag acaagcgaga ctccataacc    840
agcataccag tccccaagca cactcat                                        867
```

<210> SEQ ID NO 61
<211> LENGTH: 861
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 61

```
ggggataacc aggatcggac ggtcgccaac acacagccta gcggtccgtc caactccacg     60
gaaattccag ccttaacagc ggtggaaacg ggcacacct cacaagtgga tcccagtgac    120
actatccaga ccaggcacgt ggtaaacttc cactcacgtt ctgagtccac tatagaaaat    180
ttcatggggc gtgcagcatg tgtgttcatg gatcagtata aaatcaatgg agaagagacg    240
tccactgata ggttcgcagt gtggaccata aacataaggg agatggccca attaagaagg    300
aagtgtgaaa tgttcacgta catgcgtttt gatatcgaga tgacaatggt cattaccagc    360
tgtcaagacc agggaacgat actagatcag gacatgcctg ttttgacgca tcaaattatg    420
tacgtcccac caggggccc aatcccagcc aaagtagata gttacgagtg gcagacatca    480
acaaacccca gcgtcttctg gacggaaggt aatgcaccac cgcgtatgtc tattccattc    540
attagcgtcg gcaatgctta tagctcattt tacgatggtt ggtcacactt cacacaggac    600
ggtacctatg ggtatacaac ccttaatgca atggggaaac tgtacattag gcatgtgaat    660
aggagcagcc ctcatcagat aaccagcacg atcagagtat acttcaaacc caaacacatc    720
aaggcatggg tgccccgacc accacgattg tgcccgtata taacaaaag ggacgtaaac    780 tttgtagtca cggagataac agactcaagg acttccatca ctgataccacc acaccagaa    840 catagtgtcc tggcaacgca t                                              861
```

<210> SEQ ID NO 62
<211> LENGTH: 879
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 62

```
ggagacatcg tggaggctgt ggagggagcc atctcgcgag tggcagatac tgttagtagt     60
gggcccagta actctcaagc agtaccagcc ctcacagcag tcgaaacggg tcacacttct    120
caagtcaatc ctagtgacac catgcagacc agacacgtga caattacca ctcgcggtca    180 gaatccagca tagaaaattt ccttagccgc tctgcttgtg tgtatatggg cgaatacagc    240
acacaagcat cagatgagac caaaaagtac atgtcatgga ccataagccc aaggaggatg    300
gttcaaatgc gcaggaagtt tgagctcttc acttacctgc gttttgatgt ggagattact    360
```

```
tttgtaatca ccagcagaca agtcaaggta gggacacaat taggccaaga tgcccccccg    420
ctaactcacc aagtcatgta tatacccca ggaggcccag tacctgattc agttggtgat    480
tacgcatggc agacttccac taaccctagt atcttttgga ccgaaggtaa tgcatcaccc    540
aggatgtcaa taccctttcat tagcataggt aacgcctata gcaactttta tgacgggtgg   600
tcgcattttc accagaatgg cgtctatgga tacaacacgc tgaaccatat ggggcaactg    660
tacgtgcggc atgttaacgg cccttcacca ttaccagtga caagcacagt cagggtctac    720
tttaaaccca aacacgtgaa ggcttgggta ccgagggcac ccaggctatg tcaatatgta    780
aatgcatcca ctgtgaactt cgagccaaca gacatcactg agtcacgcac tgacatcaac    840
catgttccag acaccgtgaa gccagatctc caaacatac                           879
```

<210> SEQ ID NO 63
<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 63

```
ggggacgtgc acgatgcggt ggttggggcc atgacccgtg ttgcagacac gataagtagt     60
gggccaagca attcagaaag cgtgccagca ttgactgcag ccgagacagg acacacatca    120
caggtagtac cgagtgatac catgcagacc agacatgtgc ggaatttcca cacaagatca    180
gagtcttcaa tagaaaattt catgagtcgc tccgcctgtg tctactatac taagtataag    240
accaaagacc cggacccaac ggagatgtac tctagttgga aggttaccac caggcaagtg    300
gcacaactca ggaggaagat ggagatgttc acttatttgc gctttgacgt agaagtgaca    360
tttgtaataa ctagctcgca agatcagtcc acgagtgttg cacaggacgc acctgttctc    420
actcaccaaa tcatgtacat cccacccgga ggcccggttc ccaaatcagg tagggattac    480
tcatggcaat cctgtactaa cccaagtgtt ttctggactg agggtaatgc accaccacgc    540
atgtgtattc cgttcattag tattggaggg gcatatagtt cattctatga cgggtggtcc    600
cactttaacc aacaaggtcc gtacgggtat aacactctca atgacatggg tcaactgtat    660
tttaggcatg tgaacgaggg tagcccaggg gcggtaacaa gctacatcag aatatacttc    720
aaacctaaac atattagagc atgggtgccc agaccaccta gattgtgtca gtatgagaaa    780
caagggagcg ttgacttcaa ggtgcaggga gtaactgatg ctcgtacctc gctcaccact    840
aca                                                                  843
```

<210> SEQ ID NO 64
<211> LENGTH: 885
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 64

```
aatgacccag cacaagccgt gttgagtgcg atcggtcgtg tcgctgacac cgtcgctagc     60
gggccatcga attcagagag agttccagtt ctaaccgctg cggagacagg tcatacctca    120
caggtggttc ccagcgatac cattcagacg cgccacgtcg tcaacttcca cacaagatcg    180
gagtcaacaa ttgaaaattt tatgtgtcgc tccgcctgcg tgtacatcgc ccggtacggt    240
actgaaaagc aaggggaaca aatatccaga tacaccaagt ggaagatcac cactaggcag    300
```

```
gtggcgcaac tgcgcaggaa gatggagatg ttcacataca tgcgatttga tttggaaatg    360
acatttgtaa tcacaagctc ccagcgtatg tcaacggcat atgattcaga cacaccagcc    420
ctcacccacc aaataatgta cgtgccacct ggggcccgg agccccgtca ttatgaggat     480
ttcgcctggc agacatccac aaatccaagc atattttgga ccgaaggtaa cgcaccacca   540
cgcttatcaa tcccatttat gagtgtggga atgcctatt gcaattttta tgatgggtgg    600
tctcactttt cacaaagtgg agtgtatggg tttaccacct aaataacat gggacaactg    660 ttcatgcgcc atgtcaataa gtcaacagcg caccccattg atagtgtggt gcagtttat    720 tttaaaccaa agcatgttaa ggcgtgggtt ccaagacctc cccggttgtg cccatacatc   780
tatgcaagga acgtggattt tgagccacaa ggtgtcactg aatcaagaga aagataaca    840 ctagataggg atactcacac ccctatgcgc acatgcgggc cgttc                    885

<210> SEQ ID NO 65
<211> LENGTH: 882
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 65
ggagatgtct gtgaggaagt agagagggct attgtcaggg ttgcagatac tgtcggacgc     60
ggtcctgcta acactgagag tgtaccagcg ctgactgcag ttgaaactgg acacacttca    120
caagttgtac ccggggacac catgcaaacc agacatgtta aaaactttca cacgcggtca    180
gaatcatctg tggaaaattt catgtgcaga gcagcgtgtg tgtattatgt ggattaccac    240
acacaaaatg acagtgagga tgaaaaatat gcatcttgga ttatcaacac gagacaggta    300
gcacagctac gcaggaaaat tgagctgttc acatacacta ggtttgatgt cgaaatcaca    360
ttcgtgatca ccaccacaca gcagcaatcc acagctccca accccgacac tcctctgctg    420
acacaccaaa tcatgtatgt gccccccggt ggcccagtgc aaatagtgc taccgattat     480 tgttggcaat catccacaaa tcccagtata ttctggaccg agggtagcgc accacccaaa    540
atgtcaatac cctttataag tgtgggaaat gcatacagca gttttatga tgggtggtca     600 catttcactc aaaacggggt gtacgggttc aacactctga caatatggg caaattatac     660 ttcaggcacg taaatgacaa caccgtaggg ccatatgtga gcaaagcccg catttatttc    720
aaaccaaagc atgtgcgtgc gtgggttccc aaacctccca ggctctgtga atacaacaat    780
cgagccaacg tgaactttga accacgaggg gttaccgatg ccaggtctag tatcacggcc    840
acaaccgaca cgatcactga gagcacaggg atgcaaacga ct                        882

<210> SEQ ID NO 66
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 66
aatgatccag caactgccat agttagatcg gttgagagag tggctgatac catagcaagt    60
ggacccacta actcagagag agtgccagca ctaaccgccg ttgaaacagg tcacacctca    120
caggtagtcc cgagcgacac catgcaaact aggcatgttg tgaaccatca cattagatca    180
```

```
gagtcctcta ttgaaaactt cctgagcagg tccgcctgcg tgtacatcga catgtatggg      240
acaaaagaga atggtgacat caagcgcttc accaactgga gaataaacac acgtcaggtc      300
gtgcagctaa ggcgcaagct ggaaatgttt acatacatta gatttgatgt tgaaatcact      360
tttgtaatca ctagcacaca gggaacaccg actcaaaaga acaaggatac cccagttctt      420
acacaccaaa tcatgtatgt gccaccaggg ggcccaatcc ctgtatctta tgaagattat      480
tcttggcaga cctctacaaa tcctagtgtt ttctggacag aagggaatgc cccagcccgt      540
atgtcaattc ccttcatgag cgtagggaac gcctattgta acttttacga cgggtggtca      600
cacttctcac aatcgggtgt gtatgggttc actacactca ataacatggg tcagttgtac      660
tttcgacacg tgaacaagga caccttgga ccatacaata gcacggttcg ggtttacttc      720
aaacccaaac atgtgaaggc atgggtaccc agaccaccgc gcctgtgcga ctacgtttac      780
gcacataatg ttgacttcac accaaaaggg gttactgaca gcagggacaa gatcaccctg      840
gaccgtgatg aacacgtgcc gtcagtggtt aaccac                                876

<210> SEQ ID NO 67
<211> LENGTH: 870
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 67
ggagatgatc caccgcattc gatctcaaac acggttgcaa acaccaaccc tagtggtcca       60
accaactcag aaaggatccc agcgctcaca gcagcggaaa ctggtcacac ctcgcaggtg      120
gtcccgagtg ataccgtaca aactcgttgt gtgaaaaact tccacactcg atcggagtca      180
tcaattgaga acttttttgtg cagatcagct tgcgcacaca tgtcatcgta tgaggccttc      240
ccaacaacaa cacaagacgg tacacaaagg ttcgccaatt ggacgattag tgtgaaagac      300
atggtgcagt tgaggaggaa atgtgagatg ttcacgtact taagatttga catggaggtg      360 actttgtga taactagtgt gatcgaaact acaaaaggga aagtaccggc accagcagtc      420
acacaccaag taatgtacat tccaccaggc ggacctattc cagctagcgt tgaaagttat      480
gcctggcaaa catccaccaa cccaagcgtg ttttggacag aagggaatgc tccccacgc      540 atgtctatac catttatcgg cattggtaat gcctacagca tgttctatga cggatgggcc      600
agtttcagac aatcgggtgg atatggatac agcacccctga accacatggg ccagatattc      660
gtaagacacg tgaatgcaac cataccaaac ttgatcagca cagtcaggat atatttcaag      720
cccaagcacg ttagggcttg gattcctaga ccgcccaggg tgtgtcagta catttacaag      780
gcaaatgtag actacgcagt gtcaaatatc actgaaaagc gagatagtat aagatggaca      840
ccaacaaccg gtccgtcaat gacatcccac                                        870

<210> SEQ ID NO 68
<211> LENGTH: 855
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 68
ggtgacgacg caaggactgt tagcgacaca caaaagagcc agccatctaa ctctgagcaa       60
gtgcctgcct taacagcggt tgagactgga cacacctctc aagttgagcc cagtgataca      120
```

```
gtacagacac gacatgttgt caactcacac agtaggacag agtcgacaat tgagaatttc    180
tttgggaggg ctgcgtgtgt gagggtgaga gagtactcta tagggcatga tttggcagcg    240
gacgaaacat atgatagctg gccattaca gtgcgagaca tggtgcagct tcgtaggaag     300
tgtgagatgt tcacatacat gaggtttgac ttggaagtga cgctagtcat caccagctat    360
caagaaccag ggacaatcac cacccaggat atgcccgtcc taacccacca gattatgtat    420
gtgccgccag gaggcccggt cccagccaag gctgacagtt acgcgtggca aacgtcaaca    480
aatcccagta tattctggac cgaaggcaac gctccacctc ggatgtctat cccatacatt    540
ggcatcggca atgcatatag cagcttttat gacgggtggt cgagcttcaa caactcgggt    600
gtgtatggct acacaaccct gaataacatg ggtaaactgt acttcagaca cgtgaacaaa    660
cacagcccaa acactattaa gagcactgtg aggatatatt tcaagcccaa gcacgtccag    720
gcgtgggtcc caagaccacc gcgcttgtgc ccgtatctga ataagaggga tgtcaacttt    780
gaagtgcaac ccgttacgag caagagagac agtattaact gggtgccaca aacaaaccgc    840
caagtgtaca atcat                                                     855

<210> SEQ ID NO 69
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 69
aatgaaccta gtagtgccat tgagagagca attgtgcgcg tagcagatac tatggccagt     60
gggcctgcaa actcagagca aatccctgcc ctaaccgctg ctgagactgg tcacacctcg    120
caagtggttc ccagcgacac tatgcaaacc cgccatgtat gtaactacca caccagatct    180
gaatcatcga tcgagaactt cctatgcagg gctgcatgtg tctacatagt gagttacaaa    240
acacagggcg acgaacaaac cgacaaatac gctagttggg agatcaacac gcggcaggtg    300
gcacagttaa ggagaaaatt ggaattcttt acttacataa gatttgacat ggaggtaaca    360
tttgtgatca ctggttcaca agacaccagc acacagacta cacggatac gccagtgcta    420 acccatcaaa ttatgtatgt gcctcccggt ggtccagtac cgacatcagc cacagattac    480
agctggcaga catctacaaa tcccagtgtg ttctggacag aagggaatgc gcctccccgt    540
atgtccatac ccttcatgag cataggcaat gcgtatgcta atttctatga tgggtggtcg    600
cactttagcc agtcaggggt gtatggttac accacactca ataatatggg taccctgtat    660
ttcaggcacg tgaacaactc gaccatcggg ccttacacca gtgcagttag gatatatttc    720
aagccaaagc acgtcaaagc gtgggtgcca cgaccgccac ggttgtgcga ttacaaacac    780 aaaagaacg tagactttac tcccacaggt gtgaccacac tagagacaa gataaccttg    840 gacaagggga ctcacgtgcc gagcgtatgg aacaca                              876

<210> SEQ ID NO 70
<211> LENGTH: 876
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 70
```

```
aatgacccca aaggtgcact taataaagca gtgggcaggg tagctgatac tatagctagt    60
gggcccgtca atacagagca aattcctgca ttgacagcag tggagacagg gcatacatct   120
caagtggtac ctagtgacac aatgcaaacc cgacacgtgg tcaacttcca tactagatca   180
gagtcatcgt tacagaactt catggggaga gcggcatgtg tatatatcgc ccactatgcc   240
acagaaaagg ctaatgatga tttggacaga tacactaact gggagatcac aactaggcag   300
gtggcacagt tgaggcgcaa gttggagatg tttacgtata tgagatttga cctcgagatt   360
acattcgtaa tcaccagctc ccagcgtact tccaacaggt atgcgtcaga ctccccccca   420
ttaacacatc aaataatgta cgtgccgccg ggggtccaa ttcccaaggg ttatgaagac    480
tttgcctggc agacgtccac caacccaagt gtgttttgga ccgaaggtaa cgcccctcct   540
aggatgtcaa taccattcat gagcgttggc aacgcatatt gtaactttta tgatggatgg   600
tcccatttca gtcagagcgg tgtgtacggg tacactacat gaacaacat ggggcgctta    660
tattttagac atgtaaacaa atcaacagga tacccagtaa atagtgtcgc ccgcgtctat   720
ttcaagccca agcatgtgaa ggcatgggta cctcgcgcgc cacgcttatg tccatatttg   780
tatgctaaaa atgtcaactt tgatgtgcaa ggcgtgaccg agtcccgggg taagatcact   840
ctcgaccgtt cgactcacaa ccccgtgtta accact                              876
```

<210> SEQ ID NO 71
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 71

```
aatgaccctg aaggtgcgct caacaaggcg gtgggcagag tggctgatac aatagccagt    60
gggcccgtca acactgagca aattcccgca ttgacagcag tggaaacagg gcacacatct   120
caagtagtac ctagtgatac aatgcaaact cgacacgtgg tcaacttcca caccagatca   180
gaatcatcgt tggagaactt catgggaaga gcagcgtgtg tgtatatcgc tcattatgct   240
acagagaagg ctaatgatga tttagacaga taccaact gggaggtcac aaccaggcag    300
gtagcacagt tgaggcgtaa actggagatg ttcacgtaca tgaggtttga cctcgagatc   360
acatttgtaa tcaccagctc ccagcgcact tcaaccaagt atgcgtcaga ttccccccca   420
ctaacacacc agataatgta tgtaccgccg ggggcccga tccccaaggg ttatgaagat    480
tttgcctggc agacgtccac caacccaagt gtattttgga cggaaggtaa cgcccccct   540
aggatgtcga taccattcat gagcgttggt aacgcatact gcaacttta cgacggatgg   600
tcccatttca gccagagcgg tgtgtacggg tacactacat gaacaacat ggggcacttg    660
tatttcagac atgtaaacaa atcaactgca tacccagtta acagtgttgc ccgcgtctac   720
ttcaagccca agcacgtaaa ggcttgggtg cctcgcgcgc cacgcttatg tccatatttg   780
tatgcaaaaa atgtcaattt tgatgtacaa ggtgtgaccg agtctcgggg aaaaatcact   840
cttgatcgat cgactcacaa ccctgtgtca accacg                              876
```

<210> SEQ ID NO 72
<211> LENGTH: 877
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 72

```
aacgacccccg aacatgcgtt aaacaacgcc attggtagag tggcagatac gatcgccagt    60
gggccggtga actcggaacg catacctgca ctaaccgcag tggagacagg acacacgtct   120
caagtggtgc caagcgacac catgcaaaca aggcacgtag tcaacatgca tacaagatcc   180
gaatccacca tcgaaaattt catgggaagg gctgcttgtg tatacattgc caatacgcc    240
actgataagg ccagtgatga tctggacagg tacaccagct gggagatcac tacgagacag   300
gttgcgcaat tgaggagaaa gctggagctg tttacataca tgaggtatga cttagaagtt   360
acctttgtca ttaccagttc ccagcgcact tcgactacat atgcatcaga ctccccgcca   420
ttgacccacc aaattatgta tgtgcctccc gggggcccta ttcccatagg acacgaagac   480
ttcgcctggc agacttcaac aaaccccagt gtcttttgga ctgaaggaaa tgccccacca   540
cgtatgtcca taccattcat gagtgtgggc aatgcctact gcaattttta cgatgggtgg   600
tcacatttta accagagtgg ggtgtatgga tacactacac taaacaacat gggtcgctta   660
tatttcaggc atgtaaacag atctactgcc tacccagtta atagtgttgc acgtgtttac   720
tttaaaccca aacgtcaa agcctgggtc ccacgagcac cacgattgtg cccatacttg   780
tatgctaaga acgtgaactt taatgtgcaa ggtgtgactg actcccgaga caagataacc   840
gtagaccgaa ccaaccatgt acgtatgcgc accacag                             877
```

<210> SEQ ID NO 73
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 73

```
aacgacccccg aacacgtgtt aaacaatgcc gttggcagag tggcagatac aatcgccagc    60
gggccggtga actcggaacg cgtacctgca ctaactgcag tggagacagg catacgtct    120
caagtggtgc caagcgatac tatgcaaaca agacacgtag tcaacatgca cacaagatct   180
gaatccacta tcgaaaattt catgggaagg gctgcttgtg tatacatcgc acaatacgct   240
actgacaaag ccagtgacga tttggatagg tacaccagct gggaaatcac cacgagacag   300
gttgcgcaat tgaggagaaa gttggaaatg ttcacataca tgaggtatga cctggaagtc   360
acctttgtta tcaccagttc ccagcgcacc tcgactacat atgcatcaga ttccccacca   420
ttgactcatc agatcatgta cgtgcctccc gggggcccca ttcctatagg atacgaggac   480
ttcgcctggc aaacatcgac taaccctagt gtcttttgga ctgaaggaaa tgccccacca   540
cgcatgtcca ttccatttat gagtgtgggc aatgcctact gcaattttta cgatgggtgg   600
tcacacttta gccagagtgg ggtgtacgga tacactacac taataatat gggtcgtctg    660
tatttcaggc atgtaaacaa atctactgcg tacccggtta atagtgttgc acgtatttac   720
ttcaaaccca aacatgttaa agcctgggtc ccgcgagcac cacgactgtg cccatatttg   780
tatgcaagga acgtgaactt taatgtgcaa ggtgtgactg actcccgaga aaagataacc   840
atagaccgaa ccaaccatgt gcccatgcgt aacaca                              876
```

<210> SEQ ID NO 74
<211> LENGTH: 876
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 74

| | | | | | |
|---|---|---|---|---|---|
| ggggacacgg | aacatgcagt | tgagtcagct | atctccaggg | tagcagatac | cattagctca | 60 |
| ggtcctagta | acactgttgc | tataccagcg | ctcaccgcgg | cagaaacggg | ccacacatcg | 120 |
| caagtcaccc | ccagcgacaa | tcttcagacg | cgccatgtta | agaactatca | ctcccgctct | 180 |
| gagtcaacta | ttgaaaactt | cctgtgtaaa | tccgcgtgtg | tgcatattgc | gtcatacaac | 240 |
| gcatacggtg | atgttggatc | agacagtaga | tatgatagtt | gggagatcaa | catcagggaa | 300 |
| atggtgcagt | taaggaggaa | gtgcgaaatg | ttcacctatc | tcagatttga | catggaggtg | 360 |
| acatttgtca | tcactagcaa | gcaagatcaa | gggacttcgc | tatcacaaga | catgccagtg | 420 |
| ctaacacatc | agatcatgta | cgtgccgcca | ggcggatccg | tgcccactag | cgtccagagc | 480 |
| tacgcatgg | aaacatccac | caacccgagc | gtgttttgga | cagagggcaa | tgcccctgct | 540 |
| agaatgtcca | tcccattcat | tagcataggg | aatgcataca | gcagcttcta | cgacgggtgg | 600 |
| tcacatttca | cccaacaagg | tggctatggc | tataatacac | tgaacaagat | gggtaagttg | 660 |
| tttgtaaggc | atgtgaataa | agaaacacca | acccatgtga | cgagcacgat | acgtgtatat | 720 |
| tttaaaccaa | agcatgttag | agcgtgggtg | ccaaggccac | ctagattgtg | cccgtacatc | 780 |
| aataaagcgg | actgtaactt | cgctgttaca | ccactcacca | aacagcggtt | aggaatcaac | 840 |
| gatgtcccgc | ggcccagcca | cacattacat | actcat | | | 876 |

<210> SEQ ID NO 75
<211> LENGTH: 875
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 75

| | | | | | |
|---|---|---|---|---|---|
| aacgaccccg | caaccgctat | tgaaggagca | gtccggcgag | tggcggacac | gatccagagc | 60 |
| ggaccgagca | attcggagcg | ggttccagcg | ttaacggccg | ttgagacagg | tcacacagca | 120 |
| caggttaccc | cgagtgatac | aatgcaaact | agacatgtac | acaacttcca | caccagatcg | 180 |
| gagtctagca | tcgagaactt | cctcagtaga | gcagcttgtg | tgtacatagg | gaaatatagt | 240 |
| agcaatgcaa | caacacaaga | tgaacaatac | atgtcatgga | caattaatac | cagacagatg | 300 |
| gtgcagctga | gacgcaaatt | cgaaatgttc | acctacctac | gcttcgacgt | agaagtcact | 360 |
| tttataataa | catcgcacca | agatcaaggg | acacagttca | accaggatgc | gcccgtaatg | 420 |
| tgccaccaaa | tcatgtatgt | gccacctggt | ggcccggtgc | ctaagagtgt | tgatgacttc | 480 |
| acatggcaaa | cctctactaa | ccctagtgtc | ttttggtcag | aaggcaatgc | accaccgaga | 540 |
| atgaccattc | cattcattag | tatagggaac | gcctacagca | gctttatga | tggctggtca | 600 |
| cacttctctc | aaaatggggt | ttacgggttt | aatgcactca | ataacatggg | taaactgtat | 660 |
| gtgagacaag | tgaacctaaa | agcccctatg | ccagtcagca | gtacagttag | gatctatttc | 720 |
| aaacccaagc | atatcaaagc | ttgggtaccc | agaccaccgc | gtctatgtaa | gtacctgaag | 780 |
| tctgggagtg | tcaattttga | gcccactgat | ttgacagaaa | aacggaaatc | cagaaagtac | 840 |
| atcccaaaaa | ctttcagacc | agatgtgaga | accat | | | 875 |

<210> SEQ ID NO 76

<211> LENGTH: 843
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 76

| | | | | | |
|---|---|---|---|---|---|
| ggtgatgtgc | atgatgcagt | tgtgggtgcg | atgtcgcgcg | tcgctgatac | agtagcaagt | 60 |
| ggccctgcaa | actctgagag | cgtgcctgct | ctcactgcgg | tagaaactgg | acacacgtca | 120 |
| caggtgacac | caagtgatac | aatgcagacc | agacacgtac | acaacttcca | cacacggtcc | 180 |
| gaatcgtcaa | tcgagaactt | cttaagccgc | tctgcatgtg | tctattatgc | aacgtacaaa | 240 |
| acaacagcca | gcagacccga | agaccaattc | gttaggtggt | ccatttcata | ccgccaggtg | 300 |
| gcccaactgc | gcaggaaaat | ggaaatgttc | acctacctgc | gctacgatgt | ggaggtcact | 360 |
| tttgtgatta | caagttctca | ggacccatcg | accaacgtaa | gccaggatgc | tcctgtactc | 420 |
| acacatcagt | taatgtacgt | accccccggg | ggtccagtgc | ccaaaaattc | aagagactat | 480 |
| gcatggcaaa | catccaccaa | cccgagtgtg | ttctggaccg | aggggaacgc | accaccaagg | 540 |
| atatccatcc | cctttatcag | tgtgggcaac | gcatacagtt | gcttttatga | tggatggtcc | 600 |
| cactactcac | agacgggggt | gtatggttac | aacaccttaa | acgacatggg | ccaattattt | 660 |
| gtcaggcacg | tgaatgaggc | aagcccgggt | gcggtgtcaa | gtgtagttag | gatttacttc | 720 |
| aaacccaaac | atgtgaaggc | atgggtcccg | agaccaccac | ggttgtgcca | atatgttaac | 780 |
| gcagcaacgg | tgaacttcac | tcctgaaggg | gtcactaagg | cacgtactga | tctcatgaca | 840 |
| aca | | | | | | 843 |

<210> SEQ ID NO 77
<211> LENGTH: 915
<212> TYPE: DNA
<213> ORGANISM: Artificial Sequence
<220> FEATURE:
<223> OTHER INFORMATION: Description of Artificial Sequence; Note = synthetic construct

<400> SEQUENCE: 77

| | | | | | |
|---|---|---|---|---|---|
| ggaatagaag | aaactattga | cacagtgatc | accaacgctt | tacaactgtc | tcagcccaaa | 60 |
| ccgcagaaac | aactcactgc | tcaatccacc | gcctcatcca | gcggagtcaa | ttcacaagaa | 120 |
| gtgccagcat | tgactgctgt | ggagacggga | gcttctggtc | aagccatacc | cagcgacgtg | 180 |
| attgagacca | gacatgtcgt | caattacaaa | actagatctg | aatcaaccct | tgagtcattc | 240 |
| tttggtagat | cagcatgcgt | aaccatactg | gaagtagaga | acttcaatgc | cactaccgaa | 300 |
| tcggacaaga | aaaagcaatt | caccaccctgg | ccaatcacat | acaccaacac | agtccagttg | 360 |
| cgcaggaaat | tggaattctt | tacatactcc | agatttgatc | tggaaatgac | ttttgtcata | 420 |
| actgagaggt | accacacaag | taatacagga | catgctagaa | tcaagtgta | ccaaataatg | 480 |
| tacataccac | cgggtgcgcc | aaggcccaca | gcacgggatg | attacacctg | caaagttca | 540 |
| tccaatccat | cagtgtttta | cacatatggt | agcgcgcctc | ccagaatgtc | tatcccatat | 600 |
| gttggcattg | ccaatgcata | ctcacacttt | tatgacgggt | tgcccgagt | tccctgaaa | 660 |
| gatgatacaa | ctgactccgg | tgacactttt | tatggattgg | tcaccatcaa | tgactttgga | 720 |
| acattggctg | tgagggtggt | gaatgagttc | aaccctgcaa | ggataacatc | aaaggtcaga | 780 |
| gtttatatga | agcccaaaca | tgtgaggtgt | tggtgtccta | ggccaccgcg | cgcagtgccc | 840 |
| tatcgtggtg | aaggggttga | tttcaaacaa | gattcaatca | cgccaataac | agcagtcacc | 900 |

```
aatattaata ccttc                                              915

<210> SEQ ID NO 78
<211> LENGTH: 936
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 78
tcaaaccact tacatggagc agaggcagcc tatcaggtgg agagtatcat caaaacagca    60
actgatactg tgaagagtga gattaacgcc gaacttggtg tggtccctag tctaaatgca   120
gttgaaactg gtgcaacttc caacactgaa ccagaagaag ccatacaaac tcgcacagta   180
ataaatcagc atggtgtgtc ggagacgtta gtggagaatt ttcttggtag ggcagcccta   240
gtgtcaaaga aaagttttga atacaagaat catgcctcat ccagcgcagg gacacacaaa   300 aacttttta aatggacaat taatactaag tcttttgtcc agttaagaag aaagctggaa    360
ttattcacat accttaggtt tgatgctgaa atcaccatac tcacaactgt ggcagtaaat   420
ggtaataatg acagcacata catgggtctc cctgacttga cactccaagc aatgtttgta   480
ccaactggtg ctcttactcc aaaggagcag gattcatttc attggcaatc aggcagtaat   540
gctagtgtgt tctttaaaat ttctgatccc ccagctagaa tgactatacc ttttatgtgc   600
atcaactcag catattcagt tttttatgat ggctttgctg gatttgagaa aaatggtcta   660
tatggaataa acccagctga cactattggc aacttgtgtg tcagaatagt gaatgaacat   720
caaccagttg gttttacagt gaccgttagg gtttacatga agcctaaaca tataaaagca   780
tgggctccac gaccaccgcg aaccatgcca tacatgagca ttgctaatgc aaattacaaa   840
ggtagagata cagcaccaaa cacacttaat gccataattg gtaatagagc gagtgtcaca   900
actatgcctc acaacatagt aaccaccggt ccgggt                             936

<210> SEQ ID NO 79
<211> LENGTH: 861
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 79
aatgaccagc acaatggggc gatcgttgcc aacacaacag ctagcggacc ttctaattcg    60
gaaagcatac cggcacttac tgcggctgag actggccaca catcgcaggt tgtccctagc   120
gacaccatcc agacaagaca tgtgaaaaac taccactcgc gttcagagtc caccatagag   180
aacttcctgt gtagatctgc ctgtgtgtac tacaccacgt acaacactca gggcgagcaa   240
gcacatgata aatacgcaag ttggccaatc acgactgaaa agttgcccca actgcgcagg   300
aagctggagt tctttaccta cctgcggttt gatctcgaga tcacgttcgt gatcacgagc   360
gcccagatca catccacgaa ccaaaaccag gatgccccag tactcacaca tcaggtgatg   420
tatgtacccc caggggggt ggtaccgcgc agtgtggatg actatagttg gcagacttcc   480
accaatccca gcatcttctg gacagaaggg aacgcacctc ctcgtatgtc aataccattc   540
attagtgtgg gcaacgccta cagcagcttt tacgacgggt ggtcacactt tgaacaaacc   600
ggggtatatg gattcaatac ccttaataat atggggactt gtacgccag gcacgttaac   660
```

```
ggtgctagtc ccgggccagt caagagcacc attaggatat atatgaaacc taaacatgtg    720
aaagcgtgga tacctaggcc cccacggttg tgcgactatg tgaaatctgg caacgtcaac    780
tttgaaccaa aaggagtcac cgagagcaga ccatctataa agttagaaaa gacctcaagt    840
gggcacaggc tgacaaccca c                                               861

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 80

Met Tyr Val Pro Pro Gly Gly
1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 81

Met Tyr Xaa Pro Xaa Gly Ala
1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 82

Phe Gly Xaa Gln Ser Gly Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa  = any amino acid

<400> SEQUENCE: 83

Thr Ala Xaa Glu Thr Gly His
1               5

<210> SEQ ID NO 84
<211> LENGTH: 7
```

-continued

```
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 84

Thr Ala Val Glu Thr Gly Xaa
 1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 85

Gln Ala Ala Glu Thr Gly Ala
 1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence; Note =
      synthetic construct
<220> FEATURE:
<221> NAME/KEY: VARIANT
<222> LOCATION: (0)...(0)
<223> OTHER INFORMATION: Xaa = any amino acid

<400> SEQUENCE: 86

Met Xaa Xaa Pro Pro Gly Xaa
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 87

Met Tyr Val Pro Pro Gly
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence; Note =
      synthetic construct

<400> SEQUENCE: 88

Met Phe Val Pro Pro Gly
 1               5

<210> SEQ ID NO 89
<211> LENGTH: 6
<212> TYPE: PRT
```

-continued

```
<213> ORGANISM: Artificial Sequence
<220> FEATURE:
<223> OTHER INFORMATION: Description of Artificial Sequence; Note =
      synthetic construct

<400> SEQUENCE: 89

Met Tyr Val Pro Thr Gly
 1               5
```

TYPING OF HUMAN ENTEROVIRUSES

The application is a divisional of U.S. application Ser. No. 09/937,862, filed on Sep. 28, 2001, U.S. Pat. No. 6,846,621, which is the National Stage of International Application No. PCT/US00/07828, filed on Mar. 24, 2000, which claims the benefit under 35 U.S.C. § 119(e) of U.S. Provisional Application 60/127,464, filed on Mar. 31, 1999.

FIELD OF THE INVENTION

The present invention relates to methods of detecting the presence, and of establishing the serotype, or serovar, of an enterovirus that may be present in a clinical sample or a biological sample, as well as to a kit that includes primers that may be used in the methods. The methods include amplification of viral RNA, and sequencing of the resulting amplicons.

BACKGROUND OF THE INVENTION

Enteroviruses constitute a broad range of pathogens etiologically responsible for a wide range of diseases in humans, as well as in other animals. The genus *Enterovirus* is a member of the family Picornaviridae. As the family name indicates, enteroviruses are small RNA viruses; they contain positive single stranded RNA as the genome. Five groups are found within. the enteroviruses: coxsackievirus A (CA), coxsackievirus B (CB), echovirus (E), and numbered enteroviruses (EV), as well as poliovirus (PV). There are 66 serotypes currently classified among the human enteroviruses, although two serotypes, E22 and E23, are to be reclassified in a different genus.

The viral genome is shown schematically in FIG. 1. The single stranded RNA comprises a 5' nontranslated region (single line), which is followed by an open reading frame coding for a polyprotein precursor of Mr $240\text{-}250\times10^3$ Da (boxed portion), followed by a 3' noncoding sequence and a poly (A) tract (single line). In the polyprotein, the sequence of gene products begins 1A, 1B, 1C, 1D, and 2A. 1A through 1D are, respectively, the structural proteins VP4, VP2, VP3, and VP1 of the viral capsid; VP1 is followed in the open reading frame by a nonstructural protein 2A.

The various members of the human enteroviruses cause a wide range of symptoms, syndromes and diseases. These include acute benign pericarditis, acute flaccid paralysis, acute hemorrhagic conjunctivitis, aseptic meningitis, various exanthemas, carditis, croup, encephalitis, enanthema, gastrointestinal disease, hepatitis, hand-foot-and-mouth disease, various respiratory diseases, myocarditis, neonatal disease including multi-organ failure, pericarditis, pleurodynia, rash, and undifferentiated fever. In general, the syndromes are not correlated with particular enterovirus serotypes, nor does a serotype specifically correlate with a particular disease, although in certain cases serotypes do correlate with particular diseases.

Enteroviruses are responsible for large numbers of infections. There may be between 30 million to 50 million illnesses that are ascribable to enteroviruses each year in the United States (CDC; MMWR 46:748-750; Strikas et al. J. Infect. Dis. 146:346-351 (1986); Rotbart in Human Enterovirus Infections, H. A. Rotbart (ed.) ASM Press, Washington, D.C., pp. 401-418 (1995)). After rhinoviruses, enteroviruses are the most common viral infection in humans. Enteroviral infections lead to 30,000 to 50,000 hospitalizations each year for aseptic meningitis, myocarditis, encephalitis, acute hemorrhagic conjunctivitis, nonspecific febrile illnesses, and upper respiratory infections (Melnick, Biologicals 21:305-309 (1993); Morens et al. in Human Enterovirus Infections, H. A. Rotbart (ed.) ASM Press, Washington, D.C., pp. 3-23 (1995); Melnick in Fields Virology (B. N. Fields et al. (eds.) 3rd ed., Lippincott-Raven Publishers, Philadelphia, pp. 655-712 (1996)). Enteroviruses are also implicated in acute flaccid paralysis in animal models, as well as in dilated cardiomyopathy. The six serotypes of coxsackie B viruses are implicated in a variety of clinical diseases, such as meningitis, myocarditis and severe neonatal disease. Recently, enterovirus infection has been linked to chronic fatigue syndrome (Clements et al., J. Med. Virol. 45:156-161 (1995)).

Poliovirus is also an enterovirus that infects humans. Three serotypes, PV1, PV2, and PV3 are known. A nonenteroviral picornavirus that also afflicts humans is human rhinovirus (HRV), responsible for many common cold infections; several serotypes have been identified. Additionally, picornaviruses affect mammals other than humans, including viruses such as bovine enterovirus (BEV) and simian picornavirus (SPV).

It is important to identify the serotype of an enterovirus infection in a subject. Knowledge of the serotype can provide useful guidance to a physician in determining a course of treatment of the disease in the subject. For example, the appropriately identified immune globulin having a sufficient titer may be administered to immunocompromised patients. Furthermore, an antiviral drug such as Pleconaril (Viropharma) may differ in its relative efficacy against different serotypes. Additionally, an understanding of the geographic and chronological development of an enterovirus infection in a population can influence preventive measures among the members of the population to minimize the spread of the disease. Furthermore, it is useful from a broader perspective to track the incidence and distribution of an enterovirus disease from an epidemiological point of view. In earlier practice, it was found that the various serotypes could be grown in different cell culture hosts, and in different animal model hosts. In the animal hosts, furthermore, different symptomology also provided typing information. These classical assays provide ways of distinguishing the serotypes. Nevertheless, some enterovirus serotypes, especially in the coxsackievirus A group, do not grow in cell culture. It has been observed that 25% to 35% of patient specimens are not identified by cell culture for a variety of reasons (Rotbart, 1995). Furthermore, such culturing and classification procedures are costly, time-consuming, subject to experimental variation, and not amenable to repetitive or extensive application in the field.

The serotypes of non-polio enteroviruses have been identified during the past several decades using classical immunological neutralization assays based on a panel of specific antibodies. Application of such a determination to a clinical sample is generally impractical and inconvenient. Although a number of neutralization sites have been localized to the VP1 protein of enteroviral particles, the exact identity of the epitopes responsible for serotype specificity remain unknown; VP2 and VP3 may also contain specific neutralizing epitopes. Serotyping has generally been carried out using intersecting pools of antisera, the Lim and Benyesh-Melnick (LBM) pools, which were originally defined in 1960 (Lim et al., J. Immunol. 84:309-317 (1960)). The antiserum pools currently distributed by the World Health Organization cover 42 serotypes in 8 pools (Melnick et al., Bull. WHO 48:263-268 (1973)). Analysis of the neutralization pattern affords an identification of serotype. (See Rotbart, 1995). Clearly, this is a cumbersome and painstaking process. Additionally, the supply of the antisera is limited or difficult to maintain. Problems in serotyping more recent isolates have been ascribed to pronounced intratypic antigenic variation (Melnick, Enteroviruses: polioviruses, coxsackie viruses, echoviruses, and newer enteroviruses. In Fields Virology (Fields et al., (Eds.) 3rd Ed., Lippincott-Raven Publishers, Philadelphia, 1996, pp. 655-712; Melnick et al., Bull. W.H.O. 63:453-550 (1985); Wigand et al., Arch. Ges. Virusforsch. 12:29-41 (1962); Wenner et al., Am J. Epidemiol. 85:240-249 (1967); Duncan, Arch. Ges. Virusforsch. 25:93-104 (1968)). This has been explained by pointing out that enteroviruses, being RNA viruses, undergo spontaneous mutation at a very high rate. This can lead to antigen drift, with the potential of producing antigenic variants such that a neutralization assay would produce a false negative result. For example, escape mutants in picomaviruses are discussed in detail in Mateu (Virus Res. 38:1-24 (1995)). For all these reasons there is a need to supplant neutralization assays for serotyping non-polio enteroviruses.

More recently assays based on nucleic acid detection have been developed. Probe hybridization assays directed either to RNA or to cDNA have been used to detect non-polio enteroviruses (Rotbart et al., Mol. Cell. Probes 2:65-73 (1988); Rotbart, J. Clin. Microbiol. 28:438-442 (1990); Chapman et al., J. Clin. Microbiol. 28: 843-850 (1990); Hyypia et al., J. Gen. Virol. 70:3261-3268 (1989); Olive et al. J. Gen. Virol. 71:2141-2147 (1990); Gilmaker et al., J. Med. Virol. 38:54-61 (1992); Yang et al., Virus Res. 24:277-296 (1992); Zoll et al., J. Clin. Microbiol. 30:160-165 (1992); Muir et al., J. Clin. Micro. 31:31-38 (1993); Drebot et al., J. Med. Virol. 44:340-347 (1994); Rotbart et al., J. Clin. Microbiol. 32:2590-2592 (1994)). In the absence of nucleic acid sequence information for the non-polio enteroviruses, most of these probes have targeted the highly conserved 5' non-coding region of the viral genomes. Additionally, RNA probes directed to the VP1 capsid gene have been used on a limited basis to identify some of the CBs and a few closely related CAs (Cova et al., J. Med. Virol. 24:11-18 (1988); Alksnis et al., Mol. Cell. Probes 3:103-108 (1989); Petitjean et al., J. Clin. Microbiol. 28:307-3 11 (1990)). More recently, oligonucleotides having sequences based on the VP4-VP2 junction have been applied as diagnostic and epidemiologic tools (Drebot et al., J. Med. Virol. 44:340-347 (1994); Arola et al., J. Clin. Microbiol. 34:313-318 (1996); Kim et al., Arch. Virol. 142:853-860 (1997); Oberste et al., Virus Res. 58:35-43 (1998)). The sequences in these regions, however, do not always correlate with serotype (Kopecka et al., Virus Res. 38:125-136 (1995); Arola et at., J. Clin. Microbiol. 34:313-318 (1996)). Furthermore, sequences of only certain prototypes were available with which to compare and classify clinical samples (Arola et al., (1996)). A generic probe-based assay for nucleic acids in the presence of chaotropic agents is described in U.S. Pat. No. 5,726,012. An assay for a target nucleic acid sequence wherein two separate probes are hybridized to the same strand of a nucleic acid, and then joined, for example by a polymerase activity, is disclosed in U.S. Pat. No. 5,516,641.

Reverse transcription (RT) coupled with the polymerase chain reaction (PCR) (RT-PCR) has been developed using enterovirus universal primers or broadly selective primers. Such primers are intended to amplify nucleotide regions from a large number of enterovirus serotypes in one diagnosis. One set of primers (Rotbart, J. Clin. Microbiol. 28:438-442 (1990)) has been reported to amplify 60 of the 66 serotypes tested. (Among the nonreactive serotypes, two are atypical enteroviruses and may be reclassified.) A comparison of sequence identities of the various sets of universal primers with serotype sequences is given in Rotbart et al. (1995). Many of the universal primer sets are designed to amplify regions of the 5' untranslated region of the genome (see, for example, Drebot et al. (1994); Diedrich et al., J. Med. Virol. 46:148-152 (1995); Arola et al. (1996); Bailly et al., Virology 215:83-96 (1996); and U.S. Pat. No. 5,075,212 to Rotbart). A comparison of base sequences in coxsackievirus B5 was reported for isolates from three different outbreaks of disease, based on amplicons obtained using primers in the VP1/2A region of the genome (Kopecka et al., (1995)). Variations in sequence occurred even within the same outbreak, and somewhat greater variations were found among isolates from the different outbreaks, and between serotypes. International application WO 98/14611 discloses degenerate primers directed to the VP1 gene, which, when used in certain defined pairs, provide PCR amplification of enterovirus nucleic acids. Use of the specific primer pairs permits ascertaining whether a sample belongs to an enterovirus serotype, or to a small group of cognate serotypes, based on correlation of the pattern of the presence or absence of an amplicon with priming by the various primer pairs. This method does not rely on obtaining nucleotide sequences for accomplishing the serotyping.

Oberste et al. developed a database of homologous sequences for a portion of the VP2 gene of all 66 human enterovirus serotypes (Virus Res. 58:35-45 (1998a)). They found that the sequences of many antigenic variants failed to cluster with their respective prototype strains as determined by serotyping. This finding suggested that the portion of VP2 examined may not prove to be useful for consistent molecular inference of serotype.

According to Holland et al. (J. Clin. Microbiol. 36:1588-1594 (1998)) neither cell culture growth, nor PCR can successfully type enterovirus infections. They report an alternative typing protocol based on polyacrylamide gel electrophoretic fingerprinting of whole virus radiolabeled proteins. However, the database of viral protein profiles contains data for less than one-third of the known EV serotypes. Therefore its general applicability remains unknown.

In the case of poliovirus, U.S. Pat. Nos. 5,585,477 and 5,691,134 to Kilpatrick disclose methods and oligonucleotide primers that are specific and sensitive for detecting all genotypes of poliovirus, as well as primers that are specific and sensitive for distinguishing the three serotypes of poliovirus, and methods for detecting poliovirus and/or distinguishing among the serotypes based on the use of the disclosed primers. Additionally WO 98/14611 discloses an extensive set of degenerate oligonucleotide primers for use in detecting the presence or absence of a non-polio enterovirus in a sample and to identify non-polio enterovirus serotypes. The primers are combined in pairs that detect various groupings of serotypes, and several amplification procedures are carried out in order to detect the presence ef or absence of an amplicon in each case. A pooled grid of the results provides information useful in typing a non-polio enterovirus in a sample.

In summary, immunological methods for serotyping enteroviral infections are cumbersome and time consuming. They rely on an antigen-antibody reaction between antiserum pools established more than two decades ago, and whose supply may become limited. As explained, for example in Mateu (1995), antigen drift among RNA viruses such as the enteroviruses leads to a high probability that escape mutants will arise, and thereby escape not only serotyping, but perhaps detection as well. A second classical approach, cell culture couple, with whole animal host growth and use of antisera for typing, is extremely cumbersome, expensive, and labor-intensive. Modern molecular biological methods similarly have important deficiencies as currently implemented. Probe assays generally tend to lack sensitivity. Furthermore, a probe directed to a conserved region, such as the 5' noncoding region of the non-polio enteroviruses, lacks specificity, and so cannot be readily applied in typing a viral infection. RT-PCR has been implemented as a generic enteroviral diagnostic assay. In general, these assays fail to implement serotype-specific detection, so that typing is not currently available using RT-PCR. Holland et al. (1998) state that all typing methods in use or then currently under development are limited by virtue of the large number of different enteroviral serotypes, and as a consequence, the need for virus-specific reagents that would discriminate among them.

For these reasons, there remains a need for a typing procedure that avoids the necessity of infecting live animals, animal tissue homogenates, or cell cultures. There further remains a need to implement a nucleic acid-based enteroviral typing procedure that optimizes the specificity required for a typing protocol. There additionally persists a need for a typing procedure that avoids a requirement for a plethora of reagents directed toward the specificity of the various serotypes. There still further remains the need for an enteroviral typing procedure that does not require extended periods of time or complicated procedures to carry out. Thus, there remains a need for an operationally elegant and efficient typing procedure that utilizes the specificity that resides, for example, in the VP1 region. The present invention recognizes these needs, and addresses them.

SUMMARY OF THE INVENTION

As noted above, the determinants of serotype identity are understood to reside primarily in VP1. This amino acid sequence specificity should be reflected in the corresponding VP1 gene sequences. The present invention discloses a method, based on reverse transcription and amplification of a characteristic enteroviral nucleic acid segment, for detecting the presence of an enterovirus in a clinical sample. The method includes the steps of
  (i) obtaining a clinical sample from a subject;
  (ii) purifying RNA contained in the sample;
  (iii) reverse transcribing the RNA with primers effective to reverse transcribe enteroviral RNA to provide a cDNA;
  (iv) contacting at least a portion of the cDNA with
    (a) a composition that promotes amplification of a nucleic acid and
    (b) an oligonucleotide mixture wherein the mixture comprises at least one oligonucleotide that hybridizes to a highly conserved sequence of the sense strand of an enterovirus nucleic acid and at least one oligonucleotide that hybridizes to a highly conserved sequence of the antisense strand of an enterovirus nucleic acid, thereby providing an amplification mixture, such that, upon hybridizing, the oligonucleotides direct amplification of at least a portion of the nucleotide sequence of the VP1 gene of the enterovirus genome;
  (v) carrying out an amplification procedure on the amplification mixture, such that, if an enterovirus is present in the sample, an enterovirus amplicon is produced whose sequence includes a nucleotide sequence of at least a portion of the VP1 region of the enterovirus genome; and
  (vi) detecting whether the amplicon is present.

The presence of the amplicon, of course, indicates that an enterovirus is present in the sample.

In important embodiments of the method, the highly conserved sequences occur within the VP1 gene or within about 100 nucleotides from a terminus of the VP1 gene. Advantageously, at least one oligonucleotide of the mixture includes, at the 3' end thereof, a sequence that hybridizes to a sequence encoding the amino acid motif given by the sequences of either SEQ ID NO:80 or SEQ ID NO:81, and at least one oligonucleotide includes, at the 3' end thereof, a sequence that hybridizes to a sequence encoding a motif given by SEQ ID NO:82. Still more advantageously, the oligonucleotide mixture includes an oligonucleotide whose sequence contains, at the 3' end thereof, the sequence given by SEQ ID NO:3, and at least one oligonucleotide whose sequence contains, at the 3' end thereof, the sequence given by SEQ ID NO:4, or an oligonucleotide whose sequence contains, at the 3' end thereof, the sequence given by SEQ ID NO:9. In a highly advantageous embodiment, the sequences of these three oligonucleotides are given respectively by SEQ ID NO:3, SEQ ID NO:4, and SEQ ID NO:9.

In a further important embodiment of the method of detection, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85. In a further important embodiment, the oligonucleotide mixture contains an oligonucleotide whose sequence includes, at the 3' end thereof, the sequence given by SEQ ID NO:22, and at least one oligonucleotide chosen from among an oligonucleotide whose sequence includes, at the 3' end thereof, the sequence given by SEQ ID NO:19, an oligonucleotide whose sequence includes, at the 3' end thereof, the sequence given by SEQ ID NO:20, and an oligonucleotide whose sequence includes, at the 3' end thereof, the sequence given by SEQ ID NO:21. In a still more important embodiment, the oligonucleotide mixture contains an oligonucleotide whose sequence is given by SEQ ID NO:22, and at least one oligonucleotide chosen from among oligonucleotides whose sequences are given by SEQ ID NOs:19, 20, and 21.

In further significant embodiments of the method, the amplification procedure includes a polymerase chain reaction, and the sample is obtained from among whole blood or a fraction thereof, a bronchial wash, cerobrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal. In still other significant embodiments, the detection is carried out by a procedure chosen from among gel electrophoresis and visualization of amplicons contained in a resulting gel, capillary electrophoresis and detection of the emerging amplicon, probing for the presence of the amplicon using a labeled probe, and labeling a PCR primer employed in the method and detecting the label.

The invention additionally discloses a method for typing an enterovirus in a clinical sample that includes the steps of
  (i) obtaining a clinical sample from a subject;
  (ii) purifying RNA contained in the sample;
  (iii) reverse transcribing the RNA with primers effective to reverse transcribe enteroviral RNA to provide a cDNA;
  (iv) contacting at least a portion of the cDNA with
    (a) a composition that promotes amplification of a nucleic acid and
    (b) an oligonucleotide mixture wherein the mixture comprises at least one oligonucleotide that hybridizes to a highly conserved sequence of the sense strand of an enterovirus nucleic acid and at least one oligonucleotide tat hybridizes to a highly conserved sequence of the antisense strand of an enterovirus nucleic acid, thereby providing an amplification mixture, such that, upon hybridizing, the oligonucleotides direct amplification of at least a portion of the nucleotide sequence of the VP1 gene of the enterovirus genome;

(v) carrying out an amplification procedure on the amplification mixture, such that, if an enterovirus is present in the sample, an enterovirus sample amplicon is produced whose sequence includes a nucleotide sequence of at least a portion of the VP1 region of the enterovirus genome;

(vi) determining that the sample amplicon is present;

(vii) determining at least a partial nucleotide sequence of the sample amplicon;

(viii) providing a database consisting of prototypical nucleotide sequences, wherein each prototypical sequence is the sequence of a standard amplicon obtained from a member of a set of prototypical enterovirus serotypes by carrying out the procedure of steps (ii) through (v) on each prototypical enterovirus serotype, wherein each prototypical sequence comprises at least a portion of the sequence of the VP1 gene, and wherein the sequence of each prototypical VP1 gene is different from the sequence of every other prototypical VP1 gene in the database;

(ix) comparing the sequence of the sample amplicon with each prototypical sequence in the database; and (x) identifying the prototypical sequence that has the highest extent of identity to the sequence of the sample amplicon, thereby providing an identified serotype;

wherein the type of the sample is the serotype of the identified serotype.

In important embodiments of this method, the highly conserved sequences occur within the VP1 gene or within about 100 nucleotides from a terminus of the VP1 gene. More importantly, at least one oligonucleotide of the mixture includes, at the 3' end thereof, a sequence that hybridizes to a sequence encoding the amino acid motif given by the sequences of either SEQ ID NO:80 or SEQ ID NO:81, and at least one oligonucleotide includes, at the 3' end thereof, a sequence that hybridizes to a sequence encoding a motif given by SEQ ID NO:82. In significant embodiments of the method, the oligonucleotide mixture includes an oligonucleotide whose sequence contains, at the 3' end thereof, the sequence given by SEQ ID NO:3, at least one oligonucleotide whose sequence contains, at the 3' end thereof, the sequence given by SEQ ID NO:4 or an oligonucleotide whose sequence contains, at the 3' end thereof, the sequence given by SEQ ID NO:9. In a highly advantageous embodiment, the sequences of the oligonucleotides are given by SEQ ID NO:3, SEQ ID NO:4, and SEQ ID NO:9.

In an additional important embodiment, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85. In a further important embodiment, the oligonucleotide mixture contains an oligonucleotide whose sequence includes, at the 3' end thereof, the sequence given by SEQ ID NO:22, and at least one oligonucleotide chosen from among an oligonucleotide whose sequence includes, at the 3' end thereof, the sequence given by SEQ ID NO: 19, an oligonucleotide whose sequence includes, at the 3' end thereof, the sequence given by SEQ ID NO:20, and an oligonucleotide whose sequence includes, at the 3' end thereof, the sequence given by SEQ ID NO:2 1. In a still more important embodiment, the oligonucleotide mixture contains an oligonucleotide whose sequence is given by SEQ ID NO:22, and at least one oligonucleotide chosen from among oligonucleotides whose sequences are given by SEQ ID NOs: 19, 20, and 21.

In a further important aspect, the amplification procedure includes a polymerase chain reaction, and the resulting sample amplicon encompasses at least a portion of the nucleotide sequence for the VP1 gene of an enterovirus. The method furthermore importantly provides that the set of prototypical enterovirus serotypes comprises serotypes of coxsackie A viruses, coxsackie B viruses, echoviruses, and numbered enteroviruses. In advantageous aspects of the method, comparing the sequence of the sample amplicon with each sequence in the database employs a sequence alignment and comparison algorithm.

In further important aspects of the method, the sample is chosen from among whole blood or a fraction thereof, a bronchial wash, cerobrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal.

The present invention further provides an oligonucleotide containing, at the 3' end thereof, a sequence that hybridizes to a nucleotide sequence encoding an amino acid motif chosen from among the sequences given by SEQ ID NO:80, SEQ ID NO:81, SEQ ID NO:82, SEQ ID NO:83, SEQ ID NO:84, SEQ ID NO:85, and SEQ ID NO:86, or an oligonucleotide complementary to any of these oligonucleotides. In an advantageous embodiment, the complete sequence of the oligonucleotide is a sequence that hybridizes to a sequence encoding a motif whose sequence is chosen from among SEQ ID NO:80, SEQ ID NO:81, SEQ ID NO:82, SEQ ID NO:83, SEQ ID NO:84, SEQ ID NO:85, and SEQ ID NO:86, or is an oligonucleotide complementary to any of them.

In particularly important embodiments, such an oligonucleotide is one whose sequence contains, at the 3' end thereof, a sequence chosen from among the sequences given by SEQ ID NO:3, SEQ ID NO:4, SEQ ID NO:9, SEQ ID NO:19, SEQ ID NO:20, SEQ ID NO:21, and SEQ ID NO:22, or an oligonucleotide whose sequence is complementary to any of these oligonucleotides. In still more important embodiments, the sequence of the oligonucleotide consists of a sequence chosen from among SEQ ID NO:3, SEQ ID NO:4, SEQ ID NO:9, SEQ ID NO:19, SEQ ID NO:20, SEQ ID NO:21, and SEQ ID NO:22, or an oligonucleotide that is complementary to any of them.

The present invention further discloses a mixture of oligonucleotides including at least two oligonucleotides, wherein at least one of the oligonucleotides hybridizes to a sense strand of a double stranded nucleic acid and at least one of the oligonucleotides hybridizes to an antisense strand of the nucleic acid. The nucleic acid to which the oligonucleotides hybridize encodes the VP1 gene of an enterovirus, and the oligonucleotides hybridize to sequences that are highly conserved among the group of enteroviruses. The oligonucleotides, when hybridized to the nucleic acid, are bound in the correct orientation on their respective strands to direct the synthesis of an amplicon encoding at least a portion of the VP1 protein of enteroviruses when they are employed in an amplification procedure using the nucleic acid.

In important embodiments of the mixture, each oligonucleotide includes, at the 3' end thereof, a sequence that hybridizes to the nucleic acid. In still more important embodiments, the highly conserved sequences occur within the VP1 gene or within about 100 nucleotides from a terminus of the VP1 gene. Advantageously, at least one oligonucleotide includes, at the 3' end thereof, a sequence that hybridizes to a sequence encoding the amino acid motif given by the sequences of either SEQ ID NO:80 or SEQ ID NO:81, and at least one oligonucleotide includes, at the 3' end thereof, a sequence that hybridizes to a sequence encoding an amino acid motif given by SEQ ID NO:82. Still more advantageously, the mixture includes an oligonucleotide whose sequence contains, at the 3' end thereof, the sequence given by SEQ ID NO:3, an oligonucleotide whose sequence contains, at the 3' end thereof, the sequence given by SEQ ID NO:4, and an oligonucleotide whose sequence contains, at the 3' end thereof, the sequence given by SEQ ID NO:9. In a highly advantageous embodiment, the sequences of the oligonucleotides are given by SEQ ID NO:3, SEQ ID NO:4, and SEQ ID NO:9.

In an important embodiment, at least one oligonucleotide of the mixture includes, at the 3' end thereof, a sequence that hybridizes to a sequence encoding a motif given by SEQ ID NO:86, and at least one oligonucleotide includes, at the 3' end thereof, a sequence that hybridizes to a sequence encoding the amino acid motif given by the sequences of either SEQ ID NO:83, SEQ ID NO:84, or SEQ ID NO:85.

In additional significant embodiments, the oligonucleotide mixture includes an oligonucleotide whose sequence contains, at the 3' end thereof, the sequence given by SEQ ID NO:22, and at least one oligonucleotide chosen from among an oligonucleotide whose sequence contains, at the 3' end thereof, the sequence given by SEQ ID NO: 19, an oligonucleotide whose sequence contains, at the 3' end thereof, the sequence given by SEQ ID NO:20, and an oligonucleotide whose sequence contains, at the 3' end thereof, the sequence given by SEQ ID NO:21. In a still more significant embodiment, the oligonucleotide mixture includes an oligonucleotide whose sequence is given by SEQ ID NO:22, and at least one oligonucleotide chosen from among an oligonucleotide whose sequence is given by SEQ ID NO: 19, an oligonucleotide whose sequence is given by SEQ ID NO:20, and an oligonucleotide whose sequence is given by SEQ ID NO:21.

The present invention additionally provides a kit for use in conducting the typing method that includes a mixture of oligonucleotides, the mixture containing an oligonucleotide whose sequence contains; at the 3' end thereof, the sequence given by SEQ ID NO:3, an oligonucleotide whose sequence contains, at the 3' end thereof, the sequence given by SEQ ID NO:4, and an oligonucleotide whose sequence contains, at the 3' end thereof, the sequence given by SEQ ID NO:9. In important embodiments of the kit, the oligonucleotide sequences are given by SEQ ID NO:3, SEQ ID NO:4, and SEQ ID NO:9.

In additional significant embodiments, the kit includes an oligonucleotide whose sequence contains, at the 3' end thereof, the sequence given by SEQ ID NO:22, and at least one oligonucleotide chosen from among an oligonucleotide whose sequence contains, at the 3' end thereof, the sequence given by SEQ ID NO: 19, an oligonucleotide whose sequence contains, at the 3' end thereof, the sequence given by SEQ ID NO:20, and an oligonucleotide whose sequence contains, at the 3' end thereof, the sequence given by SEQ ID NO:21. In a still more significant embodiment, the oligonucleotide mixture includes an oligonucleotide whose sequence is given by SEQ ID NO:22, and at least one oligonucleotide chosen from among an oligonucleotide whose sequence is given by SEQ ID NO:19, an oligonucleotide whose sequence is given by SEQ ID NO:20, and an oligonucleotide whose sequence is given by SEQ ID NO:21.

BRIEF DESCRIPTION OF THE DRAWINGS

FIG. 1 is a schematic diagram of the non-polio enterovirus genome.

FIG. 2 illustrates RT-PCR amplification of all enterovirus prototype strains using primer pairs given by SEQ ID NOs:3 and 4, and by SEQ ID NOs: 3 and 9. PCR products were resolved by 1% agarose gel electrophoresis and visualized by ethidium bromide staining and UV transillumination. Panel A: Coxsackie A viruses, Coxsackie B viruses, and polioviruses amplified with primer pair given by SEQ ID NOs:3 and 4; Panel B: Coxsackie A viruses, Coxsackie B viruses, and polioviruses amplified with primer pair given by SEQ ID NOs: 3 and 9; Panel C: Echoviruses and numbered enteroviruses amplified with primer pair given by SEQ ID NOs: 3 and 4; Panel D: Echoviruses and numbered enteroviruses simplified with primer pair given by SEQ ID NOs: 3 and 9.

DETAILED DESCRIPTION OF THE INVENTION

The present invention advantageously provides methods for serotyping enteroviruses obtained from clinical samples. The methods are easily extended to human poliovirus, human picornaviruses such as human rhinovirus, and nonhuman picornaviruses such as bovine enterovirus and simian picornavirus. The procedures are easily and rapidly implemented using common laboratory procedures and instrumentation. They avoid the need for cumbersome, time-consuming and resource-intensive methods such as cell culture and/or host animal infection. They furthermore avoid reliance on prototypical antiserum pools which may fail to identify an enterovirus in a contemporary clinical sample because of antigen drift and escape from immunological reactivity. The methods of the present invention further advantageously permit identifying a serotype as being the most probable serotype even in the case of antigen drift, since nucleotide sequences are matched to provide a most probable serotype match, or, failing a unique match, a set of most probable serotype matches, even in the absence of a high extent of identity.

As used herein, the non-polio enteroviruses refer to the species/subgroups and serotypes, shown in Table 1, that are known in the field at the present time.

TABLE 1

Non-polio Enterovirus Species/Subgroups and Serotypes.

| Species/Subgroup | Serotypes[a] |
|---|---|
| Coxsackievirus A | CA1 to CA22, CA24 |
| Coxsackievirus B | CB1-CB6 |
| Echovirus | E1-E7, E9, E11-E27, E29- |
| Enterovirus (Numbered) | EV68-EV71 |

[a]Serotypes CA-23, E-10, E-28, and EV-72 have been reclassified (Miller, Clin. Infect. Dis. 16: 612-613 (1993)). E-8 has been reclassified (Committee on the Enteroviruses, Virology 16: 501-504 (1962); Harris et al., J. Infect. Dis. 127: 63-68 (1973)).

As used herein, a "clinical sample" or a "clinical isolate" relates to any sample obtained from a subject for use in carrying out the procedures of the present invention. In a principal aspect, the subject is suspected of suffering from a disease or syndrome that is at least partially caused by an enterovirus. The subject may also be an asymptomatic individual considered to be at risk of enterovirus infection. The sample may be a cellular sample such as a tissue sample, for example, a sample of lung tissue obtained as a biopsy or post-mortem, a fluid sample such as blood, saliva, sputum, urine, cerebrospinal fluid, or a swabbed sample obtained by swabbing a mucus membrane surface such as a nasal surface, a pharyngeal surface, a buccal surface, and the like, or it may be obtained from an excretion such as feces, or it may be obtained from other bodily tissues or body fluids commonly used in clinical diagnostic testing. In its broadest sense, a "clinical sample" or a "clinical isolate" as used herein is obtained from a human subject or a non-human mammalian subject, and is directed to suspected symptoms or syndromes ascribable to a picornavirus or enterovirus infection.

As used herein, purification of RNA as a step in the methods of the invention, in particular, as a step leading up to a RT-PCR procedure, relates to releasing RNA from a latent or inaccessible form in a virion or a cell and allowing the RNA to become freely available. In such a state, it is suitable for effective amplification by reverse transcription and use of the polymerase chain reaction. Releasing RNA may include steps that achieve the disruption of virions containing viral RNA, as well as disruption of cells that may harbor such virions. Purification of RNA is generally carried out under conditions that rigorously and effectively exclude or inhibit any ribonuclease activity that may be present. Additionally, purification of RNA may include steps that achieve at least a partial separation of the RNA dissolved in an aqueous medium from other cellular or viral components, wherein such components may be either particulate or dissolved.

As used herein, "reverse transcription" or "RT" relates to a procedure catalyzed by an enzyme activity, reverse transcriptase, that synthesizes a cDNA from a single stranded RNA molecule, with the use of oligonucleotide primers having free 3'-hydroxyl groups. As used herein the term "polymerase chain reaction" or "PCR" relates to a procedure whereby a limited segment of a nucleic acid molecule, which frequently is a desired or targeted. segment, is amplified repetitively to produce a large amount of DNA molecules which consist only of that segment. The procedure depends on repetition of a large number of priming and transcription cycles. In each cycle, two oligonucleotide primers bind to the segment, and define the limits of the segment. A primer-dependent DNA polymerase then transcribes, or replicates, the strands to which the primers have bound. Thus, in each cycle, the number of DNA duplexes is doubled.

As used herein the term "primer" or "oligonucleotide primer" relates to an oligonucleotide having a specific or desired nucleotide sequence which is complementary to a particular sequence on one of the strands of a DNA duplex. When the primer is caused to hybridize to the specific sequence in a DNA duplex to which it is complementary, it may serve as the priming position, or the initiation position, for the action of a primer-dependent DNA polymerase activity. The primer, once hybridized, acts to define the 5' end of the operation of the transcription activity of the polymerase on the duplex. Commonly in PCR, a specific pair of primers is employed, wherein one of the primers hybridizes to one of the strands and the second primer hybridizes to the complementary strand. The primers hybridize in such an orientation that transcription, which proceeds in the direction from 5'- to 3'-, is in the direction leading from each primer toward the site of hybridization of the other primer. After several rounds of hybridization and transcription the amplified DNA produced is a segment having a defined length whose ends are defined by the sites to which the primers hybridize.

The oligonucleotide primers of the invention are intended for use in a RT-PCR-based amplification of a target segment of a nucleic acid from an enterovirus. Both RT and PCR rely on the action of a DNA polymerase activity to extend the new DNA strands beyond the 3' termini of the primers. Since DNA polymerases extend a chain in the direction from 5' to 3', an oligonucleotide that contains sequences in addition to those nucleotides that hybridize to the target nucleic acid and serve as the primer must have the primer sequence at the 3' end of the oligonucleotide. Additionally, any complements of the oligonucleotides contemplated in the invention must have the sequence complementary to the hybridizing sequence at the 5' end of the molecule such that action of a DNA polymerase will generate a primer oligonucleotide having its complementary sequence at its 3' end.

As used herein the terms "specific to" or "specific for" a target sequence, in relation to a nucleic acid sequence such as an oligonucleotide sequence, relate to a nucleotide sequence that hybridizes, under conditions used in given experimental circumstances, to the target but does not hybridize under those circumstances to sequences that are not target sequences. Nucleotide sequences that are specific for a particular target, such as the enteroviral target sequences that are included in the subject matter of the present invention, are those that include bases all of which are complementary to the corresponding base on the target.

Further as used herein, "specificity" of a nucleic acid sequence for a target sequence also encompasses nucleic acids and oligonucleotides having a small number of nucleotides which may not be complementary to the corresponding nucleotides of the target sequence. Such sequences are still "specific" for the target sequence, as used herein, as long as the extent of deviation from complementarity remains functionally of no consequence. In particular, such a sequence is "specific" for the target sequence as long as it hybridizes effectively to the target sequence but does not hybridize to any sequence that is not a target sequence, under the conditions used in given experimental circumstances.

As used herein, an "amplicon" relates to a double stranded nucleic acid segment having a defined size and sequence that results from an amplification procedure, such as a PCR procedure. The size of the amplicon is governed by the sites on the two strands of a nucleic acid duplex to which the primers bind. As explained in U.S. Pat. No. 4,683,195, that segment of the product nucleic acid becomes the prevalent product of the amplification procedure after a small number of cycles of amplification.

As used herein, the terms "prototype", "prototypical sequence", "prototypical amplicon", and "prototypical enterovirus serotype" relate, insofar as the root "prototyp-" occurs in each of these terms, to the enterovirus serotypes which were used to establish the classical antisera defined against each serotype. These were originally obtained several decades ago, as described in Lim et al. (1960) and subsequently, for example, in Melnick et al. (Bull. Wld. Hlth. Org. 48:2163-268 (1973)), and Melnick et al. (1985). As used herein, these terms are distinguished from variants of a given prototypical serotype, wherein a variant represents a phenotype resulting from antigenic drift, such as a phenotype that may represent an escape mutant. Such variants may occur in the field among contemporary clinical isolates of enteroviruses.

As used herein, a "motif" relates to a short sequence of amino acid residues that is highly conserved among a family of proteins from different species or variants.

Developing a Database of Nucleotide Sequences Characteristic of the Prototypical Enteroviruses. In order to practice the methods of the present invention, a database of sequences characteristic of the prototypical enteroviruses is needed. In order to prepare such a database, a region of the enteroviral genome is selected that has within its nucleotide sequence sufficient variation among the different serotypes that the sequence from each serotype may be considered to be unique. In the present invention, the VP1 region of the viral RNA was identified as having the requisite sequence uniqueness from one serotype to another. Among the entries in Table 2, below, direct comparison of results based on VP1 versus those obtained with VP2 for the following variants of respective serotypes provided evidence that VP1 affords the selectivity required for this invention, whereas VP2 does not. The variants are CA24v strain EH24/70, E4 strain Du Toit, E4 strain Shropshire, E6 strain Charles, E6' strain Cox, E6" strain Burgess, E8 strain Bryson, E9 strain Barty, E11' strain Silva, E30 strain Frater, E30 strain Giles, E30 strain PR-17, E34 strain DN-19, PV1 strain Sabin, PV2 strain Sabin, and PV3 strain Sabin. Once such a region is identified, the nucleotide sequences from this region are determined for each virus among the set of prototypical serotypes. The serotype prototypes of interest in the present invention are listed in Tables 1 and 2; Table 2 includes entries for additional enteroviruses and picomaviruses as well. The viruses may be obtained from publicly available deposits made at the American Type Culture Collection (Rockville, Md.).

TABLE 2

Enterovirus and Picornavirus VP1 Sequences Used in Establishing a Sequence Database

| Serotype | Strain | GenBank Accession Number | SEQ ID NO: |
|---|---|---|---|
| CA1 | Tompkins | AF081293 | 23 |
| CA2 | Fleetwood | L28146 (a) | |
| CA3 | Olson | AF081294 | 24 |
| CA4 | High Point | AF081295 | 25 |
| CA5 | Swartz | AF081296 | 26 |
| CA6 | Gdula | AF081297 | 27 |
| CA7 | AB-IV | AF061298 | 28 |
| CA8 | Donovan | AF081299 | 29 |
| CA9 | Griggs | D00627 (b) | |
| CA10 | Kowalik | AF081300 | 30 |
| CA11 | Belgium-1 | AF081301 | 31 |
| CA12 | Texas-12 | AF081302 | 32 |
| CA13 | Flores | AF081303 | 33 |
| CA14 | G-14 | AF081304 | 34 |
| CA15 | G-9 | AF081305 | 35 |
| CA16 | G-10 | U05876 (c) | |
| CA17 | G-12 | AF081306 | 36 |
| CA18 | G-13 | AF081307 | 37 |
| CA19 | 8663 | AF081308 | 38 |
| CA20 | IH-35 | AF081309 | 39 |
| CA21 | Kuykendall | D00538 (d) | |
| CA22 | Chulman | AF081310 | 40 |
| CA24 | Joseph | AF081311 | 41 |
| CA24v | EH24/70 | D90457 (e) | |
| CB1 | Conn-5 | M16560 (f) | |
| CB2 | Ohio-1 | AF081312 | 42 |
| CB3 | Nancy | M16572 (g) | |
| CB4 | JVB | D00149 (h) | |
| CB5 | Faulkner | X67706 (i) | |
| CB6 | Schmitt | AF081313 | 43 |
| E1 | Farouk | AF081314 | 44 |
| E2 | Cornelis | AF081315 | 45 |
| E3 | Morrisey | AF081316 | 46 |

TABLE 2-continued

Enterovirus and Picornavirus VP1 Sequences Used in Establishing a Sequence Database

| Serotype | Strain | GenBank Accession Number | SEQ ID NO: |
|---|---|---|---|
| E4 | Pesacek | AF081317 | 47 |
| E4 | Du Toit | AF081318 | 48 |
| E4 | Shropshire | AF081319 | 49 |
| E5 | Noyce | AF081320 | 50 |
| E6 | Charles | U16283 (j) | |
| E6 | D'Amori | AF081321 | 51 |
| E6' | Cox | AF081322 | 52 |
| E6" | Burgess | AF081323 | 53 |
| E7 | Wallace | AF081324 | 54 |
| E8 | Bryson | AF081325 | 55 |
| E9 | Hill | X84981 (k) | |
| E9 | Barty | X92886 (l) | |
| E11 | Gregory | X80059 (m) | |
| E11' | Silva | AF081326 | 56 |
| E12 | Travis | X79047 (n) | |
| E13 | Del Carmen | AF081327 | 57 |
| E14 | Tow | AF081328 | 58 |
| E15 | CII96-51 | AF081329 | 59 |
| E16 | Harrington | X89545 (o) | |
| E17 | CHHE-29 | AF081330 | 60 |
| E18 | Metcalf | AF081331 | 61 |
| E19 | Burke | AF081332 | 62 |
| E20 | JV-1 | AF081333 | 63 |
| E21 | Farina | AF081334 | 64 |
| E22 | Harris | S45208 (o) | |
| E23 | Williamson | AF055846 (p) | |
| E24 | De Camp | AF081335 | 65 |
| E25 | JV-4 | AF081336 | 66 |
| E26 | Coronel | AF081337 | 67 |
| E27 | Bacon | AF081338 | 68 |
| E29 | JV-10 | AF081339 | 69 |
| E30 | Bastianni | AF081340 | 70 |
| E30 | Frater | AF081341 | 71 |
| E30 | Giles | AF081342 | 72 |
| E30 | PR-17 | AF081343 | 73 |
| E31 | Caldwell | AF081344 | 74 |
| E32 | PR-10 | AF081345 | 75 |
| E33 | Toluca-3 | AF081346 | 76 |
| E34a | DN-19 | AF081347 | 77 |
| EV68 | Fermon | AF081348 | 78 |
| EV69 | Toluca-1 | AF081349 | 79 |
| EV70 | J670/71 | D00820 (q) | |
| EV71 | BrCr | U22521 (r) | |
| PV1 | Mahoney | J02281(s) | |
| PV1 | Sabin | V01150 (t) | |
| PV2 | Lansing | M12197 (u) | |
| PV2 | Sabin | X00595 (v) | |
| PV3 | Leon | K01392 (w) | |
| PV3 | Sabin | X00596 (v) | |
| BEV1 | VG-5-27 | D00214 (x) | |
| BEV2a | RM-2 | X79369 (y) | |
| BEV2b | PS-87 | X79368 (y) | |
| HRV3 | Unknown | U60874 | |
| PEV9 | UKG/410/73 | Y14459 (z) | |
| SVDV | H/3'76 | D00435 (h) | |
| HRV1b | Unknown | D00239(dd) | |
| HRV2 | Unknown | X02316 (aa) | |
| HRV3 | Unknown | U60874 | |
| HRV14 | Unknown | K02121, X01087 (bb) | |
| HRV16 | Unknown | L24917(ee) | |
| HRV89 | 41467 Gallo | M16248(ff) | |
| HAV | HM-175 | M14707 (cc) | |

Notes for Table 2:
PEV, porcine enterovirus;
SVDV, swine vesicular disease virus;
HRV, human rhinovirus;
HAV, hepatitis A virus.
(a) Pulli, T., et al., Virology 211: 30-38 (1995).
(b) Chang, K., et al., J. Gen. Virol. 70: 3269-3280 (1989).
(c) Poyry, T., et al., Virology 202: 982-987 (1994).
(d) Hughes, P. J., et al. J. Gen. Virol. 70: 2943-2952 (1989).

TABLE 2-continued Enterovirus and Picornavirus VP1 Sequences Used in Establishing a Sequence Database

| Serotype | Strain | GenBank Accession Number | SEQ ID NO: |
|---|---|---|---|

(e) Supanaranond, K., et al., Virus. Genes 6: 149-158 (1992).
(f) Iizuka, N., et al. Virology 156: 64-73 (1987).
(g) Lindberg, A. M., et al., Virology 156: 50-63 (1987).
(h) Jenkins, O., et al., J. Gen. Virol. 68: 1835-1848 (1987).
(i) Zhang, G., et al., J. Gen. Virol. 74: 845-853 (1993).
(j) Harris, L. F., et al., J. Infect. Dis. 127: 63-68 (1973).
(k) Zimmermann, H., et al., Virus Res. 39: 311-319 (1995).
(l) Zimmermann, H., et al., Virus Genes 12: 149-154 (1996).
(m) Dahllund, L., et al., Virus Res. 35: 215-223 (1995).
(n) Kraus, W., et al. J. Virol. 69: 5853-5858 (1995).
(o) Huttunen, P., et al., J. Gen. Virol. 77: 715-725 (1996).
(p) Oberste, M. S., et al., Virus. Res. 56: 217-223 (1998).
(q) Ryan, M. D., et al., J. Gen. Virol. 71: 2291-2299 (1990).
(r) Brown, B. A., et al., Virus. Res. 39: 195-205 (1995).
(s) Kitamura, N. B., et al., Nature 291: 547-553 (1981); Racaniello, V. R., et al. Proc. Natl. Acad. Sci. USA 78: 4887-4891 (1981).
(t) Dorner, A. J., et al., J. Virol. 42: 1017-1028 (1982); Emini, E. A., et al., J. Virol. 42: 194-199 (1982); Nomoto, A., et al. Proc. Natl. Acad. Sci. USA 79: 5793-5797 (1982).
(u) La Monica, N., et al., J. Virol. 57: 515-525 (1986).
(v) Toyoda, H., et al. J. Mol. Biol. 174: 561-585 (1984).
(w) Stanway, G., et al. Proc. Natl. Acad. Sci. USA 81: 1539-1543 (1984).
(x) Earle, J. A., et al., J. Gen. Virol. 69: 253-263 (1988).
(y) McNally, R. M., et al., Arch. Virol. 139: 287-299 (1994).
(z) Peng, J., et al., Unpublished data.
(aa) Skern, T., et al., Nucl. Acids Res. 13: 2117-2126 (1985).
(bb) Callaghan, P. L., et al., Proc. Natl. Acad. Sci USA 82: 732-736 (1985); Stenway, G., et al., Nucl. Acids Res. 12: 7859-7875 (1984).
(cc) Cohen, J. L., et al., J. Virol. 61: 50-59 (1987).
(dd) Hughes, P. J., et al., J. gen. VFirol. 69: 49-58 (1988).
(ee) Lee, W. M., et al., Virus Genes 9: 177-181 (1995).
(ff) Duechler, M., et al., Proc Natl. Acad. Sci. USA 84: 2605-2609 (1987).

The virus specimens are used to infect any enterovirus-susceptible cell line in culture, including, by way of nonlimiting example, RD (human rhabdomyoscarcoma) cells, HLF (human embryonic lung fibroblast) cells, LLC-MK$_2$ (monkey kidney) cells, or BGM (buffalo green monkey kidney) cells; alternatively, a tissue homogenate in tissue culture medium may be prepared from mouse brain after infection of the mouse with the virus. In the case of cell cultures, the culture supernatant is used. In the case of the brain homogenate, the whole homogenate, after growth of the virus, is used. Viral RNA is extracted from the growth media containing the enterovirus prototypes by any method that releases the RNA from the virion and/or the cell components and provides a purified preparation of the RNA. By way of nonlimiting example, the RNA may be extracted using guanidinium isothiocyanate, such as the single-step isolation by acid guanidinium thiocyanate-phenol-chloroform extraction of Chomczynski et al. (Anal. Biochem. 162:156-159 (1987)). Alternatively, the virion may be disrupted by a suitable detergent in the presence of proteases and/or inhibitors of ribonuclease activity. The RNA released from the virion is isolated or purified, using, for example, methods such as precipitation with an alcohol (e.g., ethyl alcohol or isopropyl alcohol) or banding in a suitable density gradient using an ultracentrifuge.

The purified viral RNA is then subjected to a reverse transcription to prepare a cognate cDNA that encompasses the region of the genome chosen for discriminating between serotypes (i.e., the region encoding VP1). An advantageous way of achieving this is to use a set of random oligonucleotide primers in the reverse transcription, such that certain of the primers in the set will hybridize to the RNA and yield one or more cDNA molecules from the virus encompassing the required serotype-specific nucleotide sequence. Alternatively, gene-specific primers based on a viral RNA-specific sequence from a suitable cDNA may be employed for reverse transcription. Subsequently, the cDNA is amplified using a suitable amplification protocol. By way of nonlimiting example, a polymerase chain reaction (PCR) protocol may be employed for this purpose. PCR is described in operational detail in, for example, "Molecular Cloning: A Laboratory Manual," 2nd ed., Sambrook, Fritsch and Maniatis, Cold Spring Harbor Laboratory, Cold Spring Harbor, N.Y., 1989; "Current Protocols in Molecular Biology," Ausubel et al., John Wiley and Sons, New York 1987 (updated quarterly); and "PCR Protocols: A Guide to Methods and Applications," Innis et al., Academic Press, San Diego, Calif. 1990; and in U.S. Pat. Nos. 4,683,195; 4,683,202; 4,965,188; 5,578,467; 5,545,522; and 5,624,833, all of which are incorporated herein by reference.

For the PCR of the cDNA to yield an amplicon containing a sequence from the VP1 region, primers such as those provided in Table 3 (SEQ ID NOs:1-22) may be employed. In Table 3, nucleotide sequence positions are given relative to the sequence of poliovirus1-Mahoney (Kitamura, N. B., et al., Nature 291:547-553 (1981); Racaniello, V. R., et al. Proc. Natl. Acad. Sci. USA 78:48874891 (1981)).

TABLE 3

Primers Used for PCR Amplification of the VP1 Region of Enteroviruses

| Primer | Sequence | Gene | Position | SEQ ID NO |
|---|---|---|---|---|
| 008 | GCRTGCAAGAYTTCTCWGT | VP3 | 2411-2430 | 1 |
| 009 | NGCNCCDGAPPTTGNTGSCC | 2A | 3409-3391 | 2 |
| 011 | GCICCIGAYTGITGICCRAA | 2A | 3408-3389 | 3 |
| 012 | ATGTAYGTICCICCIGGIGG | VP1 | 2951-2970 | 4 |
| 013 | GGIGCRTTICCYTGIGTCCA | VP1 | 3051-3032 | 5 |
| 019 | ACRTGICIIGTYTGCATIGT | VP1 | 2676-2657 | 6 |
| 035 | AWITTYTAYGAYGGITGG | VP1 | 3098-3115 | 7 |
| 036 | TAIAIIGTICCCATRTTRTT | VP1 | 3201-3182 | 8 |
| 040 | ATGTAYRTICCIMCIGGIGC | VP1 | 2951-2970 | 9 |
| 041 | GGIGGIGGRTCIGTJAKYTT | VP1 | 3054-3035 | 10 |
| 045 | GAIGARAAYCTIATIGARAC | VP1 | 2648-2667 | 11 |
| 046 | CCCATIAKRTCIATRTCCC | VP1 | 2820-2801 | 12 |
| 050 | GTRCTYACIAIIAGRTCYCT | 2A | 3513-3494 | 13 |
| 051 | TSAARYTGTGCAARGACAC | VP3 | 2429-2448 | 14 |
| 052 | STGYCCAGATTCAGTGT | VP3 | 2413-2430 | 15 |
| 053 | GGNACNCAYRTNATHTGGGA | VP3 | 2216-2235 | 16 |
| 054 | GCCITRTTITGRTGICCRAA | 2A | 3408-3389 | 17 |
| 055 | GGIACICAYRTIRTITGGGA | VP3 | 2216-2235 | 18 |
| 187 | ACIGCIGYIGARACIGGNCA | VP1 | 2612-2631 | 19 |

TABLE 3-continued

Primers Used for PCR Amplification of the VP1
Region of Enteroviruses

| Primer | Sequence | Gene | Position | SEQ ID NO |
|---|---|---|---|---|
| 188 | ACIGCIGTIGARACIGGNG | VP1 | 2612-2630 | 20 |
| 189 | CARGCIGCIGARACIGGNGC | VP1 | 2612-2631 | 21 |
| 222 | CICCIGGIGGIAYRWACAT | VP1 | 2969-2951 | 22 |

These primers were designed to amplify a broad range of cDNA fragments drawn from the set of enteroviruses (see Example 2). The primers of SEQ ID NOs:1-22 were designed based on information available regarding known sequences of non-polio enteroviruses, as well as sequences in the VP1 region obtained as part of the development of the present invention (see Example 1; see Table 2 for GenBank accession numbers of the sequences). Additional information used to design the primers of SEQ ID NOs:1-22, especially the primers of SEQ ID NOs:19-22, was obtained from known sequences of other members of the Picornaviridae family, as provided in Table 2.

The amplicons obtained from the PCR protocol applied to each prototype virus are sequenced to obtain the nucleotide sequence in each. Procedures that may be used for sequencing include the methods of Maxam and Gilbert (Meth. Enzymol. 65, 499-566 (1980)) and Sanger et al., (Proc. Natl. Acad. Sci. USA 74:5463-5467 (1977)) (see also Sambrook et al., (1989)). The method of Maxam and Gilbert involves random chemical degradation reactions carried out on a nucleic acid labeled at one end. Each of four separate degradation reactions is specific for a different one of the four bases in the nucleic acid. The method of Sanger et al. involves use of a different 2',3'-dideoxynucleotide chain terminator in each of four template-driven DNA polymerase reactions. The Sanger method is readily implemented in automated sequencing instruments, such as those of PE-Biosystems, Foster City, Calif. The VP1 sequences that were obtained with the above procedures were incorporated into the non-polio enterovirus database of the present invention (see Table 2).

Typing of Clinical Isolates Obtained in the Field. A clinical sample is obtained from a subject suspected of harboring an enterovirus. Any suitable clinical specimen may be used for this purpose. Commonly, and by way of nonlimiting example, such a sample may be whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant. from a tissue culture, or tissue from an experimentally infected animal.

Viral RNA may be isolated from a clinical sample either directly or after inoculating a cell culture with the clinical sample and cultivating a larger virus population. Direct isolation is rapid but may result in low virus titer, whereas inoculation and cell culture will provide a higher titer but may take several days.

In order to obtain amplicons from viral RNA, the RNAs from the virus isolates are treated with a reverse transcriptase primer preparation that contains a random oligonucleotide RT primer, such as a library of random hexanucleotides. The resulting cDNA is amplified in a PCR procedure using a mixture of oligonucleotide primers that hybridize to motifs that are highly conserved throughout the enteroviruses, or more generally, motifs that are highly conserved among the picornaviruses. As used herein, the notion of hybridizing specifically to a highly conserved region encoding a highly conserved amino acid motif relates to identifying at least two nucleotide sequences in the viral genomes which display minimal variation across both the complete spectrum of prototypical enterovirus serotypes, as well as the variants that may be present in clinical samples at any given time. Thus, at least two relatively constant amino acid sequences, or motifs, encoded by these nucleotide sequences, occur phenotypically in all or most of the viruses of the enteroviral species and variants, and the corresponding coding sequences in. the nucleic acid are likewise relatively constant across the prototypes and variants. Such conserved or invariant sequences, or motifs, are required in order that a single pair of oligonucleotide primers, or as small a set of such primers as is practical, suffices to prime the amplification of all or the maximum possible number of prototypical viruses and all or the maximum number of viral variants infecting the population at any given time.

In important embodiments of the invention, the primers used are a mixture of oligonucleotides whose use in a PCR amplification provides an amplicon encompassing most or all of the VP1 gene. By way of nonlimiting example, such a mixture may include an oligonucleotide chosen from among an oligonucleotide whose sequence contains, at the 3' end thereof, the sequence given by SEQ ID NO:4, an oligonucleotide whose sequence contains, at the 3' end thereof, the sequence given by SEQ ID NO:9, and a mixture thereof, as well as an oligonucleotide whose sequence contains, at the 3' end thereof, the sequence given by SEQ ID NO:3 (see Table 3); in particularly important embodiments the oligonucleotides employed according to the above mixtures are primer 011 (SEQ ID NO:3), primer 012 (SEQ ID NO:4), and primer 040 (SEQ ID NO:9). The use of either or both of the primers (012, SEQ ID NO:4 and 040, SEQ ID NO:9) provides specific hybridization to target sequences in the 5' region of the VP1 gene of most or all of the non-polio enteroviruses. The third primer, 011 (SEQ ID NO:3), specifically hybridizes to a target sequence in the 2A region of most or all the non-polio enteroviruses. Each primer is disclosed in PCT application WO 98/14611, which is incorporated herein by reference.

More generally, primer sets that include a mixture of oligonucleotides that contain the sequences given by SEQ ID NO:19, SEQ ID NO:20, SEQ ID NO:21, or SEQ ID NO:22 may be employed in amplifying a broad range of picornaviruses. Specifically, oligonucleotides chosen from among an oligonucleotide whose sequence contains, at the 3' end thereof, the sequence given by SEQ ID NO:19, an oligonucleotide whose sequence contains, at the 3' end thereof, the sequence given by SEQ ID NO:20, an oligonucleotide whose sequence contains, at the 3' end thereof, the sequence given by SEQ ID NO:21, and mixtures thereof, may be combined with an oligonucleotide whose sequence contains, at the 3' end thereof, the sequence given by SEQ ID NO:22 (see Table 3) for use in the present method. Advantageously, the oligonucleotides included in the above mixtures are primer 187 (SEQ ID NO: 19), primer 188 (SEQ ID NO:20), primer 189 (SEQ ID NO:21), and primer 222 (SEQ ID NO:22).

Using the mixtures of oligonucleotide primers set forth in the preceding paragraphs leads to preparation of the enteroviral PCR amplicons according to the method of this invention.

The amplicons are then either detected or isolated for sequence analysis. They may be isolated by any of a variety of amplicon purification procedures that serve to provide a purified preparation of the amplicon. These include, by way of nonlimiting example, gel electrophoresis coupled with visualization using a fluorescent dye and extraction of the detected amplicon from the gel, and extraction from the amplification solution using an immobilized derivative of one or more of the PCR primers to bind a strand of the amplicon after it has been denatured. The purified amplicons may be seqenced using conventional sequencing techniques or procedures.

The nucleotide sequence obtained for the amplicon derived from a particular clinical sample of an enterovirus is then matched with the sequences in the database of prototypical sequences describing the known serotypes of enteroviruses. The sequence matching may be carried out by any suitable sequence matching algorithm designed to determine the extent of identity or similarity between a query sequence in its entirety and a standard or reference sequence. By way of nonlimiting example, such an algorithm may be that of Needleman and Wunsch (J. Mol. Biol. 48:443-453 (1970) implemented in the program Gap in the Wisconsin Sequence Analysis Package, version 9.1), and the like. Such algorithms provide a result that the query sequence most resembles a particular one, and (in most cases) only one, of the reference sequences drawn from the database. According to the present method, the serotype of the enterovirus in the clinical sample is the serotype of the sequence from the database identified as most closely resembling the sequence of the sample.

Numerous advantages result upon implementation of the present invention. Typing of an enterovirus in a clinical sample may be done avoiding the necessity of culturing the sample in a cell culture or in a whole animal host (e.g., mouse). Such procedures are cumbersome, labor-intensive and resource-intensive, and pose dangers of infection to the workers conducting the assay. The typing likewise avoids the necessity of conducting a standardized serotyping assay. Serotyping is labor-intensive, and requires the availability of the antiserum pools that are specific or selective for the various enterovirus serotypes. Furthermore, serotyping using these procedures is not very effective because numerous variants and escape mutants in field samples of enteroviruses avoid detection and provide, therefore, a false negative result. The present invention additionally avoids the disadvantages of known PCR amplification procedures employed with non-polio enteroviruses, which are largely based on the conserved 5' untranslated region of the non-polio enterovirus genome, and thereby lack a means for typing the samples found.

In contrast, the present invention provides the only PCR-based means for typing a clinical sample of an enterovirus available at the present time. The procedure is easy to carry out and provides an unambiguous, and accurate, typing of a clinical sample in a large fraction of test cases that were also typed by standard serotype pools. Typing of cases of enterovirus-caused diseases or syndromes permits an appropriate therapy to be chosen in suitable cases. Such therapy should lead to amelioration of the severity of the disease or syndrome and, hopefully, a complete recovery. Typing furthermore provides important public health and epidemiological information that could lead to protective and/or preventive measures being taken among a population at risk of contracting such a disease or syndrome.

The following examples are intended to illustrate the invention and not to limit it.

EXAMPLE 1

Establishing a Database of Sequences Corresponding to Standard Non-polio Enterovirus Serotypes The viruses used for sequence analysis are listed in Table 2, above. The prototypical virus samples were obtained from the American Type Culture Collection. The viruses were propagated in RD cells, HLF cells, LLC-$MK_2$ cells, or primary monkey kidney cells using Eagle's MEM supplemented with 2% fetal bovine serum or by intracerebral inoculation of newborn mice (see Grandien, M., et al., "Enteroviruses and Reoviruses", in Diagnostic procedures for viral, rickettsial, and chlamydial infections, 6th Ed. (Schmidt, N. J., et al., eds.) 1989, Amer. Public Health Assoc., Washington, D.C., pp. 513-578) . The isolation of the viral RNA, and the RT-PCR amplification was conducted as described by Oberste et al. (Am. J. Trop. Med. Hyg. 58:4146 (1998b)). In summary, in this procedure, viral RNA was extracted from infected cell culture supernatants, or from 10% infected mouse brain homogenate with Trizol LS™ (Life Technologies, Inc., Gaithersburg, Md.), and cDNA was obtained by use of a set of random hexanucleotide primers (Boehringer Mannheim Biochemicals, Indianapolis, Ind.), and a SuperScript™ preamplification kit (Life Technologies, Inc.). Reverse transcription was performed in a solution containing 20 mM Tris chloride pH 8.3, 50 mM KCl, 2.5 mM $MgCl_2$, 0.1 M dithiothreitol, 0.5 mM each of DATP, dATP, dGTP, and TTP, 0.8 µM random hexamer primer, 5 µL RNA, and 10 U SuperScript II™ reverse transcriptase (Life Technologies, Inc.). The reaction proceeded for 1 h at 42° C.

The resulting cDNAs were amplified by PCR using primers for VP3 and 2A shown in Table 3 (SEQ ID NOs:1-18), in a reaction containing 20 mm Tris chloride pH 8.3, 50 mM KCl, 2.5 mM $MgCl_2$, 0.2 mM each of DATP, D.C.TP, dGTP, and TrP, 1 µM sense-orientation primer, 1 µM antisense-orientation primer 1 µL cDNA from the reverse transcription step, above, and 1.25 U *Thermus aquaticus* DNA polymerase (Life Technologies, Inc.). The reaction was incubated at 94° C. for 3 min, then followed by 35 cycles of 94° C. for 30 s, 42° C. for 30 s, and 72° C. for 30 s, followed by incubation at 72° C. for 5 min. The specific primer pairs used differed from one virus to another in order to obtain satisfactory yields of the amplicons. For some viruses, VP1 was amplified as two overlapping fragments with internal VP1 primers as well as the VP3 and 2A primers. The PCR products were gel isolated and purified in preparation for sequencing with the QIAquick™ gel extraction kit (QIAGEN, Inc., Santa Clarita, Calif.), in which DNA is selectively adsorbed to a silica gel membrane at pH below 7.5 at high salt concentration. The impurities are separated from the membrane, then the DNA is eluted therefrom using Tris buffer or water. Sequencing was carried out on an automated DNA sequencer (Applied Biosystems Division, Perkin Elmer, Inc., Foster City, Calif.) using 2',3'-dideoxynucleotide chain terminators (Sanger et al. (1977)) that carried fluorescent labels.

Complete VP1 PCR products of viruses for which VP1 primers were not available were obtained by cloning the viral cDNA into the plasmid pGEM-T-(Promega Corp., Madison, Wis.). Nested-deletion subclones were constructed from the resulting plasmid with an Erase-a-Base™ kit (Promega Corp.). In this procedure, the plasmid is first digested with a restriction nuclease providing either a blunt end or a 5' overhang. The opened plasmid is then digested with a 3'-5' exonuclease, *E. coli* exonuclease III, to remove plasmid sequences unrelated to the viral VP1 gene. The extended 5' overhang is then removed using S1 nuclease, and the plasmid is resealed by first repairing the ends with DNA polymerase, then ligating with DNA ligase. The resulting shortened plasmid is propagated in a suitable host to provide larger amounts of the plasmid, including the VP1 sequence. For each virus, at least two independent clones were sequenced by automated methods as described above.

Using these procedures, complete VP 1 nucleotide sequences were determined for 57 human non-polio enterovirus strains for which VP1 sequences had not previously been determined. These are summarized in Table 2, which shows both the GenBank accession numbers (numbers AF081293 to AF081349) and the corresponding SEQ ID NOs, 23-79. Forty-seven of the strains were prototype strains for recognized human enterovirus serotypes (Melnick (1996)). The other ten sequenced strains were well-characterized antigenic variants which, while antigenically distinct from their respective prototype strains, were similar enough to them to have been considered to be the same serotype (Committee on Enteroviruses of the National Foundation for Infantile Paralysis, Am. J. Public Health 47:1556-1566 (1957); Melnick (1996)). Combined with the 21 previously available complete enterovirus VP1 sequences, of which 19 are prototypes and 2 are variants, the database constructed for use in the present method includes 66 prototype VP1 sequences and 16 variants or other enteroviruses, including the three poliovirus Sabin strains and the Barty variant of E9.

The boundaries of the newly sequenced VP1 genes were predicted by comparison of the nucleotide and deduced amino acid sequences with those of previously characterized enteroviruses. Human enterovirus VP1 sequences varied in length from 834 to 951 nucleptides (278 to 317 amino acid residues). The CB group has the shortest predicted VP 1 amino acid sequences (278 to 298 residues), while EV68 and EV70 had the longest ones (312 and 317 residues, respectively).

Each of the enterovirus VP1 sequences developed in this work is characteristic of the serotype from which it arises, and differs from the sequence of every other serotype. For this reason, the VP1 sequences can be used as markers for the prototypical serotypes of the non-polio enteroviruses. The 66 prototype and 16 variant sequences identified above are used in the method of the present invention to form the content of a database for use in typing an enterovirus obtained in a clinical sample.

EXAMPLE 2

Design of Non-Polio Enterovirus PCR Primers and Assessment of the Breadth of Their Specificity Design of PCR primers. Since the VP1 sequence was found to correlate with serotype (Example 1), this region was targeted for development of sequence-based molecular diagnostics, namely, generic PCR primers to amplify and sequence a portion of the VP1 gene. Degenerate deoxyinosine-containing PCR primers were designed which specifically recognize regions within or near the termini of the VP1 gene of non-polio enteroviruses. Primers with the broadest specificity within the non-polio enterovirus genus were chosen by searching for regions in the genome that encode amino acid motifs within VP1 and those immediately C-terminal to VP 1, in 2A, that are the most conserved across the prototypes. (Echoviruses E22 and E23 were excluded, because it is likely that they will be reclassified as members of a new *Picomavirus* genus, *Parechovirus* (Mayo et al., J. Gen. Virol. 79:649-657 (1997)). The motif MYVPPG (Met-Tyr-Val-Pro-Pro-Gly) (SEQ ID NO:87) was present in the deduced VP1 amino acid sequences of 44 enterovirus prototype strains whose nucleotide sequences are provided in Example 1. Thirteen prototypes had Ile substituted for Val and CA7 contained Ala instead of Val. CAl2, CA14, and EV71 contain the motif, Iv17FVPPG (Met-Phe-Val-Pro-Pro-Gly) (SEQ ID NO:88). In EV68 and 70, a slightly different motif was present, MYVPTG (Met-Tyr-Val-Pro-Thr-Gly) (SEQ ID NO:89). For viruses in the CB-like phylogenetic group the M(Y/F)(V/I)PPG motif is followed by Gly (SEQ ID NO:86), whereas in all other enteroviruses, the motif is followed by Ala (A) (SEQ ID NO:86). To account for differences between the virus groups and for codon degeneracy, two different inosine-containing primers were designed to anneal to this region. Primer 012 (ATGTAYGTICCICCIGGIGG) (SEQ ID NO:4) is based on the amino acid sequence, MYVPPGG (SEQ ID NO:80). Primer 040 (ATGTAYRTICCIMCIGGIGC) (SEQ ID NO: 9) is based on the amino acid sequence, MY(V/I)P(P/T)GA (SEQ ID NO:81). The selectivity of these two primers is primarily due to the first position at the 3' end of each primer (i.e., in primer 012, the base at the 3' end is G, and in primer 040, the base at the 3' end is C) (see Table 3.) In addition, primer 040 contains increased degeneracy at positions 8 and 14 from the 3' end of the primer in order to detect those viruses which encode an isoleucine (position 8) or a threonine (position 14) in these positions. For PCR, primers 012 and 040 were each paired with primer 011 (GCICCIGAYTGITGICCRAA) (SEQ ID NO:3), which corresponds to the amino acid motif FG(Q/H)QSGA (Phe-Gly-(Gln/His)-Gln-Ser-Gly-Ala; SEQ ID NO:82), present near the 5' end of the 2A gene and which is conserved among most enteroviruses for which the 2A sequence is available.

Specificity of PCR Primers. To assess the breadth of specificity and thereby the general applicability of the 012/011 and 040/011 primer pairs, both pairs were tested in RT-PCR reactions with template RNA derived from each of the human non-polio enterovirus prototype strains (see FIG. 2). Primer pair 012/011 amplified 23 of 30 echovirus prototypes (FIG. 2C), as well as CA2, CA7, CA9, CA11, CB 1, CB2, CB3, CB6, and PV1 (Poliovirus 1) (FIG. 2A). Primer pair 040/011 amplified 14 of 23 CA prototypes and PV1 (FIG. 2B), as well as E2, E6, E14, E16, E18, E19, E20, E24, E25, E27, E30, and E31 (FIG. 2D). Twenty-two prototypes were not amplified by either primer pair (CA10, CA13, CA15, CA16, CA20, CA21, CA22, CB4, CB5, E1, E7, E9, E21, E22, E23, E32, EV68, EV 69, EV70, EV71, as well as PV2 and PV3, where PV signifies poliovirus).

EXAMPLE 3

Typing of Clinical Isolates Obtained in the Field

Viruses. Fifty-one virus isolates of 24 different serotypes were chosen from those processed in the inventors' laboratory at the Centers for Disease Control and Prevention (CDC) during the period 1991-1998 for routine non-polio enterovirus reference testing. The viruses were from 19 different states in the United States and two other countries, and were chosen to be representative of the serotypes in the collection for the period surveyed. To avoid the effects of sampling bias in the interpretation of sequence comparisons, no more than four isolates of any given serotype were chosen for sequencing. The isolates included examples of coxsackievirus A, coxsackievirus B, echovirus, and numbered enteroviruses.

Virus Isolation and Neutralization. The virus strains were isolated from a wide range of clinical specimens, including blood (n=1), cerebrospinal fluid (n=7), conjunctival swab (n=1), "lesion" (n=1), postmortem lung (n=1), nasopharyngeal swab (n=2), sputum (n=1), stool (n=18), throat swab (n=8), and tissue not specified (n=11). Forty-four of the 51 strains were originally isolated by the submitting laboratory, most of which were state public health laboratories in the United States. The remaining seven strains were isolated from original stool specimens at CDC. All isolates were typed antigenically using WHO-standard antiserum pools (Melnick et al., 1973), supplemented with additional pooled and monospecific antisera such that all human enterovirus serotypes, as well as antigenic variants of E4, E6, E11, and E30, could be identified (P. Feorino, personal communication to the inventors).

RNA extraction and RT-PCR. Viral RNA was extracted from infected cell culture supernatant using the QIAamp™ Viral RNA Kit (QIAGEN, Inc.). Reverse-transcription polymerase chain reaction (RT-PCR) was carried out as described previously (Oberste et al., (1998a,b)). From each viral cDNA, an amplicon of approximately 450 bp, encompassing the 3' half of VP1 and the 5' end of 2A, was amplified by PCR using the primers 012/011 or 040/011 (Table 3). Primer specificity was tested by PCR amplification of the prototype strain of each human enterovirus serotype with both primer pairs. Amplification products were visualized by agarose gel electrophoresis and ethidium bromide staining. PCR products from clinical isolates were gel-isolated and purified for sequencing using the QIAquick™ Gel Extraction Kit (QIAGEN, Inc.) and sequenced on an automated DNA sequencer using fluorescent dideoxy-chain terminators as in Example 1 (Applied Biosystems Division, Perkin Elmer, Inc.). The sequences obtained for the clinical samples were deposited in the GenBank sequence database (Accession Numbers AF08 1 595-AF08 1645).

Sequence Analysis. The sequences were compared to the enterovirus VP1 sequence database developed in Example 1 by sequential pairwise alignment of the query sequence with each sequence in the database, using the algorithm of Needleman and Wunsch (1970), implemented in the program Gap (Wisconsin Sequence Analysis Package, version 9.1). The results of the pairwise comparisons were compiled and sorted in descending order by percent identity with the query sequence.

PCR-amplification of Clinical Isolates. In order to establish the utility of using viral sequence analysis as an enterovirus typing tool, typing by partial sequencing of VP1 was compared with the conventional serological typing method using 52 clinical isolates typed in the inventors' laboratory from 1991 to 1997. Partial VP1 sequences relate to obtaining sequences in a region of approximately 400 nucleotides at the 3' end of the VP1 gene. Despite the failure of primer pair 012/011 to amplify the E7, E9, E21, CB4 and CB5 prototype strains (see Example 2), 012/011 successfully amplified recent clinical isolates of each these serotypes. Likewise, primer pair 040/011 amplified recent isolates of CA16, CA21, and EV71, but not the prototype strains of these serotypes (see Example 2). Taken together, these two primer pairs failed to amplify only one clinical isolate of the 52 tested, a 1993 EV6 isolate from Texas (TX93-1673). The presence of amplifiable RNA in the latter specimen was confirmed by amplification of 5'-specific sequences by pan-enterovirus primers (data not shown). For the other 51 isolates, a VP1-specific fragment was amplified from purified RNA by RT-PCR using primer pairs 012/011 or 040/011. In most cases, only one of the two primer pairs produced an amplicon of the expected size (data not shown).

Typing of Clinical Isolates by Nucleotide Sequence Analysis. The PCR products were gel isolated and sequenced. The sequences were compared to the complete enterovirus VP1 database developed in Example 1 by pairwise alignment of the isolate sequence to each sequence in the database using the program Gap. These comparisons produced, for each clinical isolate, a set of values of the percent identity giving the extent of identity between the sequence of the given clinical isolate and each of the prototype sequences in the database. Typing was obtained as that prototype whose extent of identity to the clinical sample was the highest of all the prototypes. In general, as implemented in this study, if the highest global identity is >75%, the clinical sample and the prototype are of the same serotype. If the highest score is 70%-75%, the identification is presumptive and should be confirmed by neutralization using monospecific antisera specific for each of the four highest scoring prototypes. If the highest score is <70%, the clinical sample is considered to be of no known serotype; for example, it may be from a picomavirus for which a sequence is not yet available, or it may be a new enterovirus serotype. For each clinical isolate, the matches with the highest and second highest pairwise identity score were identified. Table 4 shows the serotype as obtained from the classical neutralization test, as well as the types of the highest and next highest scoring prototypes obtained in this way (with entries giving the extent of identity of both the nucleotide sequences (nt) and the translated amino acid sequences(aa)). Strains in Table 4 are identified by U.S. state (two letter code) or country (three letter code) of origin, year of isolation, and lab identifier number. For example, WA91-0374 indicates that the strain was isolated in the state of Washington in 1991 and the lab sample number was 0374. The abbreviations DOR and PER in Table 4 designate the Dominican Republic and Peru, respectively.

TABLE 4

Correspondence Between Typing by Sequence and by Neutralization.

| Strain | Neut. Type | Highest Scoring Prototype | | | Second Highest Scoring Prototype(s) | | | |
|---|---|---|---|---|---|---|---|---|
| | | Type | nt (%) | aa (%) | Type | nt (%) | Type | aa (%) |
| WA91-0374 | E6 | E6 | 83.3 | 95.6 | E1 | 69.7 | E29 | 74.3 |
| OR91-1426 | E30 | L30 | 85.8 | 92.9 | E21 | 69.5 | E21 | 81.7 |
| CT92-1465 | E16 | E16 | 81.4 | 93.6 | E5 | 72.2 | E5 | 78.6 |
| FL92-1512 | CB2 | CB2 | 86.5 | 98.5 | CB4 | 68.3 | CB4 | 75.2 |
| WA92-1516 | E11' | E11 | 77.1 | 90.1 | E11 | 72.9 | E19 | 83.0 |
| NC92-1612 | E9 | E9 | 77.8 | 94.6 | E17 | 70.2 | E16 | 72.9 |
| GA92-1616 | E11 | E11 | 77.6 | 89.4 | E19 | 72.2 | E19 | 82.3 |
| TX92-1647 | CA14 | CA14 | 86.8 | 91.1 | CA7 | 63.4 | CA7 | 67.9 |
| MD92-1649 | E25 | E25 | 77.1 | 91.5 | E1 | 68.5 | E21 | 77.6 |
| DOR93-1657 | CA24v | CA24 | 77.4 | 92.8 | CA20 | 67.6 | CA17 | 75.9 |

TABLE 4-continued

Correspondence Between Typing by Sequence and by Neutralization.

| Strain | Neut. Type | Highest Scoring Prototype | | | Second Highest Scoring Prototype(s) | | |
|---|---|---|---|---|---|---|---|
| | | Type | nt (%) | aa (%) | Type | nt (%) | Type | aa (%) |
| FL93-1763 | E11' | E11 | 78.5 | 90.1 | E19 | 72.6 | E19 | 83.0 |
| GA93-1763 | CA9 | CA9 | 93.8 | 95.3 | E4 | 68.6 | E4 | 70.8 |
| GA93-1765 | E7 | E7 | 79.7 | 95.7 | E32 | 68.8 | E32 | 77.1 |
| MO93-1808 | E25 | E25 | 77.6 | 91.5 | E33 | 67.5 | E21 | 76.9 |
| ME93-1814 | CB5 | CB5 | 95.2 | 98.5 | CB1 | 71.3 | CB1 | 77.7 |
| NM93-1816 | CB3 | CB3 | 90.3 | 97.7 | CB6 | 69.9 | CB1 | 81.5 |
| OR93-1817 | E25 | E25 | 77.9 | 91.5 | E1 | 68.5 | E21 | 76.9 |
| WA93-1821 | E4 | E4 | 81.1 | 96.1 | E1 | 73.1 | E1 | 80.9 |
| MN94-1828 | E25 | E25 | 76.9 | 92.2 | E29 | 67.9 | E21 | 77.6 |
| WA94-1849 | E3 | E3 | 79.6 | 93.0 | E7 | 68.2 | E12 | 80.0 |
| AR94-1884 | E30 | E30 | 96.0 | 93.6 | E21 | 70.0 | E21 | 82.4 |
| GA93-2460 | CB5 | CB5 | 95.8 | 93.5 | CB1 | 70.8 | CB1 | 77.7 |
| GA93-1892 | E30 | E30 | 85.5 | 93.6 | E21 | 69.5 | E21 | 83.4 |
| GA93-1994 | E7 | E7 | 79.7 | 95.7 | E32 | 69.1 | E32 | 77.1 |
| NM94-1919 | EV71 | EV71 | 80.6 | 93.4 | CA16 | 66.9 | CA16 | 76.6 |
| AZ94-1925 | CA14 | CA14 | 86.5 | 97.0 | CA7 | 63.8 | CA7 | 68.2 |
| RI94-1959 | E21 | E21 | 78.3 | 93.7 | E30 | 69.6 | E30 | 80.0 |
| CT94-2006 | EV71 | EV71 | 80.3 | 93.4 | CA16 | 66.0 | CA16 | 76.6 |
| MD95-2037 | EV71 | EV71 | 79.9 | 92.7 | CA16 | 67.0 | CA16 | 76.6 |
| AZ94-2060 | CA21 | CA21 | 90.9 | 98.6 | CA24 | 68.7 | CA24 | 75.5 |
| PA94-5753 | CA16 | CA16 | 77.9 | 94.7 | EV71 | 68.7 | EV71 | 83.0 |
| NM95-2070 | E6 | E6 | 76.8 | 94.1 | E29 | 68.1 | E29 | 75.5 |
| TX95-2089 | E13 | E13 | 72.4 | 88.7 | EV69 | 71.5 | EV69 | 93.0 |
| GA95-2093 | CA21 | CA21 | 91.4 | 98.6 | CA24 | 67.5 | CA24 | 75.5 |
| GA95-2095 | CA16 | CA16 | 77.9 | 94.9 | EV71 | 69.4 | EV71 | 77.4 |
| NC95-2135 | CB2 | CB2 | 83.2 | 99.2 | CB4 | 68.3 | CB4 | 76.2 |
| AR95-2139 | E9 | E9 | 75.7 | 92.8 | E17 | 70.0 | E1 | 71.8 |
| TX95-2147 | CA16 | CA16 | 76.5 | 94.9 | EV71 | 70.4 | EV71 | 77.4 |
| VA95-2154 | E11' | E11 | 78.3 | 90.8 | E19 | 71.7 | E19 | 83.7 |
| WT95-7151 | E9 | E9 | 75.7 | 93.5 | E17 | 69.4 | E16 | 71.4 |
| VA95-2157 | E30 | E30 | 85.3 | 92.1 | E21 | 70.0 | E21 | 82.1 |
| GA96-2175 | CA9 | CA9 | 81.5 | 92.6 | E19 | 68.4 | E11 | 72.3 |
| CT96-2181 | E5 | E5 | 86.5 | 92.9 | E31 | 71.5 | E31 | 82.1 |
| CT96-2181 | E18 | E18 | 75.7 | 93.6 | E17 | 69.9 | E4 | 75.4 |
| TX96-2184 | CA21 | CA21 | 91.6 | 98.6 | CA24 | 68.2 | CA24 | 75.5 |
| TX97-2320 | E18 | E18 | 78.8 | 92.9 | E17 | 69.7 | E17 | 74.5 |
| NH97-2342 | CB3 | CB3 | 77.4 | 98.5 | CB5 | 67.9 | CB1 | 84.6 |
| PER98-2528 | E6 | E6 | 86.0 | 95.6 | CB1 | 71.6 | E29 | 74.3 |
| PER98-2533 | E7 | E7 | 80.4 | 95.7 | E32 | 68.1 | E12 | 78.6 |
| PER98-2537 | E11 | E11 | 78.5 | 94.3 | E19 | 71.9 | E19 | 82.3 |
| PER98-2558 | E33 | E33 | 79.3 | 96.9 | CB1 | 70.3 | E4 | 75.4 |

The typing results for the 51 isolates shown in Table 4, fully correlate with the serotype as determined by the conventional neutralization test (Table 4). The nucleotide sequences of the various clinical isolates ranged from 72.4% identity to 95.2% identity with the sequences of the respective prototype strains and only from 63.4% identity to 73.1% identity to the sequences of the second highest scoring prototypes. The predicted amino acid sequences of the clinical isolates ranged from 88.7% identity to 98.5% identity with that of the cognate prototype strain and from 67.7% identity to 84.6% identity to that of the second highest scoring prototype strain. With one exception, the difference between percent nucleotide sequence identity to the highest scoring prototype and the percent identity to the second highest scoring prototype was 4.2%. In the exception (TX95-2089), typed antigenically as E13; the highest-to-second-highest difference was only 0.9% (72.4% identical to E13 vs. 71.5% identical to EV69), suggesting that either TX95-2089 has diverged significantly from E13 or EV69, or that the E13 prototype strain (Del Carmen) is not representative of the serotype as a whole. When the complete VP I nucleotide sequence of TX95-2089 was examined, it was found to be 72.6% identical to that of the E13 prototype, 70.1% identical to that of the EV69 prototype (second highest score), and 64.7% identical to that of the E12 prototype (third highest score). The predicted complete VP1 amino acid sequence of TX95-2089 was 88.2% identical to that of E13, 80.8% identical to that of EV69 (second highest score), and 70.0% identical to that of CB1 (third highest score), suggesting that TX95-2089 is probably a strain of E13 which has diverged in nucleotide sequence by accumulating mutations in the third codon position. TX95-2089 was neutralized by monospecific anti-E13 antisera but not by monospecific anti-EV69 antisera (data not shown).

The typing procedure described in this invention contravenes the evaluation of the state of the art in Holland et al. (J. Clin. Microbiol. 36:1588-1594 (1998)), which states that PCR is not able successfully to type enterovirus infections. Furthermore, Oberste et al. (1998a) conducted sequence and phylogenetic analyses of all human enterovirus serotypes based on a portion of the VP2 gene. They determined that this portion of VP2 may be inappropriate for consistent molecular inference of serotype. For these reasons, the method of the present invention, as described above and exemplified in Examples 1-3, provides results that are unexpected by workers in the field.

EXAMPLE 4

Detection of a Broad Range of Picornaviruses

The present method has been applied to the detection of a broad range of picornaviruses that afflict both human and nonhuman subjects, according to the procedures generally followed in Example 2.

In addition to the primers 011, 012, and 040, additional primers directed to the detection of human and nonhuman picornaviruses were devised. These are provided as Primer 187 (ACIGCIGYIGAPACIGGNCA) (SEQ ID NO:19) that hybridizes to a sequence encoding the amino acid motif TA(A/V)ETGH (SEQ ID NO:83), Primer. 188 (ACIGCIGTI-GARACIGGNG) (SEQ ID NO:20) that hybridizes to a sequence encoding the amino acid motif TAVETG(A/V) (SEQ ID NO:84), Primer 189 (CARGCIGCIGARACIG-GNGC) (SEQ ID NO:21) that hybridizes to a sequence encoding the amino acid motif QAAETGA (SEQ ID NO:85), and Primer 222 (CICCIGGIGGIAYRWACAT) (SEQ ID NO:22) that hybridizes to a sequence encoding a motif M(F/Y)(I/V)PPG(A/G) (SEQ ID NO:86) (see Table 3). Primer 187 is directed to amplification of the CB and E groups in the forward direction (i.e., it hybridizes to the sense strand of the cDNA), Primer 188 is directed to amplification of the poliovirus (PV) group, EV68 and EV70 in the forward direction, Primer 189 is directed to amplification of the group of CA16-like viruses (Oberste et al., J. Virol. 73:1941-1948 (1999)) in the forward direction, and Primer 222 is directed to amplification of all enteroviruses in the reverse direction (i.e., it hybridizes to the antisense strand of the cDNA).

In this example, prototypical serotypes of human enteroviruses were subjected to RT-PCR using, in separate experiments, primer pairs 012/011 (SEQ ID NOs:3 and 4), 040/011 (SEQ ID NOs:3 and 9), 187/222 (SEQ ID NOs:19 and 22), 188/222 (SEQ ID NOs:20 and 22), and 189/222 (SEQ ID NOs:21 and 22). The results are shown in Table 5. Additionally several serotypes from a selection of human and nonhuman picornaviruses, namely bovine enterovirus, human rhinovirus, and simian picornavirus, were examined according to the present method. For simian picornaviruses and HRV2, actual experiments were done. For the other serotypes considered, provision of an amplicon was predicted by comparison of the primer sequences to each of the viral VP1 sequences. The results of this experiment are shown in Table 6.

TABLE 5

Amplification of Human Enterovirus Serotypes by Specific Primer Pairs.

| Virus | 012/011 | 040/011 | 187/222 | 188/222 | 189/222 |
|---|---|---|---|---|---|
| CA1 | - | - | - | ■ | □ |
| CA2 | - | □ | ■ | □ | □* | ■ |
| CA3 | - | ■ | - | □ | ■ |
| CA4 | - | ■ | - | - | ■ |
| CA5 | - | ■ | □ | □* | ■ |
| CA6 | - | ■ | - | □* | ■* |
| CA7 | - | - | ± | - | ■ |
| CA8 | - | □ | - | □ | ■ |
| CA9 | ■ | - | ■* | □ | - |
| CA10 | - | - | - | □ | ■ |
| CA11 | - | ± | - | ■ | □ |
| CA12 | - | ■ | - | □* | ■ |
| CA13 | - | - | □* | ■ | □ |
| CA14 | - | ■ | - | □ | ■ |
| CA15 | - | - | □ | ■ | □ |
| CA16 | - | ■ | - | - | ■ |
| CA17 | - | ± | ± | ■ | □ |
| CA18 | - | ■ | - | (±) | - |
| CA19 | - | ± | - | ■ | □ |
| CA20 | - | - | - | ■ | ± |
| CA21 | - | ■ | - | ■ | □ |
| CA22 | - | - | - | ■ | □ |
| CA24 | - | ■ | - | ■ | □ |
| CB1 | ■ | - | ■ | - | - |
| CB2 | ■ | - | ■ | □* | ± |
| CB3 | ■ | ± | ■* | - | ± |
| CB4 | - | - | ■* | - | ± |
| CB5 | ■ | - | ■ | □ | □ |
| CB6 | ■ | - | ■ | □* | □* |
| PV1 | - | ■ | □ | ■ | □ |
| PV2 | - | - | □ | ■ | □* |
| PV3 | - | - | - | ■ | □ |
| E1 | - | - | ■ | - | - |
| E2 | ■ | □ | ■ | - | ± |
| E3 | ■ | - | ■ | - | ± |
| E4 | ■ | - | ■* | □ | □* |
| E5 | ■ | - | ■ | - | ± |
| E6 | ■ | □ | ■ | - | ± |
| E7 | ■ | - | (±) | - | □ |
| E9 | ■ | - | ■ | - | ± |
| E11 | ■ | - | ■* | - | ± |
| E12 | ■ | - | ■* | - | □* |
| E13 | ■ | - | ■ | - | □ |
| E14 | ■ | □ | ■ | - | □* |
| E15 | - | - | ■ | - | - |
| E16 | ■ | - | ■ | - | ± |
| E17 | ■ | - | ■* | - | ± |
| E18 | ■ | □ | ■ | □ | □ |
| E19 | ■ | - | ■ | - | ± |
| E20 | ■ | □ | ■ | □ | ± |
| E21 | ■ | - | ■ | - | - |
| E24 | ■ | □ | ■ | - | ± |
| E25 | ■ | □ | ■ | - | ± |
| E26 | ■ | - | ■ | - | ± |
| E27 | ■ | □ | ■* | - | ± |
| E29 | - | - | ■ | - | - |
| E30 | ■ | □ | ■ | - | ± |
| E31 | ■ | □ | ■* | - | ± |
| E32 | - | - | ■ | - | ± |
| E33 | ■ | - | ■ | - | - |
| EV68 | - | - | □ | ■ | □ |
| EV69 | - | - | ■ | - | - |
| EV70 | - | - | - | ■ | □ |
| EV71 | - | ■ | - | - | ■ |

CA, coxsackie A virus;
CB, coxsackie B virus;
PV, poliovirus;
E, echovirus;
EV, numbered enterovirus.
Results are for amplification of prototype strains and/or clinical isolates of the indicated serotypes, based on testing in a standard RT-PCR assay for human enteroviruses (Oberste et al., 1999).
□ and ■: strong amplification, single band on gel;
■ indicates the primer pair giving optimal amplification for a particular serotype.
± and (±): weak amplification, single band on gel;
(±) indicates the primer pair giving optimal amplification for a particular serotype.
□* and ■*: strong amplification, multiple bands on gel;
■* indicates the primer pair giving optimal amplification for a particular serotype.
–: No amplification observed.

TABLE 6

Predicted and Observed Results of Amplification of Picornavirus Serotypes by Specific Primer Pairs.

| Virus | 012/ 011 | 040/ 011 | 187/ 222 | 188/ 222 | 189/ 222 |
|---|---|---|---|---|---|
| BEV1 | | | | [■] | |
| BEV2a | | | | [■] | |
| BEV2b | | | | [■] | |
| HRV1b | | | [■] | | |
| HRV2 | | | ■ | | |
| HRV3 | | | | [■] | |
| HRV14 | | | | | [■] |
| HRV16 | | | [■] | | |
| HRV89 | | | [(±)] | | |
| SPV2 | | ■ | | | |
| SPV9 | – | – | – | – | – |
| SPV10 | | ■ | | | |
| SPV11 | – | – | – | ■ | – |
| SPV12 | – | – | – | – | ■ |
| SPV13 | | ■ | | | |
| SPV15 | – | – | – | ■ | – |
| SPV16 | – | – | – | – | ■ |
| SPV17 | | | | ■ | □ |

BEV, bovine enteroviruses;
HRV, human rhinovirus;
SPV, simian picornavirus.
Results are for amplification of prototype strains and/or clinical isolates of the indicated serotypes, based on testing in a standard RT-PCR assay (Oberste et al., 1999) for HRV2, and simian picornaviruses. For the other viruses (indicated by square brackets [ ]), the entry provides a predicted result based on comparison of the primer sequences with the available VP1 nucleotide sequences found in the GenBank database.

□ and ■: strong amplification, single band on gel;
■ indicates the primer pair giving optimal amplification for a particular serotype.
(±): weak amplification, single band on gel, optimal amplification for a particular serotype.
–: No amplification observed.
Empty cells indicate primer-template combinations that have not yet been tested.

Figure 2:
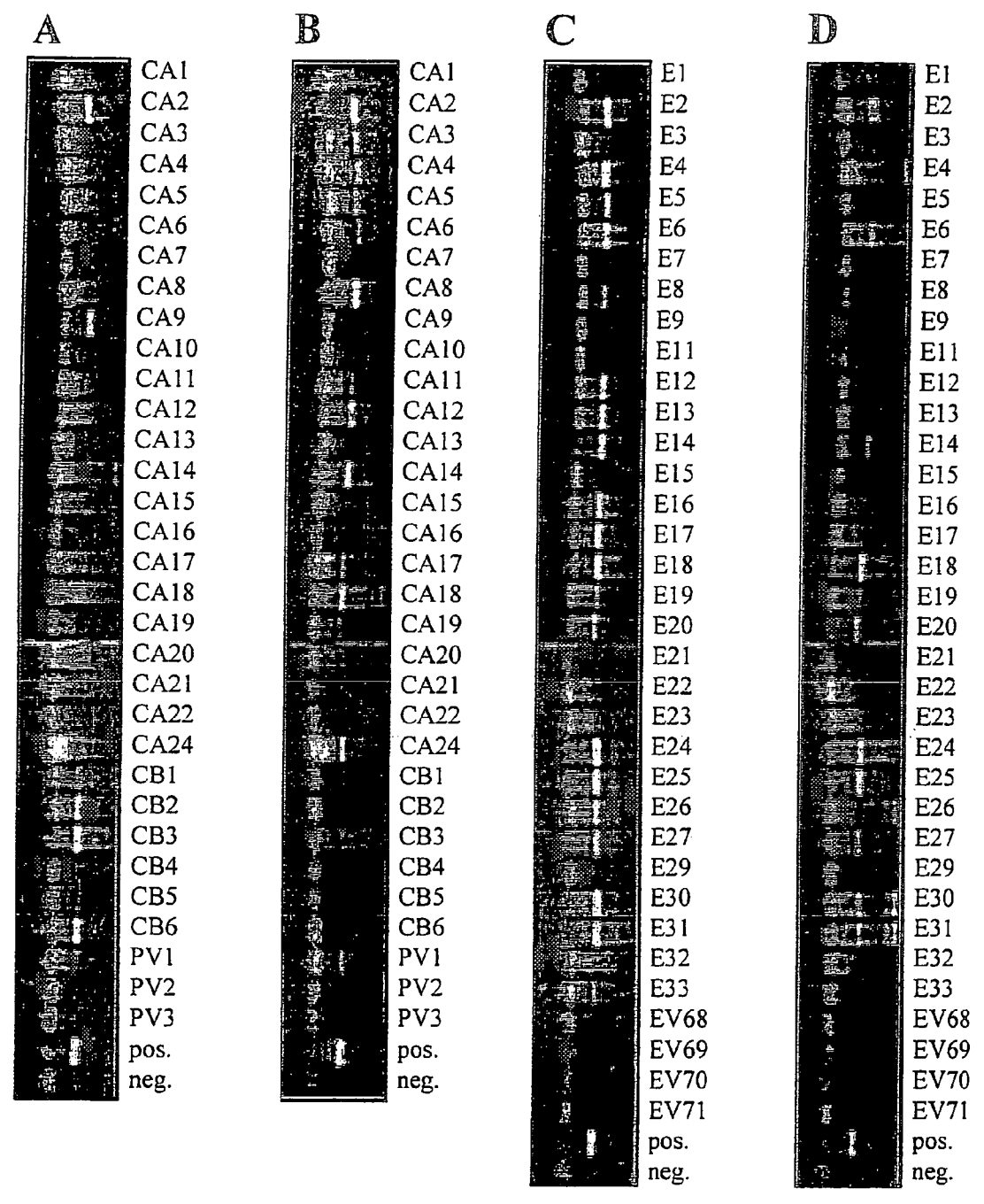

The results for 012/011 and 040/011 in Table 5 tabulate the observations already discussed with respect to FIG. 2 in Example 2.

Taking the results for primer pairs 187/222, 188/222, and 189/222 in Tables 5 and 6 together, it is seen that these primer pairs amplify all human enteroviruses, and five of the six simian picomaviruses tested. They should also amplify the three bovine enteroviruses and all six human rhinoviruses for which VP1 sequences are available in GenBank; other than HRV2, these have not yet been directly tested. Furthermore, the three simian picomaviruses that were not tested using primer pairs 187/222, 188/222, and 189/222 were successfully amplified by primer pair 040/011 (see Table 6).

We claim:

1. A method for typing an enterovirus in a clinical sample comprising the steps of:
   (i) obtaining a clinical sample from a subject,
   (ii) purifying RNA contained in the sample,
   (iii) reverse transcribing the RNA with primers effective to reverse transcribe enteroviral RNA to provide a cDNA;
   (iv) contacting at least a portion of the cDNA with
      (a) a composition that promotes amplification of a nucleic acid and
      (b) an oligonucleotide mixture wherein the mixture comprises at least one oligonucleotide that hybridizes to a highly conserved sequence of the sense strand of an enterovirus nucleic acid and at least one oligonucleotide that hybridizes to a highly conserved sequence of the antisense strand of an enterovirus nucleic acid, wherein the highly conserved sequences occur within the VP1 gene or within about 100 nucleotides from a terminus of the VP1 gene, and at least one oligonucleotide comprises, at the 3' end thereof, a sequence that hybridizes to a sequence encoding a motif chosen from the group consisting of the sequences given by SEQ ID NO:83, SEQ ID NO:84, and SEQ ID NO:85, and at least one oligonucleotide comprises, at the 3' end thereof, a sequence that hybridizes to a sequence encoding a motif given by SEQ ID NO:86, thereby providing an amplification mixture, such that, upon hybridizing, the oligonucleotides direct amplification of at least a portion of the nucleotide sequence of the VP1 gene of a non-polio enterovirus;
   (v) carrying out an amplification procedure on the amplification mixture, such that, if an enterovirus is present in the sample, an enterovirus sample amplicon is produced whose sequence comprises a nucleotide sequence of at least a portion of the VP1 region of the enterovirus genome;
   (vi) determining that the sample amplicon is present;
   (vii) determining at least a partial nucleotide sequence of the sample amplicon;
   (viii) providing a database consisting of prototypical nucleotide sequences, wherein each prototypical sequence is the sequence of a standard amplicon obtained from a member of a set of prototypical enterovirus serotypes by carrying out the procedure of steps (ii) through (v) on each prototypical enterovirus serotype, wherein each prototypical sequence comprises at least a portion of the sequence of the VP1 gene, and wherein the sequence of each prototypical VP1 gene is different from the sequence of every other prototypical VP1 gene in the database;
   (ix) comparing the sequence of the sample amplicon with each prototypical sequence in the database; and
   (x) identifying the prototypical sequence that has the highest extent of identity to the sequence of the sample amplicon to provide an identified serotype; wherein the type of the sample is the serotype of the identified serotype.

2. The method as described in claim 1, wherein the oligonucleotide mixture comprises an oligonucleotide whose sequence comprises, at the 3' end thereof, the sequence given by SEQ ID NO:22, and at least one oligonucleotide chosen from the group consisting of an oligonucleotide whose sequence comprises, at the 3' end thereof, the sequence given by SEQ ID NO:19, an oligonucleotide whose sequence comprises, at the 3' end thereof, the sequence given by SEQ ID NO:20, and an oligonucleotide whose sequence comprises, at the 3' end thereof, the sequence given by SEQ ID NO: 21.

3. The method as described in claim 2, wherein the oligonucleotide mixture comprises an oligonucleotide whose sequence is given by SEQ ID NO:22, and at least one oligonucleotide chosen from the group consisting of an oligonucleotide whose sequence is given by SEQ ID NO:19, an oligonucleotide whose sequence is given by SEQ ID NO:20, and an oligonucleotide whose sequence is given by SEQ ID NO:21.

4. The method as described in claim 1, wherein the sample is chosen from the group consisting of whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, and tissue from an experimentally infected animal.

5. The method as described in claim 1, wherein the amplification procedure comprises a polymerase chain reaction.

6. The method as described in claim 1, wherein an amplicon encompasses at least a portion of the nucleotide sequence for the VP1 gene of an enterovirus.

7. The method as described in claim 1, wherein the set of prototypical enterovirus serotypes comprises serotypes of coxsackie A viruses, coxsackie B viruses, echoviruses, and numbered enteroviruses.

8. The method as described in claim 7, wherein the serotypes of coxsackie A viruses (CA) comprise CA1 through CA22 and CA24.

9. The method as described in claim 7, wherein the serotypes of coxsackie B viruses (CB) comprise CB1 through CB6.

10. The method as described in claim 7, wherein the serotypes of echoviruses (E) comprise E1 through E7, E9, and E11 through E27, and E29 through E33.

11. The method as described in claim 7, wherein the serotypes of numbered enteroviruses (EV) comprise EV68 through EV71.

12. The method as described in claim 1, wherein determining at least a partial nucleotide sequence of the sample amplicon comprises a sequencing method chosen from the group consisting of a method using 2',3'-dideoxynucleotide chain terminators and a method using chemical degradation of terminally-labeled amplicons.

13. The method as described in claim 1, wherein comparing the sequence of the sample amplicon with each sequence in the database employs a sequence alignment and comparison algorithm.

* * * * *

UNITED STATES PATENT AND TRADEMARK OFFICE
CERTIFICATE OF CORRECTION

PATENT NO. : 7,435,539 B2  Page 1 of 2
APPLICATION NO. : 11/042898
DATED : October 14, 2008
INVENTOR(S) : Oberste et al.

It is certified that error appears in the above-identified patent and that said Letters Patent is hereby corrected as shown below:

On the Title Page Item (56):

Under 'Other Publications,' "Homotype" should be --Homotypic--.

Column 1, Line 27, "within. the" should be --within the--.

Column 3, Line 14, "picomaviruses" should be --picornaviruses--.

Column 13, Line 29, "picomaviruses" should be --picornaviruses--.

Column 3, Line 38, "3 11" should be --311--.

Column 4, Line 50, "presence er or absence of" should be --presence or absence of--.

Column 4, Line 63, "couple, with" should be --coupled with--.

Column 7, Line 3, "tat" should be --that--.

Column 8, Line 6, "SEQ ID NO: 2 1" should be --SEQ ID NO: 21--.

Column 9, Line 51, "contains; at" should be --contains, at--.

Column 11, Line 42, "targeted. segment" should be --targeted segment--.

Column 16, Line 27, "48874891" should be --4887-4891--.

Column 17, Line 58, "supernatant. from" should be --supernatant from--.

Column 18, Line 17, "sequences in. the" should be --sequences in the--.

Signed and Sealed this

Thirty-first Day of August, 2010

David J. Kappos
*Director of the United States Patent and Trademark Office*

CERTIFICATE OF CORRECTION (continued)
U.S. Pat. No. 7,435,539 B2

Column 18, Lines 51-52, "picomaviruses" should be --picornaviruses--.

Column 20, Line 18, "4146" should be --41-46--.

Column 20, Line 28, "DATP, dATP" should be --dATP, dCTP--.

Column 20, Lines 35-36, "DATP, D.C.TP, dGTP, and TrP" should be --dATP, dCTP, dGTP, and TTP--.

Column 20, Line 59, "pGEM-T-(Promega" should be --pGEM-T (Promega--.

Column 21, Line 7, "VP 1" should be --VP1--.

Column 21, Line 31, "nucleptides" should be --nucleotides--.

Column 21, Line 32, "VP 1" should be --VP1--.

Column 21, Line 64, "Picomavirus" should be --Picornavirus--.

Column 22, Line 4, "Cal2" should be --CA12--.

Column 22, Line 5, "Iv17FVPPG" should be --MFVPPG--.

Column 22, Lines 8-9, "M(Y/F)(V/I) PPG" should be --M (Y/F)(V/I)PPG--.

Column 23, Lines 32, "AF08 1 595-AF08 1645" should be --AF081595-AF081645--.

Column 24, Lines 34-35, "picomavirus" should be --picornavirus--.

Column 25, Line 60, "E13; the" should be --E13, the--.

Column 25, Line 65, "VP I" should be --VP1--.

Column 27, Line 12, "...GAPACI..." should be --...GARACI...--.

Column 27, Line 14, "Primer. 188" should be --Primer 188--.

Column 30, Line 24, "picomaviruses" should be --picornaviruses--.

Column 30, Line 28, "picomaviruses" should be --picornaviruses--.